(12) United States Patent
Kataoka et al.

(10) Patent No.: US 7,579,187 B2
(45) Date of Patent: *Aug. 25, 2009

(54) ANTI-A33 ANTIBODY

(75) Inventors: Shiro Kataoka, Takasaki (JP);
Takafumi Tomura, Takasaki (JP);
Noriko Otani, Takasaki (JP)

(73) Assignee: Kyoma Hakko Kirin Co., Ltd., Tokyo (JP)

( * ) Notice: Subject to any disclaimer, the term of this patent is extended or adjusted under 35 U.S.C. 154(b) by 13 days.

This patent is subject to a terminal disclaimer.

(21) Appl. No.: 11/629,779

(22) PCT Filed: Sep. 2, 2005

(86) PCT No.: PCT/JP2005/016576

§ 371 (c)(1),
(2), (4) Date: Dec. 15, 2006

(87) PCT Pub. No.: WO2006/028197

PCT Pub. Date: Mar. 16, 2006

(65) Prior Publication Data

US 2007/0141054 A1 Jun. 21, 2007

(30) Foreign Application Priority Data

Sep. 6, 2004 (JP) .............................. 2004-259090

(51) Int. Cl.
C12N 5/06 (2006.01)
C12N 5/16 (2006.01)
C07K 16/00 (2006.01)
A61K 39/395 (2006.01)
C12P 21/04 (2006.01)
G01N 33/53 (2006.01)
C12P 21/08 (2006.01)

(52) U.S. Cl. ...................... 435/330; 435/326; 435/69.6; 435/7.1; 530/387.1; 530/388.1; 424/130.1; 424/138.1; 424/141.1

(58) Field of Classification Search ........................ None
See application file for complete search history.

(56) References Cited

U.S. PATENT DOCUMENTS

| 5,160,723 | A | 11/1992 | Welt et al. | |
|---|---|---|---|---|
| 5,585,089 | A | 12/1996 | Queen et al. | |
| 5,643,550 | A | 7/1997 | Welt et al. | |
| 5,958,412 | A * | 9/1999 | Welt et al. | 424/178.1 |
| 6,307,026 | B1 | 10/2001 | King et al. | |
| 2002/0199213 | A1 * | 12/2002 | Tomizuka et al. | 800/18 |

FOREIGN PATENT DOCUMENTS

| AU | 200239422 | 5/2004 |
|---|---|---|
| CA | 1 306 706 | 4/1986 |
| CN | 1487996 | 5/2004 |
| EP | 120694 | 10/1984 |
| EP | 125023 | 11/1984 |
| EP | 0 199 141 A2 | 10/1986 |
| EP | 1354034 | 5/2004 |
| GB | 2188638 A | 10/1987 |
| IN | 200300651 | 5/2004 |
| JP | 62-111697 | 5/1987 |
| JP | 2004-515230 | 5/2004 |
| JP | 2004-259090 | 9/2004 |
| KR | 2003074634 | 5/2004 |
| MX | 2003004793 | 5/2004 |
| WO | WO 01/30393 A2 | 5/2001 |
| WO | WO 02/43478 | 6/2002 |

OTHER PUBLICATIONS

Kazuma Tomizuka et al., "Double trans-chromosomic mice: Maintenance of two individual human chromosome fragments containing Ig heavy and κ loci and expression of fully human antibodies", PNAS, vol. 97, No. 2, Jan. 18, 2000, pp. 722-727.

Sydney Welt et al., "Preliminary Report of a Phase I Study of Combination Chemotherapy and Humanized A33 Antibody Immunotherapy in Patients with Advanced Colorectal Cancer", Clinical Cancer Research, vol. 9, Apr. 2003, pp. 1347-1353.

Ando, et al., Tan-Clone-Kotai-Jikken-Manual ("Experimental Manual for Monoclonal Antibody") (written by and published by Kodansha Scientific, Ltd., Tokyo, Japan (1991).

Bruggemann, et al., "The Immunogenicity of Chimeric Antibodies", J. Exp. Med., Dec. 1989, vol. 170, No. 6, pp. 2153-2157.

Delves, P. J., "Antibody Production Essential Techniques", Monoclonal Antibodies, Ed. Shepherd and Dean, Oxford University Press, 2000.

Fishwild, et al., "High-avidity Human IgGκ Monoclonal Antibodies from a Novel Strain of Minilocus Transgenic Mice," Nat Biotechnol., Jul. 1996, vol. 14, No. 7, pp. 845-851.

(Continued)

Primary Examiner—David J. Blanchard
Assistant Examiner—Anne M. Gussow
(74) Attorney, Agent, or Firm—Foley & Lardner LLP

(57) ABSTRACT

The present invention provides: an antibody or a antibody fragment thereof, which can bind to A33, which specifically attacks A33-expressing tumor cells with the use of ADCC and CDC based on the immune system, and for which no HAHA is produced; and a preventive or therapeutic agent for various malignant tumors including solid tumors that are currently treated with difficulty, which contains the antibody or an antibody fragment thereof. Specifically, the antibody or a functional fragment thereof is capable of binding to A33 and is produced by a hybridoma M10 (accession No. FERM BP-10107), M96 (accession No. FERM BP-10108), M165 (accession No. FERM BP-10106), N26 (accession No. FERM BP-10109), Q47 (accession No. FERM BP-10104), Q54 (accession No. FERM BP-10105), or R5 (accession No. FERM BP-10107). The preventive or therapeutic agent for tumors contains the antibody or a functional fragment thereof.

9 Claims, 19 Drawing Sheets

OTHER PUBLICATIONS

Garin-Chesa, et al., "Organ-specific expression of the Colon Cancer Antigen A33, a Cell Surface Target for Antibody-based Therapy", *International J. Oncology*, Sep. 1996, vol. 9, No. 3, pp. 465-471.

Goding, J. W., *Monoclonal Antibodies: Principles and Practice*, Academic Press, 1993.

Green, L., "Antibody Engineering via Genetic Engineering of the Mouse; XenoMouse Strains are a Vehicle for the Facile Generation of Therapeutic Human Monoclonal Antibodies," *Journal of Immunological Methods*, 1999, No. 231, pp. 11-23.

Ishida & Lonberg, IBC's 11th Antibody Engineering, Abstract 2000.

Janeway, et al., *Immunobiology*, Current Biology Ltd/Garland Publishing Inc., 1997.

Katakura, et al., "Productivity Enhancement of Recombinant Protein in CHO Cells via Specific Promoter Activation by Oncogenes", *Cytotechnology*, 1999, vol. 31, pp. 103-109.

Kearney, et al., "A New Mouce Myeloma Cell Line that has Lost Immunoglobulin Expression but Permits the Construction of Antibody-Secreting Hybrid Cell Lines", *J. Immunology*, Sep. 1979, vol. 123, No. 3, pp. 1548-1550.

King, D.J., *Applications and Engineering of Monoclonal Antibodies*, T. J. International Ltd, 1998.

King, et al., "Preparation of Preclinical Evaluation of Humanized A33 Immunoconjugates for Radioimmunotherapy", *British J. Cancer*, Dec. 1995, vol. No. 6, pp. 1364-1372.

Kohler, et al., "Derivation of Specific Antibody-producing Tissue Culture and Tumor Lines by Cell Fusion", *European J. Immunology*, 1966, vol. 6, pp. 511-519.

Margolin, et al., "Phase Ib Trial of Intravenous Recombinant Humanized Monoclonal Antibody to Vascular Endothelial Growth Factor in Combination with Chemotherapy in Patients with Advanced Cancer: Pharmacologic and Long-Term Safety Data", *J. Clin. Oncol.*, Feb. 2001, vol. 19, No. 3, pp. 851-856.

Mark, et al., "Site-specific Mutagenesis of the Human Fibroblast Interferon Gene", *Proc Natl Acad Sci U.S.A.*, Sep. 1984, vol. 81, No. 18, pp. 5662-5666.

Matteucci and Caruthers, "Synthesis of Deoxyoligonucleotides on a Polymer Support", *J. Am. Chem. Soc.*, Jun. 1981. vol. 103, No. 11, pp. 3185-3191.

Riechmann, et al., "Reshaping Human Antibodies for Therapy", *Nature*, Mar. 1988, vol. 332, No. 6162, pp. 323-327.

Schroff, et al., "Human Anti-Murine Immunoglobulin Responses in Patients Receiving Monoclonal Antibody Therapy", *Canc. Res.*, Feb. 1985, vol. 45, No. 2, pp. 879-885.

Shulman, et al., "A Better Cell Line for Making Hybridomas Secreting Specific Antibodies", *Nature*, Nov. 1978, vol. 276, No. 5685, pp. 269-270.

Tao, et al., "Structural Features of Human Immunoglobulin G that Determine Isotype-specific Differences in Complement Activation", *J. Exp. Med*, Aug. 1993, vol. 178, pp. 661-667.

Welt, et al., "Phase I Study of Anticolon Cancer Humanized Antibody A33", *Clinical Cancer Res.*, Apr. 2003, vol. 9, No. 4, pp. 1338-1346.

Welt, et al., "Phase I/II Study of Iodine 131-Labeled Monoclonal Antibody A33 in Patients with Advanced Colon Cancer", *J. Clinical Oncology*, Aug. 1994, vol. 12, No. 8, pp. 1561-1571.

Welt, et al., "Phase I/II Study of Iodine 125-Labeled Monoclonal Antibody A33 in Patients with Advanced Colon Cancer", *J. Clinical Oncology*, Jun. 1996, vol. 14, No. 6, pp. 1787-1797.

Wright, et al., "High Level Expression of Active Human Alpha-1-Antitrypsin in the Milk of Transgenic Sheep", *Bio/Technology*, Jul. 1991, vol. 9, No. 7, pp. 830-834.

Yelton, et al., "Fusion of Mouse Myeloma and Spleen Cells", *Current Topics in Microbiology and Immunology*, 1978, vol. 81, pp. 1-7.

Supplementary European Search Report, EP 05778552 issued Feb. 26, 2009, 5 pages.

Rader, et al., "The Rabbit Antibody Repertoire as a Novel Source for the Generation of Therapeutic Human Antibodies", *J. Biol. Chem.*, May 5, 2000, vol. 275, No. 18, pp. 13668-13676.

* cited by examiner c) 125M10AA f) 125Q54AAA

Bar=200 µm b) rec263 e) recN26 a) Chimeric anti-human A33 antibody d) recM165 c) 125M10AA f) 125Q54AAA

Bar=200 μm b) rec263 e) recN26 a) Chimeric anti-human A33 antibody d) recM165 a) Chimeric anti-human A33 antibody b) rec263 c) 125M10AA f) 125Q54AAA e) recN26 d) recM165

Bar=200 μm

M10 : 125M10AA
M96 : 125M96ABA
M165 : 125M165DAAA

M165-10 : recM165-10 μg/head

M165-100 : recM165-100 μg/head

N26-10 : recN26-10 μg/head

N26-100 : recN26-100 μg/head

N26-10 : recN26-10 μg/head
N26-100 : recN26-100 μg/head
M165-10 : recM165-10 μg/head
M165-100 : recM165-100 μg/head M10-10 : recM10-10 μg/head
M10-100 : recM10-100 μg/head
Q54-10 : recQ54-10 μg/head
Q54-100 : recQ54-100 μg/head

ANTI-A33 ANTIBODY

TECHNICAL FIELD

The present invention relates to an anti-A33 antibody that specifically binds to an A33 antigen. Furthermore, the present invention relates to a preventive or therapeutic agent for diseases due to A33-expressing cells, which comprises the anti-A33 antibody as an active ingredient. The present invention particularly relates to a therapeutic agent for malignant tumors.

BACKGROUND ART

Cancer (tumor) is the leading cause of death in Japan and the number of cancer patients is increasing each year. Hence, the development of drugs or therapeutic methods against cancer that have high effectiveness and safety has been strongly desired. Among various types of cancer, colorectal cancer accounted for 12.2% of total cancer cases, as shown in the survey conducted in 1999. The colorectal cancer mortality rates ranked third in the case of men and second in the case of women. Based on the significantly increased number of colorectal cancer cases in recent years, colorectal cancer morbidity or mortality is predicted to surpass the same for gastric cancer in the future. Furthermore, gastric cancer accounted for 17.4% of total cancer cases, as shown in the survey conducted in 1999, and the mortality rates thereof ranked second in the case of men and first in the case of women.

The use of an antibody as a remedy is being recognized as an important and valuable approach for the treatment of various pathological conditions (cancer types). Antibody specificity is useful for treating pathological conditions wherein a tumor-specific antigen exhibits the properties of heterologous cells. Antibodies effectively target such cells through binding to tumor-specific antigens, which are proteins to be expressed on cell surfaces. Currently, a chimeric antibody (Rituximab) that targets at CD20 (the receptor existing on the cell membranes), a monoclonal antibody such as a humanized antibody that targets at Her2/neu, and the like have been used against malignant tumors as subject diseases. The therapeutic effects thereof have been recognized. Antibodies are characterized by long blood half-life and high specificity to antigens, and they are particularly useful as antitumor agents. For example, in the case of an antibody that targets a tumor-specific antigen, it is inferred that the administered antibody is accumulated in tumors. Furthermore, the immune system that attacks against cancer cells through the use of complement-dependent cytotoxicity (CDC) and antibody-dependent cellular cytotoxicity (ADCC) can be expected. Moreover, previous binding of a drug (such as a radioactive nuclide or a cytotoxic substance) to the antibody enables efficient delivery of the bound drug to tumor sites. Simultaneously, since the amounts of such drugs that reach other non-specific tissues are decreased, alleviation of side effects can also be expected. Through administration of an antibody having agonistic activity when a tumor-specific antigen has activity of inducing cell death or through administration of an antibody having neutralization activity when a tumor-specific antigen is involved in the growth and survival of cells, the accumulation of such tumor-specific antibody and the suspension of tumor growth or the degeneration of tumors through the activity of such antibody can be expected. It is thought that antibodies are appropriate for use as antitumor agents because of their features as described above.

Mice have been used as target animals in early antibody production. However, the use of mouse antibodies in vivo is limited for many reasons. Mouse antibodies that are recognized by human hosts as extraneous matter induce "human anti-mouse antibodies," with such induction referred to as the "HAMA" response (see Schiff et al., Canc. Res. (1985), 45, 879-885). Furthermore, the Fc portions of mouse antibodies are not effective for stimulation of human complements or cytotoxicity.

A chimeric antibody has been developed as an approach to avoid such problem (see European Patent Application Nos. 120694 and 125023). A chimeric antibody contains parts of antibodies derived from 2 or more species (e.g., a mouse antibody variable region and a human antibody constant region). Such chimeric antibody has the advantage of retaining the features of a mouse antibody and can stimulate a human complement or cytotoxicity because of its human Fc. However, such chimeric antibody still induces a "human anti-chimeric antibody;" that is, "HACA" response (see Bruggemann, et al., J. Exp. Med., 170, 2153-2157, 1989).

Furthermore, a recombinant antibody has been developed, wherein only one substituted antibody portion is a complementarity determining region (that is, "CDR") (British Patent No. GB2188638A and U.S. Pat. No. 5,585,089). An antibody comprising mouse CDR, a human variable framework, and a constant region (that is, a "humanized antibody") has been produced using CDR-grafting technology (see Riechmann, et al., Nature (1988), 332, 323-327).

A mouse anti-A33 antibody against an antigen that is a class I cell membrane protein referred to as "A33," a member of the Ig superfamily, and a tumor-specific antigen and a humanized antibody have been reported (see U.S. Pat. No. 5,958,412, Description; King D. J. et al., British J. Cancer (1995) 72, 1364-1372; Welt S. et al., J. Clinical Oncology (1994), 12, 1561-1571; Welt S. et al., J. Clinical Oncology (1996), 14, 1787-1797; Welt S. et al., Clinical Cancer Res. (2003), 9, 1338-1346; and Welt S. et al., Clinical Cancer Res. (2003), 9, 1347-1353). Involvement of such antigen in colon cancer and gastric cancer is known (see U.S. Pat. No. 5,643,550, Description; U.S. Pat. No. 5,160,723, Description; and Garin-Chesa P. G. et al., International J. Oncology (1996), 9, 465-471). Furthermore, in recent years, phase I clinical tests using the humanized A33 antibody have been conducted for colon cancer patients (see Welt S. et al., Clinical Cancer Res. (2003), 9, 1338-1346 and Welt S. et al., Clinical Cancer Res. (2003), 9, 1347-1353). In the former report about the administration of the antibody alone, partial reactions were observed in 1 out of 11 patients to which the antibody could be administered. Moreover, in the latter report about the test using the antibody and chemotherapy in combination, partial reactions were observed in 3 out of 12 patients to which the antibody could be administered, and a mixed reaction was observed in 1 of the same. Even in the case of Avastin™ (Bevacizumab; humanized anti-VEGF antibody) under development by Genentech in recent years, there is a report that 1 out of 12 patients showed partial reactions in the phase I clinical test using Avastin™ and standard chemotherapy in combination (Margolin K. et al., J. Clin. Oncol. (2001) 19, 851-856). Accordingly, based on the result that 1 out of 11 patients showed partial reactions as a result of the administration of the antibody alone, the antibody is expected to exert extensive antitumor effects against colorectal cancer.

Although the humanized A33 antibody showed very significant tumor reactions in the phase I clinical tests as described above, human anti-humanized antibodies (that is, "HAHAs") were produced in both tests with probabilities as high as 50% or more. Interestingly, no HAHA was observed in patients in which the antibody showed high tumor reactivity.

DISCLOSURE OF THE INVENTION

The object of the present invention is to provide a preventive or therapeutic agent for various malignant tumors, including solid tumors, that are currently treated with difficulty through the development of an antibody that can bind to A33, specifically attacks A33-expressing tumor cells with the use of ADCC or CDC based on the immune system, and does not cause the production of HAHA.

As described above, it is thought that an antibody that targets the A33 antigen is appropriate for use as an antitumor agent. In addition, with the use of such an antibody by which no HAHA is produced, even higher antitumor effects may be obtained. Hence, as a result of intensive studies concerning the production of an antibody against A33, the present inventors have succeeded in obtaining a monoclonal antibody showing antitumor effects against A33-expressing cancer cells and have specified the sequences of the variable regions of the monoclonal antibody. Thus, the present inventors have completed the present invention.

Specifically, the present invention is as described below.

In the first aspect, the present invention provides a monoclonal antibody binding to A33, which is produced by a mouse-mouse hybridoma. Specifically, a monoclonal antibody, which is preferably a human antibody, or a functional fragment thereof produced by 263A17, 125M10AA, 125M165DAAA, 125M96ABA, 125N26F6AA, 125Q47BA, 125Q54AAAA, or 125R5AAAA, for example, is provided. The type of such monoclonal antibody produced by 263A17, 125M10AA, 125M165DAAA, 125M96ABA, 125N26F6AA, 125Q47BA, 125Q54AAAA, or 125R5AAAA is human immunoglobulin G (IgG) type. Among the above hybridomas, 125M10AA, 125M165DAAA, 125M96ABA, 125N26F6AA, 125Q47BA, 125Q54AAAA, and 125R5AAAA were deposited on Aug. 24, 2004, with the International Patent Organism Depositary (IPOD) (Central 6, 1-1, Higashi 1, Tsukuba, Ibaraki, Japan), the National Institute of Advanced Industrial Science and Technology (AIST) under accession Nos. FERM BP-10107 (denotation for identification: M10), FERM BP-10106 (denotation for identification: M165), FERM BP-10108 (denotation for identification: M96), FERM BP-10109 (denotation for identification: N26), FERM BP-10104 (denotation for identification: Q47), FERM BP-10105 (denotation for identification: Q54), and FERM BP-10103 (denotation for identification: R5), respectively.

In an embodiment of the present invention, the antibody of the present invention is an antibody or a functional fragment thereof, which has the variable regions of an antibody produced by one of the above hybridomas.

In another embodiment of the present invention, examples of the antibody of the present invention include antibodies of modified subclasses. Specifically, the antibody of the present invention may be: an antibody or a functional fragment thereof which is produced by hybridoma 263A17 and is of the subclass human IgG1, human IgG2, human IgG3, or human IgG4; an antibody or a functional fragment thereof which is produced by hybridoma 125M10AA and is of the subclass human IgG1, human IgG2, human IgG3, or human IgG4; an antibody or a functional fragment thereof which is produced by hybridoma 125M165DAAA and is of the subclass human IgG1, human IgG2, human IgG3, or human IgG4; an antibody or a functional fragment thereof which is produced by hybridoma 125M96ABA and is of the subclass human IgG1, human IgG2, human IgG3, or human IgG4; an antibody or a functional fragment thereof which is produced by hybridoma 125N26F6AA and is of the subclass human IgG1, human IgG2, human IgG3, or human IgG4; an antibody or a functional fragment thereof which is produced by hybridoma 125Q47BA and is of the subclass human IgG1, human IgG2, human IgG3, or human IgG4; an antibody or a functional fragment thereof which is produced by hybridoma 125Q54AAAA and is of the subclass human IgG1, human IgG2, human IgG3, or human IgG4; or an antibody or a functional fragment thereof which is produced by hybridoma 125R5AAAA and is of the subclass human IgG1, human IgG2, human IgG3, or human IgG4.

Furthermore, in another aspect of the present invention, the present invention provides an antibody or a functional fragment thereof, which binds to A33 and contains the variable regions of an antibody produced by hybridoma 263A17, 125M10AA, 125M165DAAA, 125M96ABA, 125N26F6AA, 125Q47BA, 125Q54AAAA, or 125R5AAAA.

In an embodiment of the present invention, the antibody of the present invention is an antibody or a functional fragment thereof having the variable regions of the amino acid sequences represented by SEQ ID NOS: 23 and 25. In another embodiment of the present invention, the antibody of the present invention is an antibody or a functional fragment thereof having the variable regions of the amino acid sequences represented by SEQ ID NOS: 27 and 29. In another embodiment of the present invention, the antibody of the present invention is an antibody or a functional fragment thereof having the variable regions of the amino acid sequences represented by SEQ ID NOS: 31 and 33. In another embodiment of the present invention, the antibody of the present invention is an antibody or a functional fragment thereof having the variable regions of the amino acid sequences represented by SEQ ID NOS: 35 and 37. In another embodiment of the present invention, the antibody of the present invention is an antibody or a functional fragment thereof having the variable regions of the amino acid sequences represented by SEQ ID NOS: 39 and 41. In another embodiment of the present invention, the antibody of the present invention is an antibody or a functional fragment thereof having the variable regions of the amino acid sequences represented by SEQ ID NOS: 43 and 45. In another embodiment of the present invention, the antibody of the present invention is an antibody or a functional fragment thereof having the variable regions of the amino acid sequences represented by SEQ ID NOS: 47 and 49. In another embodiment of the present invention, the antibody of the present invention is an antibody or a functional fragment thereof having the variable regions of the amino acid sequences represented by SEQ ID NOS: 51 and 53. In another embodiment of the present invention, the antibody of the present invention is an antibody or a functional fragment thereof having the entire region of both of the amino acid sequences represented by SEQ ID NOS: 87 and 89.

In another aspect, the present invention further provides the above antibody or a functional fragment thereof that suppresses tumor growth (e.g., derived from colorectal cancer cell line COLO205 cells implanted in nude mice). Upon the suppression of tumors, the antibody or a functional fragment thereof of the present invention is administered to a tumor-bearing animal to be tested (e.g., a tumor-bearing experimental animal such as a colon cancer cell tumor-bearing mouse model having a body weight of 20 g) in an amount between 10 μg/body and 100 μg/body. The dose is 100 μg/body or 5 mg/kg, and preferably 10 μg/body or 0.5 mg/kg, for example.

In an embodiment of the present invention, the antibody of the present invention has one of the following properties.

(a) ADCC Test

In the presence of normal human peripheral blood mononuclear cells, the antibody of the present invention exerts antibody-dependent cellular cytotoxicity (ADC) against A33-expressing human cancer cells.

(b) CDC Test

In the presence of human serum-derived complements, the antibody of the present invention exerts complement-dependent cytotoxicity (CDC) against A33-expressing human cancer cells.

(c) In vivo Test

The antibody of the present invention exerts antitumor effects against non-human animals bearing A33-expressing human cancer cells.

(d) Competition Test

The antibody of the present invention is (i) strongly competitive (blocker), (ii) weakly competitive (partial blocker), or (iii) not competitive (non-blocker) with chimeric anti-A33 (comprising the heavy chain variable region and the light chain variable region of an antibody produced by hybridoma ATCC HB-8779 and the heavy chain constant region and the light chain constant region of human IgG1).

(e) Immunohistochemical Test

The presence of the antibody of the present invention results in the staining of human adult colon cancer tissues, human adult normal colon tissues, and human normal small intestine tissues.

In another aspect, the present invention further provides: a nucleic acid encoding an antibody possessed by a hybridoma selected from the group consisting of hybridomas 125M10AA (accession No. FERM BP-10107), 125M165DAAA (accession No. FERM BP-10106), 125M96ABA (accession No. FERM BP-10108), 125N26F6AA (accession No. FERM BP-10109), 125Q47BA (accession No. FERM BP-10104), 125Q54AAAA (accession No. FERM BP-10105), and 125R5AAAA (accession No. FERM BP-10103) or a nucleic acid encoding a functional fragment of the antibody; a protein encoded by the nucleic acid; an expression vector having the above nucleic acid; and a host selected from the group consisting of *Escherichia coli*, a yeast cell, an insect cell, a mammalian cell, a plant cell, and a mammal having the expression vector.

In another aspect, the present invention further provides a method for producing an anti-A33 monoclonal antibody or a functional fragment thereof, which comprises: isolating a gene encoding an anti-A33 monoclonal antibody (e.g., a gene encoding a variable region of a heavy chain amino acid sequence and a gene encoding a variable region of a light chain amino acid sequence) from a hybridoma selected from the group consisting of hybridomas 263A17, 125M10AA, 125M165DAAA, 125M96ABA, 125N26F6AA, 125Q47BA, 125Q54AAAA, and 125R5AAAA; constructing an expression vector having such gene; introducing the expression vector into a host; culturing the host; causing the expression of the monoclonal antibody; and harvesting the anti-A33 monoclonal antibody or a functional fragment thereof from the thus obtained host or culture products such as the culture supernatant of the host, the secretion product of the host, or the like.

In another aspect, the present invention further provides a preventive, therapeutic, or diagnostic agent for tumors, which contains the above antibody or a functional fragment thereof as an active ingredient.

Examples of tumors that can be prevented or treated with the use of the above agent include at least one tumor selected from the group consisting of colorectal cancer, colon cancer, rectal cancer, gastric cancer, pancreatic cancer, breast cancer, melanoma, renal cell cancer, cervical cancer, endometrial cancer, ovarian cancer, esophageal cancer, prostatic cancer, testicular cancer, and mesothelial cancer.

In another embodiment of the present invention, the antibody or a functional fragment thereof of the present invention is characterized in that a dose of 10 μg/body or 100 μg/body of the above antibody or a functional fragment thereof is confirmed to exhibit suppression (after tumor grafting) of the tumors of tumor-bearing nude mice wherein COLO205 cells are implanted to a more significant degree than that in the case of a group of the mice to which a vehicle is administered or a group of the mice to which an anti-DNP-IgG1 antibody is administered.

The present invention also relates to: an antibody binding to A33, which recognizes the same epitope as that recognized by an antibody that is produced by hybridoma M10 (accession No. FERM BP-10107); an antibody binding to A33, which recognizes the same epitope as that recognized by an antibody that is produced by hybridoma M96 (accession No. FERM BP-10108); an antibody binding to A33, which recognizes the same epitope as that recognized by an antibody that is produced by hybridoma M165 (accession No. FERM BP-10106); an antibody binding to A33, which recognizes the same epitope as that recognized by an antibody that is produced by hybridoma N26 (accession No. FERM BP-10109); an antibody binding to A33, which recognizes the same epitope as that recognized by an antibody that is produced by hybridoma Q47 (accession No. FERM BP-10104); an antibody binding to A33, which recognizes the same epitope as that recognized by an antibody that is produced by hybridoma Q54 (accession No. FERM BP-10105); and an antibody binding to A33, which recognizes the same epitope as that recognized by an antibody that is produced by hybridoma R5 (accession No. FERM BP-10103).

This description includes part or all of the contents as disclosed in the description and/or drawings of Japanese Patent Application No. 2004-259090, which is a priority document of the present application.

PREFERRED EMBODIMENTS OF THE INVENTION

Figure 1A:
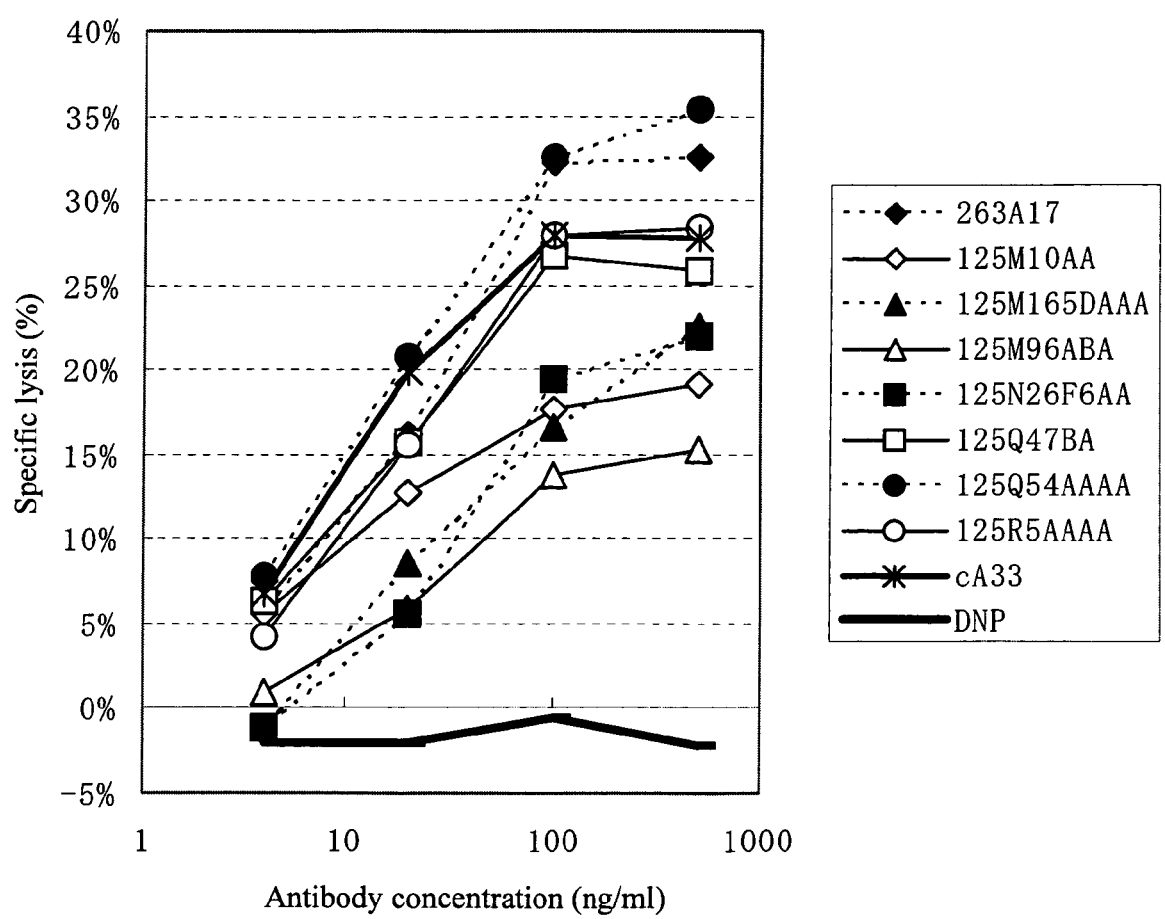
FIG. 1A shows ADCC activity determined when COLO205 cells were targeted using each purified monoclonal antibody.
Figure 1B:
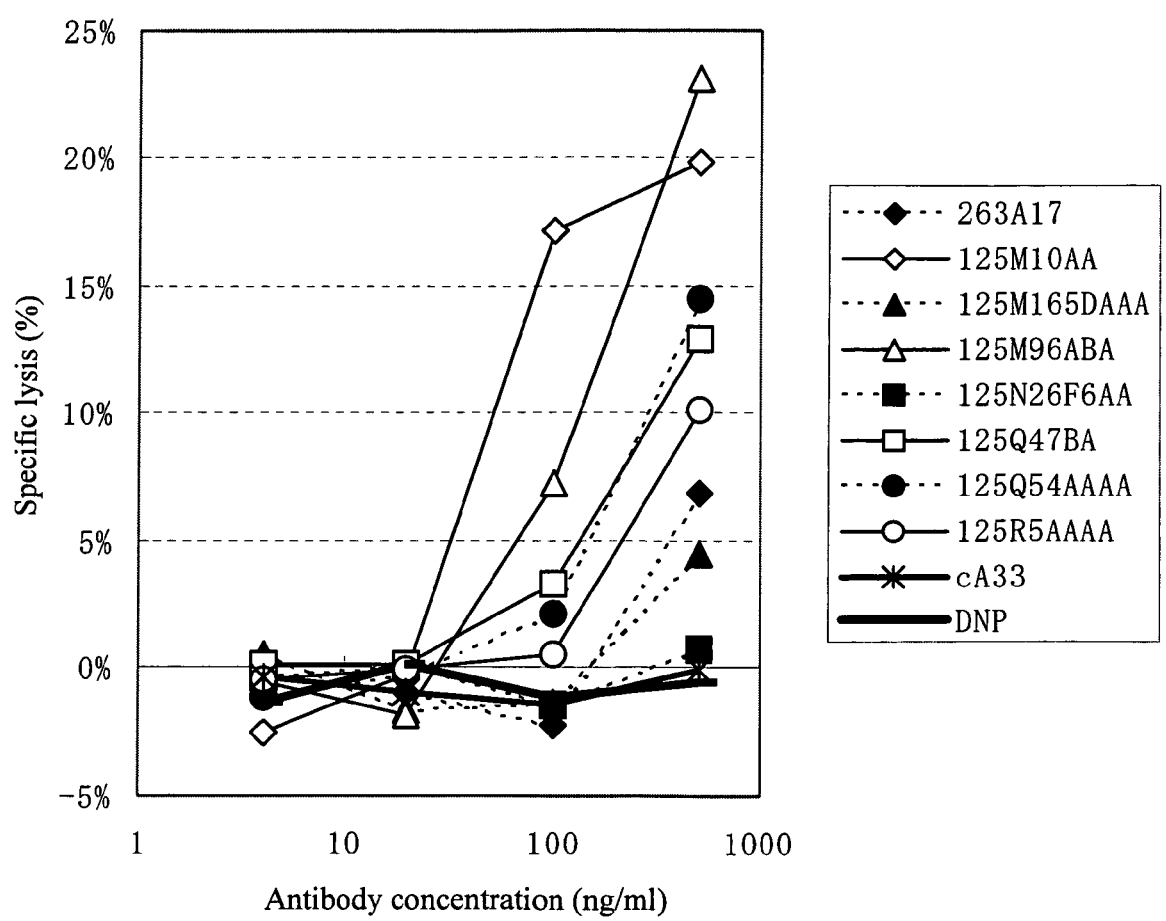
FIG. 1B shows CDC activity determined when COLO205 cells were targeted using each purified monoclonal antibody.
Figure 1C:
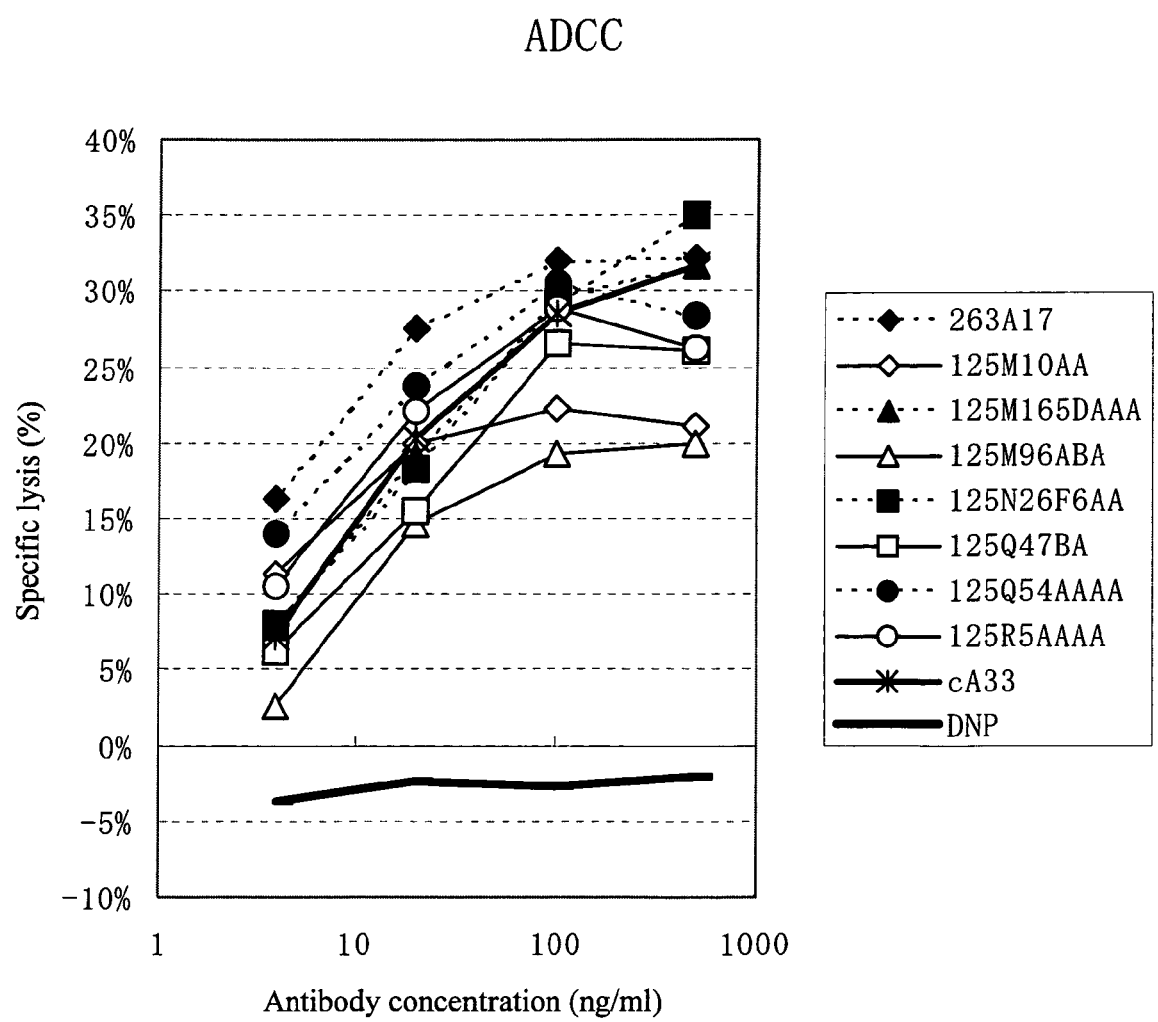
FIG. 1C shows ADCC activity determined when NCI-H508 cells were targeted using each purified monoclonal antibody.
Figure 1D:
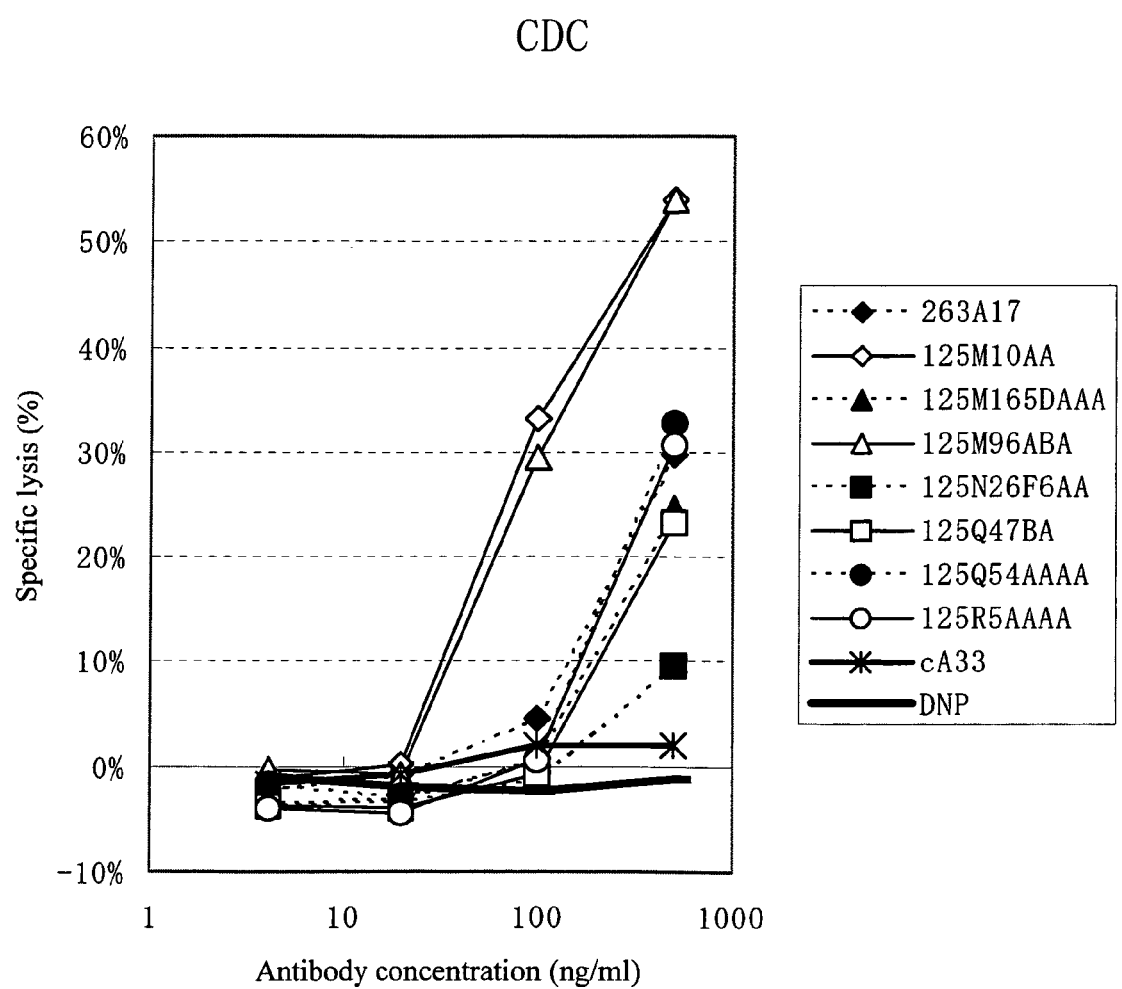
FIG. 1D shows CDC activity determined when NCI-H508 cells were targeted using each purified monoclonal antibody.
Figure 2A:
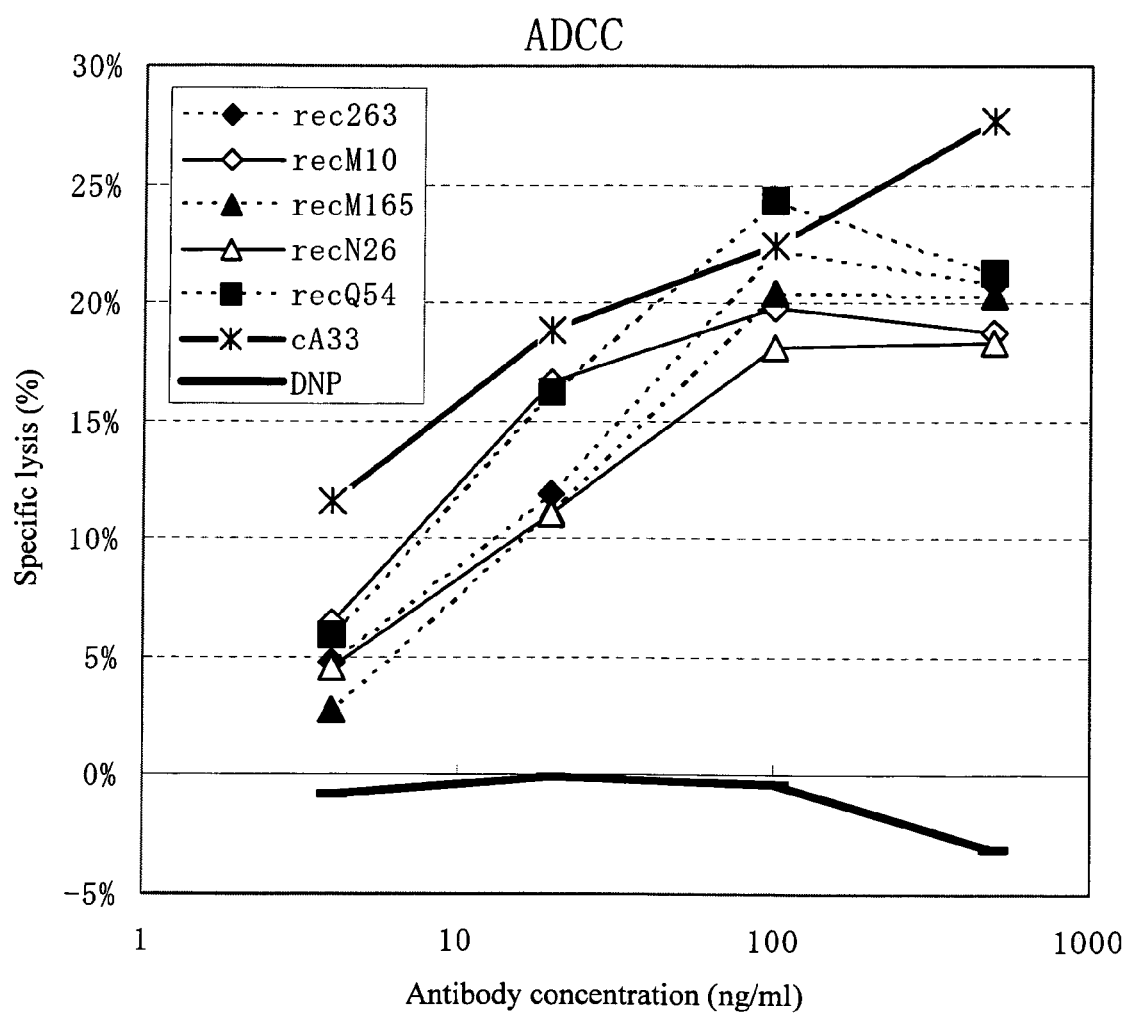
FIG. 2A shows ADCC activity determined when COLO205 cells were targeted using recombinant antibodies.
Figure 2B:
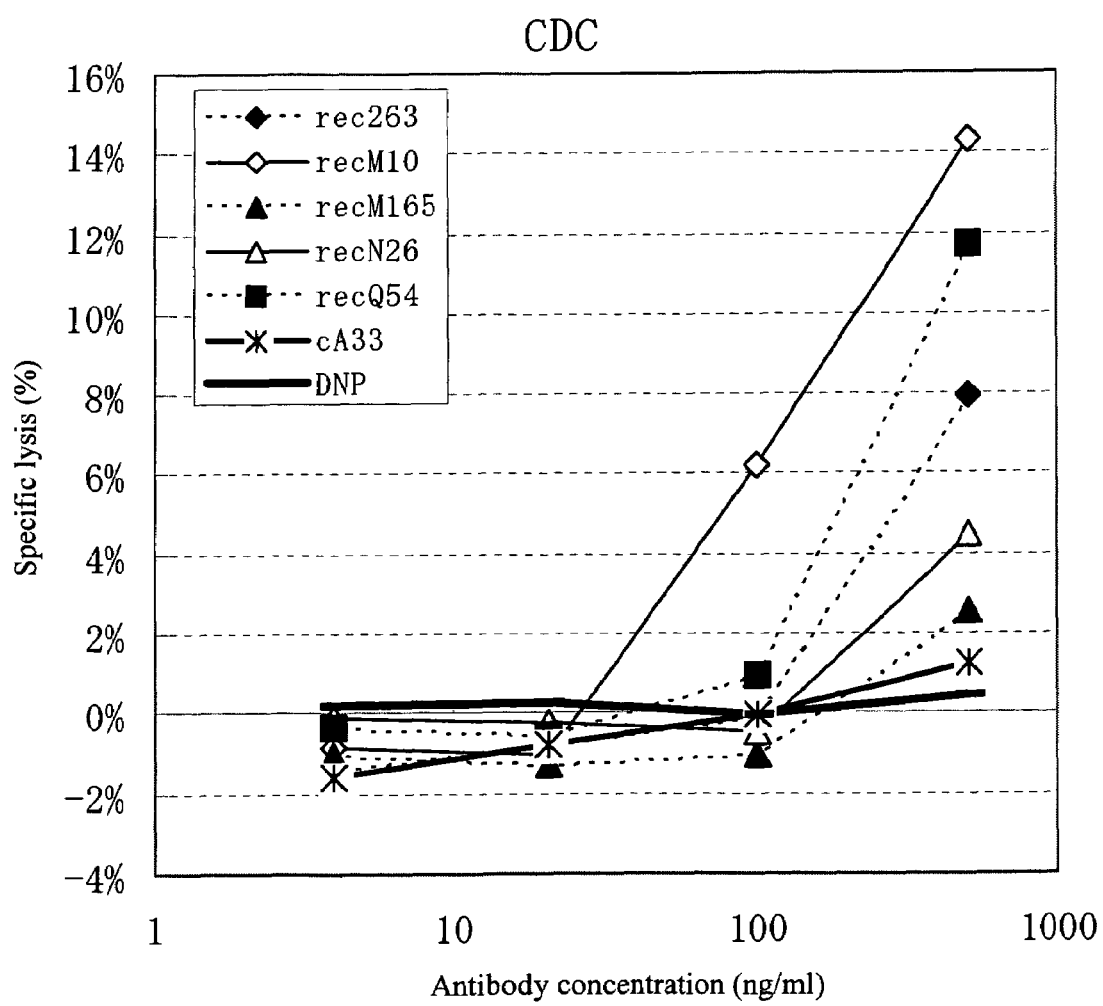
FIG. 2B shows CDC activity determined when COLO205 cells were targeted using recombinant antibodies.
Figure 2C:
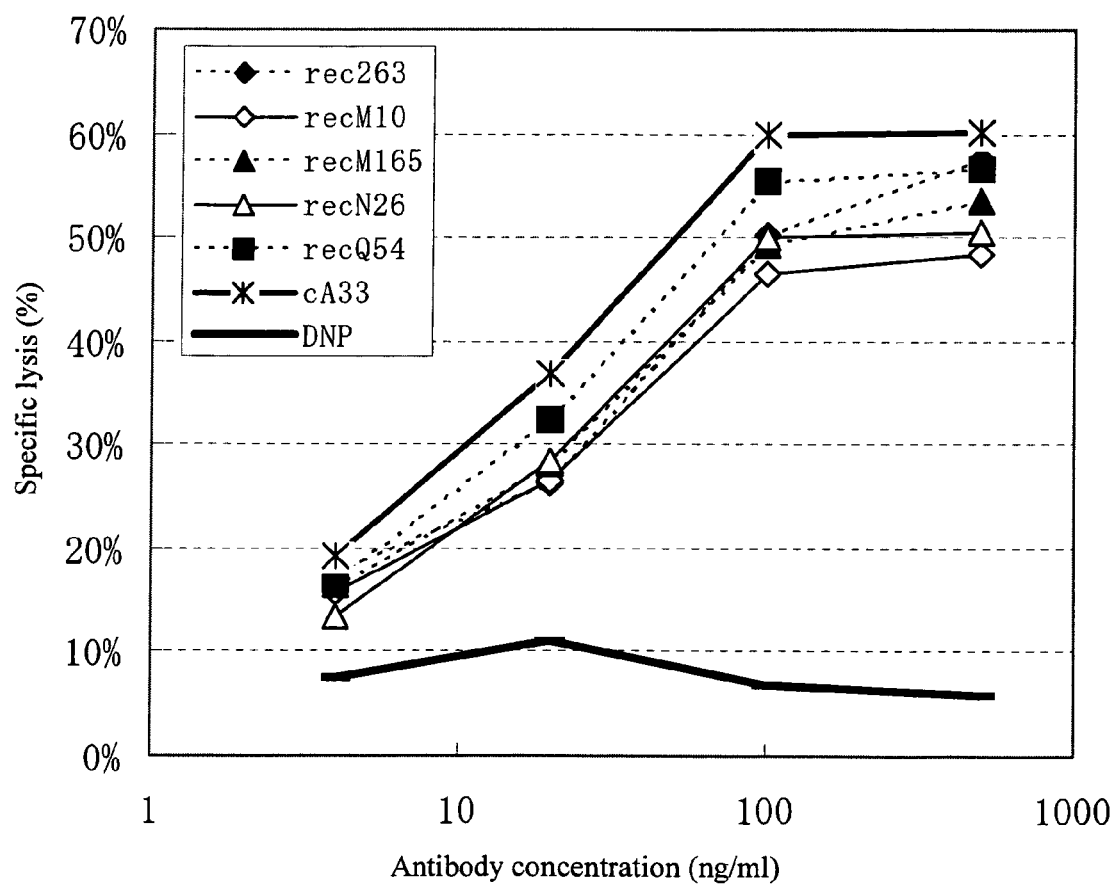
FIG. 2C shows ADCC activity determined when NCI-H508 cells were targeted using recombinant antibodies.
Figure 2D:
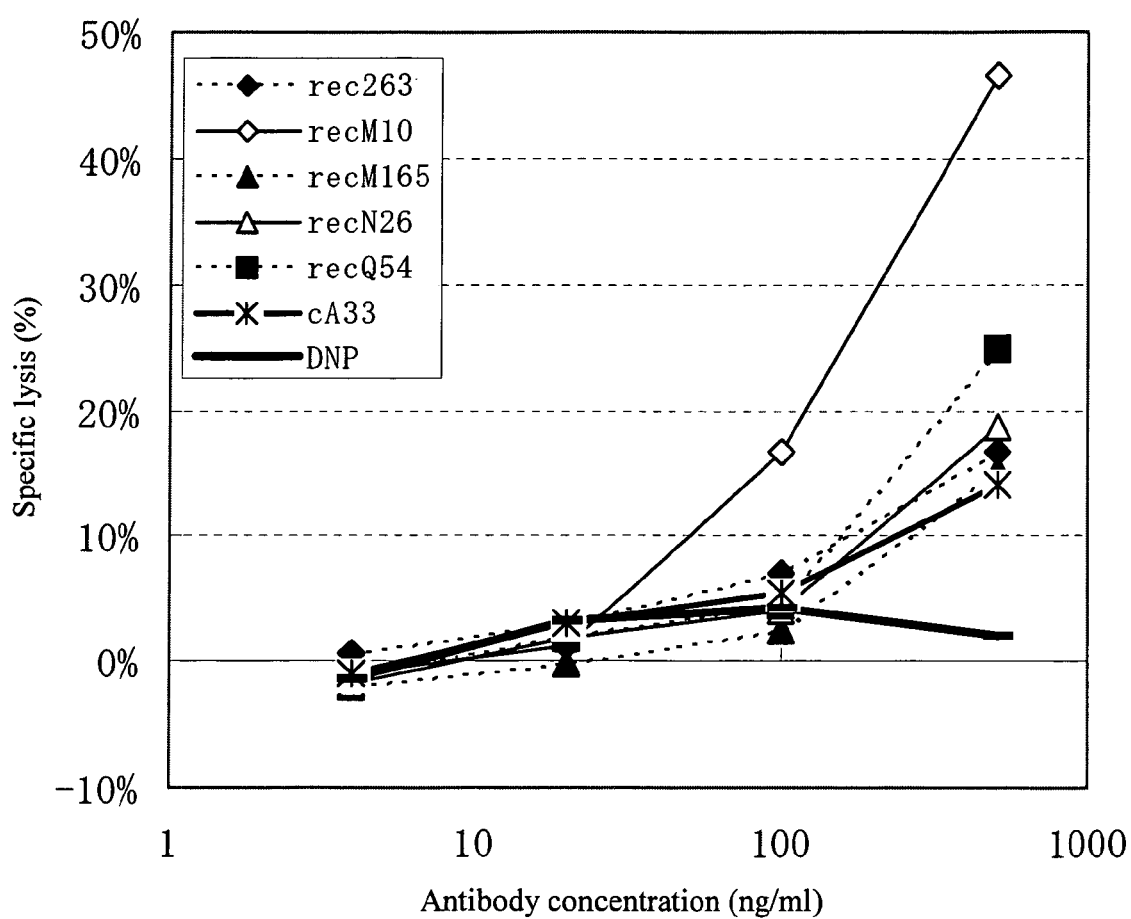
FIG. 2D shows CDC activity determined when NCI-H508 cells were targeted using recombinant antibodies.

Hereafter, the present invention is described in detail.

For A33, a mouse anti-A33 antibody and a humanized anti-A33 antibody have already been obtained. Phase I clinical tests conducted on colon cancer patients using the mouse anti-A33 antibody (see Welt S. et al., J. Clinical Oncology (1994), 12, 1561-1571; Welt S. et al., J. Clinical Oncology (1996), 14, 1787-1797) and the humanized A33 antibody (see Welt S. et al., Clinical Cancer Res. (2003), 9, 1338-1346; Welt S. et al., Clinical Cancer Res. (2003), 9, 1347-1353) have been reported. However, HAMA or HAHA was produced at very high probabilities in patients receiving the antibody, and no further clinical tests were conducted following these. However, very interestingly, no HAHA production was observed in the cases of patients confirmed to have shown tumor reactivity in the clinical test using the humanized anti-A33 antibody.

The novel human anti-A33 monoclonal antibody of the present invention is a complete human antibody. Hence, the antibody of the present invention avoids in advance the problem that always arises upon the use of a mouse antibody or a humanized antibody regarding antigenicity against the portion comprising the mouse sequence. Specifically, in the above clinical test report, HAHA was produced because of the use of the humanized antibody. However, since the novel human anti-A33 monoclonal antibody of the present invention is a complete human antibody, the antigenicity of an antibody can be avoided, and no HAHA is produced. Thus, significant antitumor effects of the antibody can be expected for colon cancer patients.

Examples of antibody classes used herein include immunoglobulin G(IgG), A(IgA), E(IgE), and M(IgM). A preferable antibody class to be used herein is IgG. Furthermore, as an IgG subclass, IgG1, IgG2, IgG3, or IgG4 is used. Preferably, IgG1, IgG2, or IgG4 is used and further preferably, IgG1 is used.

Hereafter, the present invention will be described in detail through clarification of the meanings of terms and phrases used in the present invention.

1. A33 and Anti-A33 Antibody

The antibody of the present invention is a class I cell membrane protein and is an antibody against A33, which is a member of the Ig superfamily.

"Antibody binding to A33" in the present invention refers to an antibody that has reactivity to A33 or a part of A33 or an antibody that recognizes A33 or a part of A33. "Functional fragment" in the present invention refers to a portion (partial fragment) of an antibody, which retains 1 or more actions of an antibody on its corresponding antigen. Specific examples of such fragment include F(ab')$_2$, Fab', Fab, Fv, disulfide-stabilized Fv, single-chain Fv(scFv), and multimers thereof (D. J. King., Applications and Engineering of Monoclonal Antibodies., 1998 T. J. International Ltd). Alternatively, "functional fragment" refers to a fragment of an antibody, which is capable of binding to an antigen.

"Human antibody" in the present invention refers to an antibody that is an expression product of a human-derived antibody gene. As described later, a human antibody can be obtained by introducing a human antibody gene locus and then administering an antigen to a transgenic animal capable of producing a human-derived antibody. An example of such transgenic animal is a mouse. A method for producing such mouse capable of producing a human antibody is described in International Patent Publication WO02/43478, for example.

Examples of the antibody of the present invention include, as described in the following examples, various antibodies that exert antitumor effects against A33-expressing cancer cells, even in low concentrations.

The antibody of the present invention also encompasses a monoclonal antibody comprising a heavy chain and/or light chain having an amino acid sequence derived from the amino acid sequence of a heavy chain or light chain constituting an antibody by deletion, substitution, or addition of 1 or several amino acids. The above-mentioned partial amino acid modification (deletion, substitution, insertion, or addition) can be imparted to the amino acid sequence of the antibody of the present invention by partially modifying the nucleotide sequence encoding the amino acid sequence. Such partial modification of a nucleotide sequence can be imparted by a standard method using known forms of site-specific mutagenesis (Proc Natl Acad Sci U.S.A., 1984 Vol 81: 5662). In addition, an "antibody" in the present invention is an immunoglobulin wherein all regions including the heavy chain variable region and the heavy chain constant region as well as the light chain variable region and the light chain constant region, are derived from a gene encoding an immunoglobulin.

The antibody of the present invention also encompasses an antibody of any immunoglobulin class or isotype.

The anti-A33 antibody of the present invention can be produced by a production method as described below. Specifically, for example, nonhuman mammals such as human-antibody-producing transgenic mice are immunized with A33, a part of A33 or a conjugate of the part of A33 and an appropriate carrier substance (e.g., bovine serum albumin) for enhancing antigenicity together with, if necessary, an immuno-augmenting agent (e.g., Freund's complete or incomplete adjuvant). As A33, both natural A33 and recombinant A33 can be used. Alternatively, immunization can be performed by introducing a gene encoding A33 and then administering animal cells that overexpress A33 on their cell surfaces. A monoclonal antibody can be obtained by fusing antibody-producing cells obtained from immunized animals to myeloma cells incapable of producing any autoantibody, culturing the thus obtained hybridomas, and then selecting clones that produce the monoclonal antibody showing specific affinity for an antigen used for immunization.

The antibody of the present invention also encompasses an antibody, the class of which is converted to a subclass differing from the original subclass by genetic engineering modification (e.g., see EP314161) known by persons skilled in the art. Specifically, an antibody subclass differing from the original antibody subclass can be obtained by a genetic engineering technique using a DNA encoding a variable region of the antibody of the present invention.

ADCC refers to a type of cytotoxicity induced by activation of macrophages, NK cells, neutrophil cells, or the like that are recognized through the binding of antibody constant regions to Fc receptors expressed on the surfaces of the above cells. In contrast, CDC refers to a type of cytotoxicity induced by activation of a complement system that occurs through binding of an antibody to an antigen. It is known that the intensities of these activities vary depending on antibody subclasses. It is also known that such differences are due to structural differences among antibody constant regions (Charles A. Janeway et al., Immunobiology, 1997, Current Biology Ltd/Garland Publishing Inc.). For example, an antibody exhibiting a low degree of binding to Fc receptor can be obtained by converting the antibody subclass of the present invention to IgG2 or IgG4. In contrast, an antibody exhibiting a high degree of binding to Fc receptor can be obtained by converting the antibody subclass of the present invention to IgG1 or IgG3. Furthermore, the degree of binding to Fc receptor can be varied by modifying the amino acid sequence of a constant region of the antibody of the present invention by a genetic engineering technique or the binding of a constant region sequence having such amino acid sequence (see Janeway C A. Jr. and Travers P. (1997), Immunobiology, Third Edition, Current Biology Ltd/Garland Publishing Inc). Alternatively, a degree of binding to a complement can also be varied by the same method (see Mi-Hua Tao, et al. 1993. J. Exp. Med). For example, the degree of binding to a complement can be varied by mutating a sequence CCC (that encodes proline (P) at position 331 (based on the EU numbering system (see Sequences of Proteins of Immunological Interest, NIH Publication No. 91-3242))) of a heavy chain constant portion to TCC encoding serine (S), so as to substitute proline with serine. In the case of an anticancer agent, for example, it is desired that when an antibody alone is unable to exert activity inducing cell death, such antibody have anti-tumor activity based on antibody-dependent cytotoxicity (ADC) or complement-dependent cytotoxicity (CDC) mediated by Fc receptor. It may be more desired when an antibody alone is able to exert activity inducing cell death, such antibody have a low degree of binding to Fc receptor. Furthermore, in the case of an immunosuppressive agent, for example, it is desired that when an antibody three-dimensionally inhibits only the binding of T cells to antigen-presenting cells, such antibody lack ADCC activity or CDC activity. Moreover, when ADCC activity or CDC activity can cause toxicity, an antibody wherein the Fc portion is mutated or the subclass thereof is altered so as to avoid activity that causes toxicity may also be desired.

The present invention encompasses the following steps upon production of monoclonal antibodies: (1) purification of a biopolymer to be used as an immunogen and/or preparation of cells overexpressing an antigen protein on the cell surfaces; (2) immunization of animals by injection of an antigen, collection of blood, determination of the antibody titer, determination of timing for extracting the spleen and the like, and then preparation of antibody-producing cells; (3) preparation of myeloma cells; (4) cell fusion of antibody-producing cells and myeloma cells; (5) selection of a hybridoma group producing a target antibody; (6) division into a single cell clone (cloning); (7) if necessary, culture of the hybridoma for producing the monoclonal antibody in a large amount, or breeding of animals wherein the hybridoma is implanted; and (8) examination of the physiological activity and the recognition specificity of the thus produced monoclonal antibody or determination of the properties of the product as a labeling reagent, for example.

Polymorphisms are present in the case of A33. The antibody of the present invention binds to A33 by recognizing all A33 polymorphisms that are currently known. Regardless of differences of A33 polymorphisms among patients, a therapeutic or preventive agent containing the antibody of the present invention can act effectively.

Hereinafter, a method for preparing an anti-A33 monoclonal antibody will be described in detail based on the above steps. However, such method for preparing the antibody is not limited to the following methods. For example, antibody-producing cells and myeloma cells other than splenocytes can also be used.

(1) Purification of Antigen

Transformed cell lines are prepared by incorporating a DNA encoding A33 into an expression vector for animal cells and then introducing the expression vector into animal cells. The thus obtained transformed cell line can be directly used as an antigen. Furthermore, since the primary structure of A33 protein is known (GenBank accession No. NP_005305, SEQ ID NO: 12), a peptide is chemically synthesized from the amino acid sequence of A33 by a method known by persons skilled in the art, following which the product can also be used as an antigen.

Furthermore, cells overexpressing A33 on their cell surfaces can also be effective as immunogens, which are prepared by introducing full-length A33 into FM3A cells or L929 cells. pΔEGFP-N1-A33 can be prepared by incorporating a DNA encoding the A33 protein into an expression vector pΔEGFP-N1 for animal cells (where a region encoding an EGFP protein of modified pEGFP-N1 (produced by Becton Dickinson Bioscience Clontech) is deleted). However, such DNA encoding A33, vector, host, and the like are not limited to these examples.

Specifically, a transformed cell line is obtained by transforming FM3A cells or L929 cells with pΔEGFP-N1-A33, followed by culturing. The trait of neomycin resistance acquired by cells into which pΔEGFP-N1 vectors are inserted is confirmed, and the expression of A33 is also confirmed using a mouse anti-human A33 antibody (ATCC No.

HB-8779). Hence, FM3A cells or L929 cells overexpressing A33 on the cell surfaces can be prepared using such confirmation results as indices.

(2) Step for Preparing Antibody-producing Cells

The antigen obtained in (1) is mixed with Freund's complete or incomplete adjuvant or an adjuvant such as potassium aluminum sulfate. Experimental animals are immunized with the thus obtained mixture as an immunogen. As experimental animals, transgenic mice capable of producing a human-derived antibody are most suitably used. Such mice are described in document of Tomizuka et al (Tomizuka. et al., Proc Natl Acad Sci U.S.A., 2000 Vol 97: 722).

The route of administration of an immunogen upon immunization of mice may be subcutaneous injection, intraperitoneal injection, intravenous injection, intracutaneous injection, intramuscular injection, footpad injection, or the like. Intraperitoneal injection, footpad injection, or intravenous injection is preferred.

Immunization can be performed once or several times repeatedly at appropriate intervals (preferably at 2-week to 4-week intervals). Subsequently, antibody titers against the antigen in the sera of immunized animals are determined. The effects of the subsequent procedures can be increased with the use of an animal with a sufficiently elevated antibody titer as a supply source of antibody-producing cells. In general, it is preferable to use antibody-producing cells derived from an animal 3 to 5 days after final immunization for subsequent cell fusion.

Examples of methods for determining antibody titers that may be employed herein include various known techniques such as a radioimmunoassay method (hereinafter referred to as the "RIA method"), an enzyme-linked immunosorbent assay method (hereinafter referred to as the "ELISA method"), a fluorescence antibody method, and a passive haemagglutination method. In view of detection sensitivity, rapidity, accuracy, possible automation of procedures, and the like, the RIA method or the ELISA method is more suitable.

Antibody titer can be determined in the present invention by procedures described below, when the ELISA method is employed, for example. First, an antigen against a human antibody is adsorbed on the solid phase surface of a 96-well plate for ELISA or the like. Furthermore, some areas on the solid phase surface at which the antigen is not adsorbed are covered with a protein independent of the antigen (e.g., bovine serum albumin (BSA)). After the surface is washed, the surface is caused to come into contact with a sample (e.g., mouse serum) serially diluted as a primary antibody. An anti-A33 antibody in a sample is caused to bind to the above antigen. An enzyme-labeled secondary antibody against a human antibody is added to bind to the human antibody. After washing, the substrate of the enzyme is added. Antibody titer is calculated through determination of changes or the like in absorbance due to color development based on substrate degradation.

(3) Step for Preparing Myeloma Cells

As myeloma cells, cells incapable of producing any autoantibody derived from mammals such as a mouse, rat, guinea pig, hamster, rabbit, or human can be used. In general, it is preferable to use established cell lines obtained from mice, such as 8-azaguanine-resistant mouse (derived from BALB/c) myeloma cell lines P3X63Ag8U.1 (P3-U1) (Yelton, D. E. et al. Current Topics in Microbiology and Immunology, 81, 1-7 (1978)), P3/NSI/1-Ag4-1 (NS-1) (Kohler, G. et al. European J. Immunology, 6, 511-519 (1976)), Sp2/O-Ag14 (SP-2) (Shulman, M. et al., Nature, 276, 269-270 (1978)), P3X63Ag8.653 (653) (Kearney, J. F. et al., J. Immunology, 123, 1548-1550 (1979)), and P3X63Ag8 (X63) (Horibata, K. and Harris, A. W. Nature, 256, 495-497 (1975)). These cell lines are sub-cultured in appropriate medium such as 8-azaguanine medium (prepared by adding 8-azaguanine to RPMI-1640 medium supplemented with glutamine, 2-mercaptoethanol, gentamicin, and fetal calf serum (hereinafter referred to as "FCS")), Iscove's Modified Dulbecco's Medium (hereinafter, referred to as "IMDM"), or Dulbecco's Modified Eagle Medium (hereinafter, referred to as "DMEM"). 3 to 4 days before cell fusion, the cell lines are sub-cultured in normal medium (e.g., DMEM medium containing 10% FCS). On the day of cell fusion, $2 \times 10^7$ or more cells are maintained.

(4) Cell Fusion

Antibody-producing cells are plasma cells and the lymphocytes that are the precursor cells thereof. Antibody-producing cells may be obtained from any sites of an individual body and can be obtained generally from the spleen, lymph nodes, bone marrow, tonsil, or peripheral blood, an appropriate combination thereof, or the like. Splenocytes are most generally used.

After final immunization, a site at which antibody-producing cells are present, such as the spleen, is excised from a mouse for which a predetermined antibody titer has been obtained, so that splenocytes, which are antibody-producing cells, are prepared. Next, the splenocytes are fused to myeloma cells. Currently, the most generally conducted means for fusing such splenocytes to myeloma cells obtained in step (3) is a method using polyethylene glycol, which is characterized by relatively low cytotoxicity and simple procedures for cell fusion. This method comprises the following procedures, for example.

Splenocytes and myeloma cells are washed well with serum-free culture medium (e.g., DMEM) or phosphate buffered saline (hereinafter, referred to as PBS), mixed until the ratio of the number of cells of splenocytes to myeloma cells reaches approximately 5:1 to 10:1, and then subjected to centrifugation. The supernatant is removed and then precipitated cell groups are loosened well. 1 mL of serum-free culture medium containing 50% (w/v) polyethylene glycol (with a molecular weight between 1000 and 4000) is added dropwise while agitating the solution. Subsequently, 10 mL of serum-free culture medium is gently added, followed by centrifugation. The supernatant is discarded again. The precipitated cells are suspended in normal medium (hereinafter, referred to as HAT medium) containing an appropriate amount of a hypoxanthine-aminopterin-thymidine (hereinafter, referred to as HAT) solution and human interleukin-6 (hereinafter, referred to as IL-6). The suspension is dispensed to each well of a culture plate (hereinafter, referred to as plate), followed by approximately 2 weeks of culture in the presence of 5% carbonic acid gas at 37° C. During the culture period, HAT medium is appropriately supplemented.

(5) Selection of Hybridoma Groups

When the above myeloma cells are of a 8-azaguanine-resistant cell line, and more specifically, of a hypoxanthine guanine phosphoribosyltransferase (HGPRT)-deficient cell line, non-fused myeloma cells and the fusion cells of multiple myeloma cells are unable to survive in medium containing HAT. On the other hand, fusion cells of multiple antibody-producing cells or hybridomas of antibody-producing cells and myeloma cells can survive. However, such fusion cells of multiple antibody-producing cells have limited lifetime. Accordingly, through continuation of culture in medium containing HAT, only hybridomas that are the fusion cells of antibody-producing cells and myeloma cells survive. As a result, such hybridomas can be selected.

For hybridomas that grow in the form of colonies, HAT medium is exchanged with medium from which aminopterin is excluded (hereinafter, referred to as HT medium). Subsequently, a portion of the culture supernatant is collected and then anti-A33 antibody titer is determined by the ELISA method, for example. However, when the above fusion protein is used as an antigen for ELISA, clones that produce an antibody specifically binding to the Fc region of human IgG should be eliminated so as to avoid selection of such clones. The presence or the absence of such clones can be confirmed by ELISA or the like using the Fc region of human IgG as an antigen.

As described above, the method using the 8-azaguanine-resistant cell line is described as an example. Other cell lines can also be used, depending on the method used for selecting a hybridoma, and the composition of medium to be used in such a case will vary.

(6) Cloning Step

Hybridomas that are revealed to produce a specific antibody as a result of determination of antibody titers by a method similar to the method described in (2) are transferred to another plate, followed by cloning. Examples of a cloning method to be used herein include a limiting dilution method that involves performing dilution so that each well of a plate then contains one hybridoma, and culturing the hybridomas; a soft agar method that involves culturing in soft agar medium and then harvesting colonies, a method that involves extracting each cell using a micromanipulator and then culturing each cell; and a "sorter clone" method that involves separating cells one-by-one with the use of a cell sorter. The limiting dilution method is convenient and is often used.

For wells for which antibody titers are observed, cloning is repeated 2 to 4 times by a limiting dilution method, for example. Cells for which antibody titers are stably observed are selected as cells of the hybridoma line producing the anti-A33 monoclonal antibody.

In addition, mouse-mouse hybridomas that are the human anti-A33 monoclonal antibody-producing cells of the present invention-125M10AA, 125M165DAAA, 125M96ABA, 125N26F6AA, 125Q47BA, 125Q54AAAA, and 125R5AAAA—were deposited on Aug. 24, 2004, with the International Patent Organism Depositary (IPOD) (Central 6, 1-1, Higashi 1, Tsukuba, Ibaraki, Japan), National Institute of Advanced Industrial Science and Technology (AIST), under accession Nos. FERM BP-10107 (denotation for identification: M10), FERM BP-10106 (denotation for identification: M165), FERM BP-10108 (denotation for identification: M96), FERM BP-10109 (denotation for identification: N26), FERM BP-10104 (denotation for identification: Q47), FERM BP-10105 (denotation for identification: Q54), and FERM BP-10103 (denotation for identification: R5), respectively.

(7) Preparation of Monoclonal Antibodies by Culture of Hybridomas

After completion of cloning, HT medium is exchanged with normal medium and then hybridomas are cultured. Large-scale culture is performed by rotation culture using large culture bottle, spinner culture, or culture using a hollow fiber system or the like. The supernatant obtained by such large-scale culture is purified by a method known by persons skilled in the art, such as gel filtration, so that the anti-A33 monoclonal antibody can be obtained. Furthermore, the hybridomas are proliferated intraperitoneally in mice (e.g., BALB/c) of the same line or nu/nu mice, rats, guinea pigs, hamsters, rabbits, or the like, so that ascites containing the anti-A33 monoclonal antibody in large amounts can be obtained. As a convenient method for purification, a commercial monoclonal antibody purification kit (e.g., a MAbTrap GII kit; produced by Amersham Pharmacia Biotech) or the like can also be used.

The thus obtained monoclonal antibody has high antigen specificity against A33.

(8) Determination of Monoclonal Antibody

The isotype and subclass of the thus obtained monoclonal antibody can be determined as follows. Examples of an identification method include an Ouchterlony method, an ELISA method, and an RIA method. The Ouchterlony method is convenient, but requires a procedure for condensing the concentration of a monoclonal antibody when the concentration is low. In the meantime, when the ELISA method or the RIA method is used, the culture supernatant is directly caused to react with antigen-adsorbed solid phase. The isotype and the subclass of a monoclonal antibody can then be identified using antibodies corresponding to various immunoglobulin isotypes and subclasses as secondary antibodies.

Furthermore, protein determination can be performed by a Folin-Lowry method, which is a method that involves calculation based on absorbance at 280 nm (1.4 (OD 280)=immunoglobulin (1 mg/mL)).

Identification of an epitope that is recognized by a monoclonal antibody can be performed as described below. First, various partial structures of molecules that a monoclonal antibody recognizes are prepared. Examples of a method for preparing such partial structures include: a method by which various partial peptides of a molecule are prepared using a known oligopeptide synthesis technique; and a method by which a DNA sequence encoding a target partial peptide is incorporated into a suitable expression plasmid using a gene recombination technique and then the peptide is produced within or outside a host such as *Escherichia coli*. In general, both methods are used in combination for the above purpose. For example, a series of polypeptides are prepared through sequential shortening of the C-terminus or the N-terminus of an antigen protein by appropriate lengths using a gene recombination technique known by persons skilled in the art. The reactivity of a monoclonal antibody against each of these polypeptides is examined, so that a rough recognition site is determined.

Various oligopeptides corresponding to such sites, variants of such peptides, and the like are further subsequently synthesized using an oligopeptide synthesis technique known by persons skilled in the art. An epitope is determined through examination of the binding of a monoclonal antibody (contained as an active ingredient in a preventive or therapeutic agent of the present invention) to such peptides or through examination of the competitive inhibition activity of a peptide against the binding of such monoclonal antibody to an antigen. As a convenient method for obtaining various types of oligopeptides, commercial kits (e.g., SPOTs kit (produced by GenoSys Biotechnology) and a series of multipin peptide synthesis kits (produced by Chiron Corporation) using a multipin synthesis method) can be used.

Furthermore, a gene encoding a human monoclonal antibody is cloned from antibody-producing cells such as hybridomas, and then the gene is incorporated into an appropriate vector. The vector is then introduced into a host (e.g., mammalian cell lines, *Escherichia coli*, yeast cells, insect cells, and plant cells). Hence, a recombinant antibody produced using a gene recombination technique can also be prepared (P. J. Delves., Antibody Production Essential Techniques., 1997 Wiley, P. Shepherd, and C. Dean., Monoclonal Antibodies, 2000 Oxford University Press, J. W. Goding., Monoclonal Antibodies: Principles and Practice, 1993 Academic Press).

The present invention also encompasses nucleic acids containing the gene sequences of the antibodies of the present invention, which are possessed by hybridomas producing the antibodies. In particular, it also encompasses the nucleic acids of the heavy chain variable regions and the light chain variable regions of the antibodies produced by the hybridomas of the present invention described later. "Nucleic acid(s)" used herein include DNA and RNA.

A method employed for preparation of a gene encoding a monoclonal antibody from a hybridoma involves preparing DNAs encoding monoclonal antibody L chain V region, L chain C region, H chain V region, and H chain C region by the PCR method, or the like. As primers, oligo DNAs designed from the anti-A33 antibody gene or the amino acid sequence thereof can be used. As a template, a DNA prepared from a hybridoma can be used. These DNAs are incorporated into one appropriate vector, and then the vector is introduced into a host for expression. Alternatively, these DNAs are separately incorporated into appropriate vectors, followed by co-expression of the DNAs.

As a vector, a phage or a plasmid that is autonomously replicable in host microorganisms is used. Examples of a plasmid DNA include plasmids derived from *Escherichia coli*, *Bacillus subtilis*, or yeast, while the phage DNA may be λ phage.

Hosts that are used for transformation are not particularly limited as long as they can express a target gene. Examples of such hosts include bacteria (e.g., *Escherichia coli* and *Bacillus subtilis*), yeast, animal cells (e.g., COS cells and CHO cells), and insect cells.

Methods for introducing genes into hosts are known. Examples of such methods include arbitrary methods such as a method using calcium ions, an electroporation method, a spheroplast method, a lithium acetate method, a calcium phosphate method, and a lipofection method. In addition, examples of a method for introducing genes into animals described later include a microinjection method, a method by which genes are introduced into ES cells using the electroporation or lipofection method, and a nuclear transplantation method.

In the present invention, the anti-A33 antibody can be obtained by culturing a transformant and then harvesting the antibody from the culture product. "Culture product(s)" refers to (a) culture supernatant, (b) cultured cells, cultured microbial bodies or disrupted products thereof, or (c) secretion products of the transformant. To culture a transformant, medium appropriate for a host is used and a static culture method, a roller bottle culture method, or the like is employed.

After culture, when a target antibody protein is produced within microbial bodies or cells, the antibody is harvested by disrupting the microbial bodies or cells. In addition, when a target antibody is produced out of microbial bodies or cells, the culture solution is used intact, or microbial bodies or cells are removed by centrifugation or the like. Thereafter, a target antibody can be isolated and purified from the culture product by a single general biochemical method or an appropriate combination of such biochemical methods using various types of chromatography, which are used for protein isolation and purification.

Furthermore, a technique for producing transgenic animals is used to produce an animal host wherein the gene of a target antibody is incorporated in an endogenous gene, such as transgenic cattle, transgenic goats, transgenic sheep, or transgenic pigs. A monoclonal antibody derived from the antibody gene can also be obtained in large amounts from milk secreted from such transgenic animals (Wright, G., et al., (1991) Bio/Technology 9, 830-834). When a hybridoma is cultured in vitro, the hybridoma is proliferated, maintained, and stored in accordance with various conditions, including the properties of cell types to be cultured, the purposes of experiment and research, culture methods, and the like. Such culture can be performed using known nutrition medium that is used for production of a monoclonal antibody in culture supernatant or all types of nutrition medium induced and prepared from known basic medium.

(9) Antibody Properties

The antibody of the present invention has one of the following properties.

(a) ADCC Test

In the presence of normal human peripheral blood mononuclear cells, the antibody of the present invention exerts antibody-dependent cellular cytotoxicity (ADC) against A33-expressing human cancer cells.

(b) CDC Test

In the presence of human serum-derived complements, the antibody of the present invention exerts complement-dependent cytotoxicity (CDC) against A33-expressing human cancer cells.

(c) In vivo Test

The antibody of the present invention exerts antitumor effects against non-human animals bearing A33-expressing human cancer cells.

(d) Competition Test

The antibody of the present invention is (i) strongly competitive (blocker), (ii) weakly competitive (partial blocker), or (iii) not competitive (non-blocker) with chimeric anti-A33 (comprising the heavy chain variable region and the light chain variable region of an antibody produced by hybridoma ATCC HB-8779 and the heavy chain constant region and the light chain constant region of human IgG1).

(e) Immunohistochemical Test

The antibody of the present invention results in the staining of human adult colon cancer tissues, human adult normal colon tissues, and human normal small intestine tissues.

Examples of such antibodies include antibodies produced by hybridomas 263A17, 125M10AA, 125M165DAAA, 125M96ABA, 125N26F6AA, 125Q47BA, 125Q54AAAA, and 125R5AAAA, for example. 125M10AA, 125M165DAAA, 125M96ABA, 125N26F6AA, 125Q47BA, 125Q54AAAA, and 125R5AAAA were deposited on Aug. 24, 2004 with the International Patent Organism Depositary (IPOD) (Central 6, 1-1, Higashi 1, Tsukuba, Ibaraki, Japan), the National Institute of Advanced Industrial Science and Technology (AIST) under accession Nos. FERM BP-10107 (denotation for identification: M10), FERM BP-10106 (denotation for identification: M165), FERM BP-10108 (denotation for identification: M96), FERM BP-10109 (denotation for identification: N26), FERM BP-10104 (denotation for identification: Q47), FERM BP-10105 (denotation for identification: Q54), and FERM BP-10103 (denotation for identification: R5), respectively.

2. Pharmaceutical Compositions

A pharmaceutical composition containing the human anti-A33 antibody of the present invention is also within the scope of the present invention. Such formulation preferably contains a physiologically acceptable diluent or carrier in addition to the antibody, and may be a mixture thereof with a different antibody or a different drug such as an antibiotic agent. Examples of an appropriate carrier include, but are not limited to, physiological saline, phosphate buffered physiological saline, a phosphate buffered physiological saline glucose solution, and buffered physiological saline. Alternatively, the antibody may be freeze-dried and, when needed, reconstituted by the addition of an aqueous buffer as described above. Such preventive or therapeutic agent can be administered through various routes for administration. Examples of such routes for administration include oral administration with the use of tablets, capsules, granules, powders, syrups, or the like and parenteral administration with the use of injections, drops, suppositories, or the like.

The dose of such pharmaceutical composition differs depending on symptom, age, body weight, and the like. Generally, in the case of oral administration, a dose ranging from approximately 0.01 mg to 1000 mg per day for an adult and can be administered once or several separate times. In the case of parenteral administration, a dose ranging from approximately 0.01 mg to 1000 mg per administration can be administered via subcutaneous injection, intramuscular injection, or intravenous injection.

The present invention also encompasses the above method for preventing or treating diseases using the antibody or the pharmaceutical composition of the present invention. Furthermore, the present invention also encompasses the use of the antibody of the present invention for production of the above preventive or therapeutic agent for diseases.

Tumors that can be prevented or treated with the use of the antibody or a functional fragment thereof of the present invention are colorectal cancer, colon cancer, rectal cancer, gastric cancer, pancreatic cancer, breast cancer, melanoma, renal cell cancer, cervical cancer, endometrial cancer, ovarian cancer, esophageal cancer, prostatic cancer, testicular cancer, mesothelial cancer, and the like. The number of tumor type to which the antibody of the present invention is applied is not limited to a single type. The antibody can also be applied to a case where tumors of a plurality of types are developed simultaneously.

3. PHARMACEUTICAL PREPARATION EXAMPLES

The molecule of the present invention can be used as an ampule of a sterile solution or a suspension prepared by dissolving the molecule in water or a pharmacologically acceptable solution other than water. Moreover, such ampule is filled with a sterile powdery pharmaceutical preparation (preferably, the molecule of the present invention is freeze-dried) and then the ampule may be diluted with a pharmacologically acceptable solution when it is used.

The present invention will be described in more detail below with reference to examples. However, the present invention is not limited to embodiments described in the examples.

EXAMPLE 1

Preparation of Mouse Anti-A33 Antibody

A mouse anti-A33 antibody was prepared for use as a positive control antibody in screening for hybridomas producing human monoclonal antibodies and various experiments. An AS33 hybridoma (American Type Culture Collection (ATCC) No. HB-8779) producing the mouse anti-A33 antibody was purchased from ATCC. The hybridoma was cultured according to instructions included in the ATCC product. The hybridoma was freeze-dried. Subsequently, the AS33 hybridoma was acclimatized in eRDF medium (produced by Kyokuto Pharmaceutical Industrial) containing 10% Low IgG Fetal Bovine Serum (produced by HyClone). The acclimatized hybridoma was cryopreserved. Next, for the purpose of antibody purification, a part of the cryopreserved product was acclimatized in eRDF medium (produced by Kyokuto Pharmaceutical Industrial) containing cattle insulin (5 μg/ml, produced by Gibco BRL), human transferrin (5 μg/ml, produced by Gibco BRL), ethanolamine (0.01 mM, produced by Sigma), sodium selenite ($2.5 \times 10^{-5}$ mM, produced by Sigma), and 1% Low IgG Fetal Bovine Serum (produced by HyClone). After culture in a flask, the culture supernatant was collected. The concentration of the purified antibody derived from the hybridoma in the collected supernatant was obtained by measurement of absorbance at 280 nm and calculation with 1.4 OD being equivalent to 1 mg/mL (antibody concentration).

EXAMPLE 2

Preparation of Chimeric Anti-A33 Antibody

A chimeric anti-A33 antibody having human IgG1 heavy chain and human IgG1 light chain constant regions was prepared as a positive control antibody for use in screening for hybridomas producing human monoclonal antibodies or various experiments.

(1) cDNA Cloning of Chimeric Anti-A33 Antibody Gene and Construction of Expression Vector The hybridoma AS33 producing the mouse anti-A33 antibody purchased in Example 1 was cultured in DMEM medium (produced by Gibco BRL) containing 10% Fetal Bovine Serum (produced by HyClone), and then total RNA was purified using an RNA extraction reagent ISOGEN (produced by NIPPON GENE) according to the relevant protocols. Next, polyA+RNA was purified from the total RNA using Oligotex™-dT30 <Super> (produced by TAKARA BIO). Cloning experiments were conducted using the thus obtained polyA+RNA (2.5 μg) as a material and a SMART RACE cDNA Amplification Kit (Becton Dickinson Bioscience Clontech) according to the instructions included therein. The cDNA of a variable region of the antibody gene was thus obtained.

1) Synthesis of 1st Strand cDNA

| | |
|---|---|
| polyA + RNA | (2.5 μg)/3 μl |
| 5'-CDS primer | 1 μl |
| SMART II A oligo | 1 μl |

A reaction solution having the above composition was subjected to 2 minutes of incubation at 70° C. The following reagents and enzymes were added, and then incubation was performed for 1.5 hours at 42° C., followed by cDNA synthesis.

| | |
|---|---|
| 5X First-Strand buffer | 2 μl |
| DTT (20 mM) | 1 μl |
| dNTP Mix (10 mM) | 1 μl |
| PowerScript Reverse Transcriptase | 1 μl |

After completion of the reaction, 100 μl of Tricine Buffer was added and then incubation was performed at 72° C. for 7 minutes.

2) Amplification of Heavy Chain and Light Chain Genes by PCR

The thus obtained cDNA was used as a template for PCR. A primer set used for PCR was composed of: the PCR primer (for H chain: GPAHvR3Nhe (5'-GCC CTT GGT GCT AGC TGA AGA GAC GGT GAC CAG AGT CCC TTG-3') (SEQ ID NO: 1) or for L chain: GPALvR3Bsi (5'-GTG CAC GCC GCT GGT CAG GGC GCC TG-3') (SEQ ID NO: 2)) specific to the 3' terminus of the mouse anti-A33 antibody heavy chain (hereinafter, a "heavy chain" may also be referred to as an "H chain") variable region DNA or the 3' terminus of the mouse anti-A33 antibody light chain (hereinafter, a "light chain" may also be referred to as an "L chain") variable region DNA; and a UPM primer (oligonucleotide complementary to the common sequence, which is prepared at the 5' terminus of the synthesized cDNA) included in a SMART RACE cDNA Amplification Kit. The H chain leader sequence and variable region (hereinafter, also referred to as "HV") were amplified by PCR. Further, the L chain leader sequence and variable region (hereinafter, also referred to as "LV") were amplified by PCR. cDNA amplification was performed using KOD-Plus-DNA polymerase (produced by TOYOBO), and the following reaction solution was prepared.

| | |
|---|---|
| Sterile H$_2$O | 29.5 µl |
| cDNA | 2.5 µl |
| KOD-Plus-buffer (10X) | 5 µl |
| dNTP Mix (2 mM) | 4 µl |
| MgSO$_4$ (25 mM) | 2 µl |
| KOD-Plus-DNA polymerase (1 unit/µl) | 1 µl |
| Universal primer A mix (UPM) (10X) | 5 µl |
| Gene specific primers (GSP) | 1 µl |
| Total volume | 50 µl |

A thermal cycling amplification reaction was performed under the following conditions.

5 cycles:
 94° C. for 30 sec
 72° C. for 1 min 5 cycles:
 94° C. for 30 sec
 70° C. for 30 sec
 72° C. for 1 min 25 cycles:
 94° C. for 30 sec
 68° C. for 30 sec
 72° C. for 1 min The thus amplified PCR fragments were harvested by ethanol precipitation, harvested by agarose gel electrophoresis, and then purified using a QIAquick Gel Extraction Kit (produced by QIAGEN), which is a DNA purification kit using a membrane. The thus purified HV and LV amplified fragments were separately subcloned into a PCR 4 Blunt-TOPO vector of a Zero Blunt TOPO PCR Cloning Kit (produced by Invitrogen). The nucleotide sequences of the insert DNAs were analyzed for the plasmid DNAs of the thus obtained clones. For determination of the DNA nucleotide sequences, M13FW (5'-GTA AAA CGA CGG CCA GTG-3') (SEQ ID NO: 3) and M13RV (5'-CAG GAA ACA GCT ATG AC-3') (SEQ ID NO: 4) were used as primers. The antibody amino acid sequences encoded by the thus determined HV and LV gene regions completely matched the amino acid sequences of the mouse anti-A33 antibody (Br J Cancer. 1995 December 72 (6): 1364-72) variable regions reported by King D. J. et al.

(3) Construction of Expression Vector (N5KG1_mVhCA33) for Chimeric Anti-A33 Antibody The mouse anti-A33 antibody HV was amplified by PCR (94° C. for 3 minutes→94° C. for 10 seconds and 68° C. for 45 seconds (35 cycles)→72° C. for 7 minutes) using a plasmid DNA containing the thus obtained antibody HV chain as a template and primers (of a primer set for amplification: GPAHv2F5Sal (5'-AGA GAG AGG TCG ACC CAC CAT GAA CTT GGC TGA GCT TAG TT-3') (SEQ ID NO: 5) and GPAHvR3Nhe (SEQ ID NO: 1)) designed to add restriction enzyme sites to the termini for ligation. The amplified HV fragments were purified, and then subcloning was performed into PCR 4 Blunt-TOPO vectors. The DNA nucleotide sequence of the inserted portion was analyzed for the subclones. Thus, plasmid DNAs each having a sequence designed not to differ from the gene sequence used as a template were selected. The plasmid DNAs were digested with restriction enzymes Sal I and Nhe I. An approximately 440-bp DNA was harvested and purified by agarose gel electrophoresis. In the meantime, an N5KG1-Val Lark vector (a modified vector of IDEC Pharmaceuticals, N5KG1 (U.S. Pat. No. 6,001,358)) was similarly treated with restriction enzymes Sal I and Nhe I and then subjected to dephosphorylation using alkaline phosphatase (E. coli C75) (produced by TAKARA BIO). Subsequently, an approximately 8.9-kb DNA was harvested by agarose gel electrophoresis and a DNA purification kit. These two fragments were subjected to a ligation reaction using a DNA ligation kit Ver 2.1 (produced by TAKARA BIO) and then introduced into Escherichia coli DH5α, thereby obtaining transformants. Through screening of the transformants, a clone N5KG1_GPA33Hv (clone #2), into which the target HV had been inserted, was selected. For insertion of LV into the thus obtained N5KG1_GPA33Hv, the plasmid DNA was cleaved sequentially with restriction enzymes Bgl II and BsiW I and then subjected to dephosphorylation. A vector DNA of approximately 9.2 kb was then purified. Meanwhile, the LV region was amplified by PCR using a plasmid DNA containing the mouse anti-A33 antibody LV as a template. GPALv2FBgl (5'-AGA GAG AGA GAT CTC TCA CCA TGG GCA TCA AGA TGG AGT TTC AG-3') (SEQ ID NO: 6) and GPALvR3Bsi (SEQ ID NO: 2) were used as a primer set for amplification. The thus purified and amplified LV fragments were subcloned into PCR 4 Blunt-TOPO. The DNA nucleotide sequence of the inserted portion was analyzed for the subclones. Thus, plasmid DNAs each having a sequence designed not to differ from the gene sequence used as a template were selected. The DNAs were digested with restriction enzymes Bgl II and BsiW I. An approximately 400-bp DNA was then harvested and purified by agarose gel electrophoresis. The DNA was ligated to the above N5KG1_A33Hv vector fragment that had been cleaved with restriction enzymes Bgl II and BsiW I, and was then introduced into Escherichia coli, thereby obtaining transformants. Through screening of the transformants, a clone N5KG1_GPA33HvLv (clone #2), into which the target LV had been inserted, was selected. The finally obtained chimeric anti-A33 antibody expression plasmid DNA was purified in a large quantity. Thus, it was confirmed that no mutations had occurred in the inserted L chain or H chain DNA fragments, or in the DNA nucleotide sequences of the peripheries of the insertion sites.

DNAs encoding the chimeric anti-A33 heavy chain variable region and the light chain variable region and the amino acid sequences of the heavy chain variable region and the light chain variable region are each shown below.

<Chimeric anti-A33 heavy chain nucleic acid sequence> (SEQ ID NO: 7)
```
        10         20         30         40         50         60
ATGAACTTTG GGCTGAGCTT GATTTTCCTT GTCCTAATTT TAAAAGGTGT CCAGTGTGAA 70         80         90        100        110        120
GTGAAGCTGG TGGAGTCTGG GGGAGGCTTA GTGAAGCCTG GAGGGTCCCT GAAACTCTCC 130        140        150        160        170        180
TGTGCAGCCT CTGGATTCGC TTTCAGTACC TATGACATGT CTTGGGTTCG CCAGACTCCG 190        200        210        220        230        240
GAGAAGAGGC TGGAGTGGGT CGCAACCATT AGTAGTGGTG GTAGTTACAC CTACTATTTA 250        260        270        280        290        300
GACAGTGTGA AGGGCCGATT CACCATCTCC AGAGACAGTG CCAGGAACAC CCTATACCTG 310        320        330        340        350        360
CAAATGAGCA GTCTGAGGTC TGAGGACACG GCCTTGTATT ACTGTGCACC GACTACGGTA 370        380        390        400        410        420
GTCCCGTTTG CTTACTGGGG CCAAGGGACT CTGGTCACCG TCTCTTCAGC TAGC......
```

<Chimeric anti-A33 heavy chain amino acid sequence> (SEQ ID NO: 8)
```
        10         20         30         40         50         60
MNFGLSLIFL VLILKGVQCE VKLVESGGGL VKPGGSLKLS CAASGFAFST YDMSWVRQTP 70         80         90        100        110        120
EKRLEWVATI SSGGSYTYYL DSVKGRFTIS RDSARNTLYL QMSSLRSEDT ALYYCAPTTV 130        140
VPFAYWGQGT LVTVSSAS..
```

>Chimeric anti-A33 light chain nucleic acid sequence> (SEQ ID NO: 9)
```
        10         20         30         40         50         60
ATGGGCATCA AGATGGAGTT TCAGACCCAG GTCTTTGTAT TCGTGTTGCT CTGGTTGTCT 70         80         90        100        110        120
GGTGTTGATG GAGACATTGT GATGACCCAG TCTCAAAAAT TCATGTCCAC ATCAGTAGGA 130        140        150        160        170        180
GACAGGGTCA GCATCACCTG CAAGGCCAGT CAGAATGTTC GTACTGTTGT AGCCTGGTAT 190        200        210        220        230        240
CAACAGAAAC CAGGGCAGTC TCCTAAAACA CTGATTTACT TGGCCTCCAA CCGGCACACT 250        260        270        280        290        300
GGAGTCCCTG ATCGCTTCAC AGGCAGTGGA TCTGGGACAG ATTTCACTCT CACCATTAGC 310        320        330        340        350        360
AATGTGCAAT CTGAAGACCT GGCAGATTAT TTCTGTCTGC AACATTGGAG TTATCCTCTC 370        380        390        400
ACGTTCGGCT CGGGGACAAA GTTGGAAGTA AAACGT....
```

<Chimeric anti-A33 light chain amino acid sequence> (SEQ ID NO: 10)
```
        10         20         30         40         50         60
MGIKMEFQTQ VFVFVLLWLS GVDGDIVMTQ SQKFMSTSVG DRVSITCKAS QNVRTVVAWY 70         80         90        100        110        120
QQKPGQSPKT LIYLASNRHT GVPDRFTGSG SGTDFTLTIS NVQSEDLADY FCLQHWSYPL 130        140
TFGSGTKLEV KR........
```

In the heavy chain nucleic acid sequence (SEQ ID NO: 7), the boundary between the antibody variable region and the antibody constant region is located between adenine (A) at position 408 and guanine (G) at position 409. In the heavy chain amino acid sequence (SEQ ID NO: 8), the boundary between the antibody variable region and the antibody constant region is located between serine (S) at position 136 and alanine (A) at position 137. Furthermore, in the heavy chain nucleic acid sequence (SEQ ID NO: 7), the boundary between the signal sequence and the antibody variable region is located between thymine (T) at position 57 and guanine (G) at position 58. In the heavy chain amino acid sequence (SEQ ID NO: 8), the boundary between the signal sequence and the antibody variable region is located between cysteine (C) at position 19 and glutamic acid (E) at position 20.

Accordingly, the variable region in the chimeric anti-A33 antibody heavy chain has the nucleic acid sequence (SEQ ID NO: 7) ranging from guanine (G) at position 58 to adenine (A) at position 408. Further, the variable region in the heavy chain has the amino acid sequence (SEQ ID NO: 8) ranging from glutamic acid (E) at position 20 to serine (S) at position 136.

In the light chain nucleic acid sequence (SEQ ID NO: 9), the boundary between the antibody variable region and the antibody constant region is located between adenine (A) at position 393 and cytosine (C) at position 394. In the light chain amino acid sequence (SEQ ID NO: 10), the boundary between the antibody variable region and the antibody constant region is located between lysine (K) at position 131 and arginine (R) at position 132. Furthermore, in the light chain nucleic acid sequence (SEQ ID NO: 9), the boundary between the signal sequence and the antibody variable region is located between adenine (A) at position 72 and guanine (G) at position 73. In the light chain amino acid sequence (SEQ ID NO: 10), the boundary between the signal sequence and the antibody variable region is located between guanine (G) at position 24 and aspartic acid (D) at position 25.

Accordingly, the variable region in the chimeric anti-A33 antibody light chain has the nucleic acid sequence (SEQ ID NO: 9) ranging from guanine (G) at position 73 to adenine (A) at position 393. Further, the variable region in the light chain has the amino acid sequence (SEQ ID NO: 10) ranging from aspartic acid (D) at position 25 to lysine (K) at position 131.

The following Table 5 lists the nucleotide sequences of synthetic DNAs.

Host cells were transfected with the thus constructed expression vector for the chimeric anti-A33 recombinant antibody, thereby preparing recombinant-antibody-expressing cells. Host cells to be used for expression were CHO cells of a dhfr-deficient cell line (ATCC CRL-9096), CHO-Ras (Katakura Y., et al., Cytotechnology, 31: 103-109, 1999), or HEK293T (ATCC CRL-11268), for example.

Host cells were transfected with the vector by electroporation, lipofection, or the like. Approximately 2 μg of the antibody expression vector was linearized using restriction enzymes and then subjected to electroporation using a Bio-Rad electrophoreter under conditions of 350 V and 500 μF. $4 \times 10^6$ CHO cells were thus transfected with the gene and then the cells were inoculated on a 96-well culture plate. Lipofection was performed using LipofectAMINE Plus (produced by Gibco BRL) according to the manual included therein. After transfection with the vector, a drug corresponding to the selection marker used in the expression vector was added and then culture was continued. After confirmation of colonies, an antibody-expressing cell line was selected by the method described in Example 6. Antibody purification was performed from the selected cells as described in Example 8.

EXAMPLE 3

Preparation of Antigen

To obtain cells overexpressing A33 (to be used as an immunogen, for screening for an antibody, or the like) on the cell membranes, a plasmid expression vector for the full-length A33 amino acid sequence was constructed. A DNA encoding A33 was prepared by the PCR method.

a) Construction of Full-length A33 Expression Vector

A plasmid vector pΔEGFP-N1-GPA33 retaining A33-encoding cDNA was constructed to prepare a full-length A33 expression vector. pΔEGFP-N1-GPA33 was constructed by the following method. The complete full-length A33 DNA (GenBank DNA NM_005814: SEQ ID NO: 11 or protein NP_005305: SEQ ID NO: 12) was modified by performing a polymerase chain reaction (PCR) so as to add an EcoR I sequence to the 5' terminus and to add a Not I sequence and a termination codon to the 3' terminus. 30 cycles of a PCR reaction (94° C. for 15 seconds, 60° C. for 30 seconds, and 68° C. for 60 seconds) were performed using Human Colon Marathon-Ready cDNA (purchased from Becton Dickinson Bioscience Clontech) as a template, A33-F2 5'-GCAGAC-GAATTCAAGACCATGGTGGGGAAGAT-3' (SEQ ID NO: 13) and A33-R1 5'-CTCGAGCGGCCGCTCTGCTGCTG-GCCTGTCACTGGTCGAGGTG-3' (SEQ ID NO: 14) synthesized as primers, and KOD-plus DNA polymerase (produced by TOYOBO). The thus synthesized sequence was digested with EcoR I-Not I. The resultant was isolated as an EcoR I-Not I fragment. The fragment was then ligated to pΔEGFP-N1-vector (from which the region encoding EGFP protein of modified pEGFP-N1 (produced by Becton Dickinson Bioscience Clontech) had been deleted) that had been cleaved with the same enzymes. The thus obtained plasmid was named pΔEGFP-N1-GPA33. A 977-bp cDNA was encoded in A33 incorporated in pΔEGFP-N1-GPA33. Hereinafter, GeneAmp® PCR System 9700 (produced by PerkinElmer Japan) was used for regulating the temperatures for all PCR reactions in the examples.

b) Preparation of A33-Expressing Cells

The two following cell lines were transfected with pΔEGFP-N1-GPA33 constructed in a): FM3A cell line (Japanese Collection of Research Bioresources (JCRB) Cell Bank No. 0701) and the L929 cell line (ATCC No. CCL-1). Thus, 2 types of A33-expressing cells were prepared. The electroporation method was employed for FM3A cells. $5 \times 10^6$ FM3A cells were transfected with 20 μg of the pΔEGFP-N1-A33 vector using an electrophoreter (produced by BTX) under conditions of 350 V and 950 μF. The cells were inoculated on a 6-well culture plate. After 48 hours of culture at 37° C. under 5.0% carbonic acid gas, G418 (produced by Gibco BRL) was added to the cells at a concentration of 1 mg/mL and then the cells were cultured for 1 week. The A33 antigen expressed on the cell membrane surfaces was confirmed using the culture supernatant of the AS33 hybridoma (ATCC No. HB-8779). Flowcytometer (FCM: produced by Becton, Dickinson and Company) analysis was performed using the culture supernatant of the AS33 hybridoma as a primary antibody and a goat anti-mouse Ig gamma F(ab')$_2$ antibody (produced by Dako) labeled with R-phycoerythrin as a secondary antibody. Thus, among transfected cells that had acquired the trait of G418 resistance, cells expressing A33 on their cell membrane surfaces were selectively sorted.

L929 cells were transfected using Trans IT-LT1 (produced by TAKARA BIO INC). Transfection was performed by a method described in the related manual. After 24 hours of culture at 37° C. under 5.0% carbonic acid gas, G418 (produced by Gibco BRL) was added to the cells at a concentration of 1 mg/mL and then culture was performed for 1 week. In a manner similar to that in the case of FM3A cells, the A33 antigen expressed on the cell membrane surfaces was confirmed using the culture supernatant of the AS33 hybridoma. Flowcytometer (FCM: produced by Becton, Dickinson and Company) analysis was performed using the AS33 hybridoma (ATCC No. HB-8779) as a primary antibody, a goat anti-mouse Ig gamma F(ab')$_2$ antibody (produced by Dako) labeled with R-phycoerythrin as a secondary antibody. Thus, among transfected cells that had acquired the trait of G418 resistance, cells expressing A33 on their cell membrane surfaces were selectively sorted.

Single clones expressing the full-length human A33 antigen at high levels could be obtained from both cell lines. FM3A cells and L929 cells, which had expressed the A33 antigen protein at high levels, were named FM3A/A33 and L929/A33, respectively.

shA33EX-hFc protein was prepared for use as an immunogen or in ELISA upon screening for an antibody.

c) Construction of an Expression Vector for a Soluble A33 Human Fc Fusion Protein Outside the Cell Membrane To construct an expression vector (hereinafter referred to as shA33EX-hFc) for a soluble A33 human Fc fusion protein outside the cell membrane, a plasmid vector pTracer-CMV-humanFc-A33EXR retaining cDNA encoding the A33 region outside the cell membrane was constructed. pTracer-CMV-humanFc-A33EXR was constructed by the following method. The DNA of the A33 region outside the cell membrane (SEQ ID NO: 11) containing a secretory signal sequence was modified via a polymerase chain reaction (PCR) so as to add an EcoR I sequence to the 5' terminus and to add a Not I sequence and a termination codon to the 3' terminus. 30 cycles of a PCR reaction (94° C. for 15 seconds, 60° C. for 30 seconds, and 68° C. for 60 seconds) were performed using pΔEGFP-N1-A33 cDNA prepared in a) as a template, A33-F2 (SEQ ID NO: 13) and GPA-EXCRR2 5'-CTCGAGCGGCCGCCAGTTCATGGAGG-GAGATCTGACG-3' (SEQ ID NO: 15) synthesized as primers, and KOD-plus DNA polymerase (produced by TOYOBO). The thus synthesized sequence was digested with EcoR I-Not I. The resultant was isolated as an EcoR I-Not I fragment. The fragment was then ligated to a pTracer-CMV-humanFc vector (plasmid prepared by introducing FLAG and a human IgG1 Fc region at the Xba I and Apa I sites of modified pTracer-CMV (produced by Invitrogen Life Technologies)) that had been cleaved with the same enzymes. The thus obtained plasmid was named pTracer-CMV-humanFc-A33EXR.

Oligonucleotides such as PCR primers were all synthesized using a DNA autosynthesizer (model 3948; produced by PerkinElmer Japan, Applied Biosystems Division) according to the manual included therewith (see Matteucci, M. D. and Caruthers, M. H. (1981) J. Am. Chem. Soc. 103, 3185-3191). After completion of synthesis, each oligonucleotide was cleaved from support medium and subjected to deprotection. The thus obtained solution was dried, solidified, and then dissolved in distilled water. This solution was cryopreserved at −20° C. until use.

d) Expression and Purification of shA33EX-hFc Protein

Host cells were transfected with the shA33EX-hFc protein expression vector constructed in c), thereby preparing cells expressing the soluble A33 protein outside the cell membrane. Host cells to be used for expression were CHO cells of a dhfr-deficient cell line (ATCC CRL-9096), CHO-Ras (Katakura Y., et al., Cytotechnology, 31: 103-109, 1999), or HEK293T (ATCC CRL-11268), for example.

Host cells were transfected with the vector by electroporation, lipofection, or the like. Approximately 2 µg of the shA33EX-hFc protein expression vector was linearized using restriction enzymes and then subjected to electroporation using a Bio-Rad electrophoreter under conditions of 350 V and 500 µF. $4×10^6$ CHO cells were transfected with the gene, and then the cells were inoculated on a 96-well culture plate. Lipofection was performed using LipofectAMINE Plus (produced by Gibco BRL) according to the manual included therewith. After transfection with the vector, a drug corresponding to the selection marker for the expression vector was added and then culture was continued.

The shA33EX-hFc protein was purified from the culture supernatant by the following method. The culture supernatant containing the shA33EX-hFc protein was subjected to affinity purification using Hitrap Protein A FF (produced by Amersham Pharmacia Biotech), PBS as an adsorption buffer, 20 mM sodium citrate as an elution buffer, and 50 mM sodium chloride (pH 2.7). The eluted fraction was adjusted at pH 5.5 by the addition of a 50 mM sodium phosphate solution (pH 7.0). The thus prepared solution of the soluble A33 protein outside the cell membrane was substituted with PBS using Amicon Ultra-15 (produced by Amicon) and then sterilization by filtration was performed using a membrane filter MILLEX-GV (produced by Millipore) with a pore size of 0.22 µm. A purified shA33EX-hFc protein was thus obtained. The concentration of the shA33EX-hFc protein was found by measurement of absorbance at 280 nm and calculation with 1.4 OD being equivalent to 1 mg/mL (antibody concentration).

EXAMPLE 4

Production of Human-antibody-producing Mice

Mice used for immunization had genetic background such that they were homozygous for both disrupted endogenous Ig heavy chain and κ light chain. Furthermore, the mice simultaneously retained a chromosome 14 fragment (SC20) containing the human Ig heavy chain gene locus and a human Igκ chain transgene (KCo5). The mice had been produced by crossing mice of line A having the human Ig heavy chain gene locus with mice of line B having the human Igκ chain transgene. The mice of line A were homozygous for both disrupted endogenous Ig heavy chain and κ light chain and retained the inheritable chromosome 14 fragment (SC20), as described in the report of Tomizuka et al (Tomizuka. et al., Proc Natl Acad Sci U.S.A., 2000 Vol. 97: 722), for example. Furthermore, the mice of line B were homozygous for both disrupted endogenous Ig heavy chain and κ light chain. Furthermore, the mice of line B retaining the human Igκ chain transgene (KCo5) were transgenic mice, as described in the report of Fishwild et al (Nat Biotechnol, (1996) 114: 845).

Mice used in the following immunization experiments were obtained by crossing male mice of line A with female mice of line B or by crossing female mice of line A with male mice of line B, in the mouse sera of which the human Ig heavy chain and κ light chain were simultaneously detected (Ishida & Lonberg, IBC's 11th Antibody Engineering, Abstract 2000). In addition, the above human-antibody-producing mice (referred to as KM mice) are available from Kirin Brewery Co., LTD. by contract.

EXAMPLE 5

Preparation of Human Monoclonal Antibody Against A33

Monoclonal antibodies were prepared in this example according to a general method described in "*Tan-Clone-Kotai-Jikken-Manual* ("Experimental Manual for Monoclonal Antibody") (written by Tamie ANDO et al. and published by Kodansha Scientific, Ltd., Tokyo, Japan (1991)), for example. A33 used as an immunogen was the A33-expressing FM3A cell prepared in Example 1 or the shA33EX-hFc protein. Animals used for immunization were the human-antibody (immunoglobulin)-producing mice produced in Example 2.

For the purpose of preparing the anti-A33 human monoclonal antibody, A33-expressing FM3A cells ($1×10^7$ cells/mouse) prepared in Example 3 were mixed with an RIBI adjuvant (produced by Corixa Corporation), and then human-antibody-producing mice were initially immunized intraperitoneally with the mixture. Following the initial immunization, the animals were immunized with the same cells and the RIBI adjuvant every week for 8 times in total. 3 days before obtainment of the spleen described later, the shA33EX-hFc protein was administered at 20 µg/mouse via the caudal vein and recombinant human IL-6 was subcutaneously administered at 5 µg/mouse.

Furthermore, initial immunization was performed using the mixture of the shA33EX-hFc protein (10 µg/mouse) and a CpG adjuvant (produced by QIAGEN). Following the initial immunization, the same protein and the CpG adjuvant were used for immunization twice every 2 weeks. 2 weeks later, immunization was further performed using only such protein. 3 days before obtainment of the spleen described later, the shA33EX-hFc protein was administered at 10 µg/mouse via the caudal vein.

Furthermore, immunization was performed intraperitoneally with the shA33EX-hFc protein (10 µg/mouse), A33-expressing FM3A cells ($5 \times 10^6$ cells/mouse), and the RIBI adjuvant, followed by 1 to 4 times of immunization every 2 weeks. 4 days before obtainment of the spleen described later, the shA33EX-hFc protein was administered intraperitoneally at 5 µg/mouse.

The spleen was surgically obtained from each of the thus immunized mice and then added to 10 mL of serum-free DMEM medium (produced by Gibco BRL; (hereinafter, referred to as serum-free DMEM medium) containing 350 mg/mL sodium hydrogencarbonate, 50 units/mL penicillin, and 50 µg/mL streptomycin. The resultant was strained through a strainer with a mesh (cell strainer: produced by Falcon) using a spatula. The cell suspension that had passed through the strainer was centrifuged, so as to precipitate the cells. The cells were washed twice with serum-free DMEM medium and then suspended in serum-free DMEM medium, followed by determination of cell count. In the meantime, myeloma cells SP2/0 (ATCC No. CRL-1581) were cultured in DMEM medium (produced by Gibco BRL) containing 10% FCS (produced by Sigma; hereinafter, referred to as serum-containing DMEM medium) at 37° C. in the presence of 5% carbonic acid gas, so as not to exceed the cell concentration of $1 \times 10^6$ cells/mL. The myeloma cells SP2/0 (ATCC No. CRL-1581) were similarly washed with serum-free DMEM medium and then suspended in serum-free DMEM medium, followed by determination of a cell count. The thus collected cell suspension was mixed with the mouse myeloma cell suspension at a 5:1 ratio in terms of cell count. After centrifugation, the supernatant was completely removed. 1 mL of 50% (w/v) polyethylene glycol 1500 (produced by Boehringer Mannheim) was slowly added as a fusion agent to the pellets while agitating the solution using the tip of a pipette. 1 mL of serum-free DMEM medium pre-heated at 37° C. was slowly added in twice and then 7 mL of serum-free DMEM medium was further added to the resultant. After centrifugation, fusion cells obtained by removal of the supernatant were subjected to screening using a limiting dilution method as described below. Hybridoma selection was performed by culturing the cells in DMEM medium containing 10% FCS, IL-6 (10 ng/mL) (or 10% hybridoma cloning factor (hereinafter, referred to as HCF; produced by BIOBASE)), hypoxanthine (H), aminopterin (A), and thymidine (T) (hereinafter, referred to as HAT; produced by Sigma). Furthermore, single clones were obtained by a limiting dilution method using DMEM medium containing HT (produced by Sigma), 10% FCS, and IL-6 (or 10% HCF). Culture was performed in a 96-well microtiter plate (produced by Becton, Dickinson and Company). Selection (screening) of hybridoma clones producing the anti-A33 human monoclonal antibody and characterization of the human monoclonal antibody produced by each hybridoma were performed through measurement by enzyme-linked immunosorbent assay (ELISA) and flow cytometry (FMC), as described later.

Many hybridomas producing the human monoclonal antibody having the human immunoglobulin γ chain (hIgγ) and the human immunoglobulin light chain κ and having reactivity specific to A33 were obtained as confirmed by Cell ELISA, protein ELISA, and FMC analyses described in Example 6. In addition, each hybridoma clone producing the human anti-A33 monoclonal antibody of the present invention was named using numbers and letters in all the following examples, including this example, and in all tables or figures showing the test results in the examples. Furthermore, numbers and letters with "antibody" attached to one end thereof represent antibodies that are produced by the relevant hybridomas or recombinant antibodies produced by host cells retaining antibody genes (full-length or a variable region) isolated from the relevant hybridoma. Furthermore, within a contextually clear range, the name of a hybridoma clone may represent the name of an antibody. The following hybridoma clones represent single clones: 263A17, 125M10AA, 125M165DAAA, 125M96ABA, 125N26F6AA, 125Q47BA, 125Q54AAAA, and 125R5AAAA. 125M10AA, 125M165DAAA, 125M96ABA, 125N26F6AA, 125Q47BA, 125Q54AAAA, and 125R5AAAA were deposited on Aug. 24, 2004, with the International Patent Organism Depositary (IPOD) (Central 6, 1-1, Higashi 1, Tsukuba, Ibaraki, Japan) at the National Institute of Advanced Industrial Science and Technology (AIST) under accession Nos. FERM BP-10107 (denotation for identification: M10), FERM BP-10106 (denotation for identification: M165), FERM BP-10108 (denotation for identification: M96), FERM BP-10109 (denotation for identification: N26), FERM BP-10104 (denotation for identification: Q47), FERM BP-10105 (denotation for identification: Q54), and FERM ABP-10103 (denotation for identification: R5), respectively.

EXAMPLE 6

Selection of Clones Producing Human Anti-A33 Monoclonal Antibody having the Human Immunoglobulin γ Chain (hIgγ) and the Human Immunoglobulin Light Chain κ (Igκ)

Cell ELISA was performed as follows. FM3A/A33 prepared in Example 3 was added at $1 \times 10^5$ per well to a 96-well plate (produced by Falcon). Hybridoma supernatant was added and then incubation was performed at 4° C. for 30 minutes. Subsequently, the resultants were washed twice with PBS containing 2% FCS and then a goat anti-human IgG F(ab')$_2$ antibody labeled with horseradish peroxidase (50 µg/well: produced by IBL) was added, followed by 30 minutes of incubation at 4° C. The resultants were washed twice with PBS containing 2% FCS and then 100 µL of a TMB color development substrate (produced by DAKO) was added to each well, followed by 20 minutes of incubation at room temperature. 0.5 M sulfuric acid (100 µL/well) was added to each well to stop the reaction. Absorbance at a wavelength of 450 mn (reference wavelength: 570 nm) was measured using a microplate reader (1420 ARVO multilabel counter: produced by WALLAC). Antibody-producing clones showing positive reactions were selected. At this time, FM3A cells expressing no A33 antigen were used as negative controls. Specifically, culture supernatants that had reacted with FM3A/A33 cells but not with FM3A cells were selected as antibody-producing clones that had shown positive reactions.

Furthermore, protein ELISA was performed as follows. 50 µl of the shA33EX-hFc protein prepared in Example 3 and adjusted at pH 9.4 using a 1 µg/ml carbonate buffer was added to each well of a 96-well microplate for ELISA (Maxisorp produced by Nunc). Incubation was performed at room temperature for 1 hour or 4° C. overnight, so that the shA33EX-hFc protein was adsorbed to the microplate. Subsequently, the supernatant was discarded, and PBS containing 10% FCS was added to each well, followed by 1 hour. of incubation at 37° C. Thus, sites where no shA33EX-hFc protein had bound were blocked. In this manner, the microplate was prepared, wherein each well had been coated with the shA33EX-hFc protein. The culture supernatant (50 µl) of each hybridoma was added to each well, followed by 1 hour of reaction at room temperature. Each well was washed twice with PBS (PBS-T) containing 0.1% Tween20. Subsequently, a sheep anti-human Igκ antibody (50 µl/well, produced by The Binding Site) labeled with horseradish peroxidase was diluted 2500 fold using PBS (PBS-T) containing 0.1% Tween20. 50 µl of the solution was added to each well, followed by 1 hour of incubation at 37° C. The microplate was washed three times with PBS-T. 100 µl of a TMB color development substrate solution (produced by DAKO) was added to each well, followed by 20 minutes of incubation at room temperature. 0.5 M sulfuric acid (100 µl/well) was added to each well so as to stop the reaction. Absorbance at a wavelength of 450 nm (reference wavelength: 570 nm) was measured using a microplate reader (VersaMax produced by Molecular Devices Corporation). Antibody-producing clones showing positive reactions were selected.

Furthermore, FMC was performed as follows. The reactivity of hybridoma culture supernatants against human colorectal cancer cell line COLO205 cells expressing the A33 antigen was examined. The COLO205 cell line was suspended at a concentration of $2 \times 10^6$/ml in a PBS staining buffer (SB) containing 0.1% $NaN_3$ and 2% FCS. The cell suspension (50 µl/well) was dispensed in a 96-well round bottom plate (produced by Becton, Dickinson and Company). The culture supernatant (50 µl) of each hybridoma was added, followed by 30 minutes of incubation on ice. A negative control was prepared depending on each subclass. Specifically, a human IgG1 antibody (produced by Sigma) was adjusted at a concentration of 2 µg/ml with hybridoma culture medium and then 50 µl of the solution was added, followed by 30 minutes of incubation on ice. The resultant was washed twice with SB and then 50 µl of RPE fluorescence-labeled goat anti-human IgG F(ab')$_2$ antibody (produced by Southern Biotech) was added, followed by 30 minutes of incubation on ice. The resultant was washed once with SB and it was then suspended in 300 µl of a FACS buffer. The mean fluorescence intensity of each cell line was measured by FACS (FACS caliber produced by Becton, Dickinson and Company). As a result, the presence of antibodies binding to A33 expressed on cells was demonstrated because of their strong activity of binding to the cells of the COLO205 cell line.

EXAMPLE 7

Identification of Each Monoclonal Antibody Subclass in the Culture Supernatant

50 µl of the shA33EX-hFc protein prepared using a 1 µg/ml carbonate buffer (hereinafter, referred to as PBS) was added to each well of a 96-well microplate for ELISA (Maxisorp produced by Nunc). Incubation was performed at room temperature for 1 hour or 4° C. overnight, so that the shA33EX-hFc protein was adsorbed to the microplate. Subsequently, the supernatant was discarded, and PBS containing 10% FCS was added to each well, followed by 1 hour of incubation at room temperature or at 4° C. overnight. Thus, sites where no shA33EX-hFc protein had bound were blocked. In this manner, the microplate was prepared, with each well having been coated with the shA33EX-hFc protein. Subsequently, the microplate was washed twice with PBS (PBS-T) containing 0.1% Tween20. A sheep anti-human IgG1 antibody labeled with horseradish peroxidase, a sheep anti-human IgG2 antibody labeled with horseradish peroxidase, a sheep anti-human IgG3 antibody labeled with horseradish peroxidase, or a sheep anti-human IgG4 antibody labeled with horseradish peroxidase (diluted 1600-, 6400-, 25000-, and 25000-fold, respectively and produced by The Binding Site) was added at 50 82 L/well. Incubation was performed for 1.5 hours at room temperature. The microplate was washed three times with PBS-T containing 0.1% Tween20. A substrate buffer (TMB produced by DAKO) was added at 100 µL/well, followed by 20 minutes of incubation at room temperature. Subsequently, 0.5 M sulfuric acid (100 µl/well) was added to stop the reaction. Absorbance at a wavelength of 450 nm (reference wavelength: 570 nm) was measured using a microplate reader (VersaMax produced by Molecular Devices Corporation). The subclass of each clone was determined. Only human anti-A33 antibodies of subclass IgG1 were selected because a high priority was placed on ADCC and CDC.

Table 1 shows the reactivity of only the finally selected clones.

TABLE 1

| Antibody name | Subclass | Reactivity to COLO205 |
|---|---|---|
| Anti-DNP-IgG1 | IgG1 | − |
| cA33 | IgG1 | + |
| 263A17 | IgG1 | + |
| 125M10AA | IgG1 | + |
| 125M165DAAA | IgG1 | + |
| 125M96ABA | IgG1 | + |
| 125N26F6AA | IgG1 | + |
| 125Q47BA | IgG1 | + |
| 125Q54AAAA | IgG1 | + |
| 125R5AAAA | IgG1 | + |

EXAMPLE 8

Preparation of Each Type of Antibody

The human anti-A33 monoclonal antibodies obtained from the culture supernatants of hybridomas as described in Example 6 were purified by the following methods. A culture supernatant containing each type of human anti-A33 monoclonal antibody was cultured in SFM medium (produced by Invitrogen) containing 10% ultra low IgG FBS (produced by Invitrogen). The culture supernatant was subjected to affinity purification using Protein A Fast Flow gel (produced by Amersham Pharmacia Biotech), PBS as an adsorption buffer, and a 0.02 M glycine buffer (pH 3.6) as an elution buffer. The eluted fraction was adjusted at around pH 7.2 by the addition of 1M Tris (pH 8.0). The thus prepared antibody solution was substituted with PBS using Sephadex G25 desalting column (NAP column; produced by Amersham Pharmacia Biotech) and then sterilized by filtration using a membrane filter MILLEX-GV (produced by Millipore) with a pore size of 0.22 µm. Thus, purified human anti-A33 monoclonal antibodies were obtained. The concentration of each purified antibody was obtained by measurement of absorbance at 280 nm and calculation with 1.4 OD being equivalent to 1 mg/mL (antibody concentration).

EXAMPLE 9

Test of the Reactivity of Each Type of Purified Monoclonal Antibody to A33-expressing Cells The reactivity of each type of purified monoclonal antibody obtained in Example 8 to A33-antigen-expressing human colorectal cancer cell line COLO205 cells, LoVo cells (ATCC No. CCL-229), LS174T cells (ATCC No. CL-188), and NCI-H508 cells (ATCC No. CCL-253) was examined by FCM. Human colorectal cancer cell line HT-29 cells (ATCC No. HTB-38) expressing no A33 antigen were also examined as negative control cells. Each cell line was suspended at a concentration of $2 \times 10^6$/ml in a PBS Staining Buffer (SB) containing 0.1% $NaN_3$ and 2% FCS. The cell suspension (50 µl/well) was dispensed in a 96-well round bottom plate (produced by Becton, Dickinson and Company). 50 µl of each type of purified monoclonal antibody (adjusted using SB at a concentration of 2000, 400, 80, or 16 ng/ml) was added, and then incubation was performed on ice for 30 minutes. A negative control was prepared depending on each subclass. Specifically, a human IgG1 antibody (produced by Sigma) was adjusted using SB at a concentration of 2000, 400, 80, or 16 ng/ml. 50 µl of the solution was added, followed by 30 minutes of incubation on ice. The resultant was washed twice with SB and then 50 µl of an FITC fluorescence-labeled goat anti-human IgG F(ab')$_2$ antibody (produced by Southern Biotech), followed by 30 minutes of incubation on ice. The resultant was washed once with SB and then the resultant was suspended in 300 µl of a FACS buffer. The mean fluorescence intensity of each cell line was measured by FACS (FACScan produced by Becton, Dickinson and Company).

Table 2 shows the results. For COLO205 cells, the half value of the mean fluorescence intensity was determined to be 90. For LoVo cells, the half value of the mean fluorescence intensity was determined to be 25. For LS174T cells, the half value of the mean fluorescence intensity was determined to be 125. For NCI-H508 cells, the half value of the mean fluorescence intensity was determined to be 125. When an antibody concentration required to reach such value was 10<=x<100 ng/ml, the reactivity was represented by +++, when the same was 100<=x<1000 ng/ml, the reactivity was represented by ++, and when the same was 1000<=x<10000 ng/ml, the reactivity was represented by +. When no binding was observed, the reactivity was represented by –. Each type of purified monoclonal antibody showed binding to all cells expressing the A33 antigen.

TABLE 2

| Antibody name | COLO205 | LoVo | LS174T | NCI-H508 | HT-29 |
|---|---|---|---|---|---|
| Anti-DNP-IgG1 | – | – | – | – | – |
| cA33 | +++ | +++ | ++ | ++ | – |
| 263A17 | ++ | ++ | ++ | ++ | – |
| 125M10AA | +++ | +++ | +++ | +++ | – |
| 125M165DAAA | +++ | +++ | ++ | ++ | – |
| 125M96ABA | +++ | +++ | ++ | ++ | – |
| 125N26F6AA | +++ | +++ | ++ | ++ | – |
| 125Q47BA | +++ | +++ | ++ | ++ | – |
| 125Q54AAAA | +++ | +++ | ++ | ++ | – |
| 125R5AAAA | +++ | +++ | ++ | ++ | – |
| | Half value of mean fluorescence intensity 90 10 <= x < 100 ng/ml; +++ 100 <= x < 1000 ng/ml; ++ 1000 <= x < 10000 ng/ml; + No binding; – | Half value of mean fluorescence intensity 25 10 <= x < 100 ng/ml; +++ 100 <= x < 1000 ng/ml; ++ 1000 <= x < 10000 ng/ml; + No binding; – | Half value of mean fluorescence intensity 125 10 <= x < 100 ng/ml; +++ 100 <= x < 1000 ng/ml; ++ 1000 <= x < 10000 ng/ml; + No binding; – | Half value of mean fluorescence intensity 125 10 <= x < 100 ng/ml; +++ 100 <= x < 1000 ng/ml; ++ 1000 <= x < 10000 ng/ml; + No binding; – | |

EXAMPLE 10

Competition Test Regarding Each Type of Purified Monoclonal Antibody and the Mouse Anti-A33 Antibody Whether or not each type of purified monoclonal antibody obtained in Example 8 recognizes an epitope similar to that of the mouse anti-A33 antibody was examined by a competition test using FCM. The COLO205 cell line was suspended at a concentration of $2 \times 10^6$/ml in a PBS Staining Buffer (SB) containing 0.1% $NaN_3$ and 2% FCS. The cell suspension (50 µl/well) was dispensed in a 96-well round bottom plate (produced by Becton, Dickinson and Company). The purified mouse anti-A33 antibody prepared in Example 1 was not added or added at a concentration of 100 µg/ml to the wells containing each type of purified monoclonal antibody (1 µg/ml and 50 µl), followed by 30 minutes of incubation on ice. A mouse negative control (containing no purified anti-A33 antibody added thereto) was prepared as follows. A human IgG1 antibody (produced by Sigma) was adjusted at a concentration of 1 µg/ml with SB and then 50 µl of the solution was added, followed by 30 minutes of incubation on ice. The resultant was washed twice with SB and then 50 µl of FITC fluorescence-labeled goat anti-human IgG F(ab')$_2$ antibody (produced by IBL) was added, followed by 30 minutes of incubation on ice. The resultant was washed once with SB and then the resultant was suspended in 300 µl of a FACS buffer. The mean fluorescence intensity of each cell line was measured by FACS (FACScan produced by Becton, Dickinson and Company). The inhibition (%) between each type of purified monoclonal antibody and the mouse A33 antibody was calculated by the following formula:

$$\text{Inhibition (\%)} = \{100 - (100 \times \text{mean fluorescence intensity after preincubation with mouse } A33 \text{ antibody})/(\text{mean fluorescence intensity after preincubation without mouse } A33 \text{ antibody})\}.$$

A purified monoclonal antibody showing inhibition (%) of 25% or less was classified as a "non-blocker," one showing inhibition (%) of 25% or more and less than 90% was classified as a "partial blocker," and one showing inhibition (%) of 90% or more was classified as a "blocker." As a result, 263A17, 125M10AA, and 125M96ABA were classified as "non-blockers," 125M165DAAA and 125N26F6AA were classified as "blockers," and 125Q47BA, 125Q54AAAA, and 125R5AAAA were classified as "partial blockers." Table 3 shows the results.

TABLE 3

| Antibody name | Inhibition (%) | Classification |
| --- | --- | --- |
| cA33 | 94.2 | Blocker |
| 263A17 | 3.7 | Non-blocker |
| 125M10AA | 5.0 | Non-blocker |
| 125M165DAAA | 96.0 | Blocker |
| 125M96ABA | 22.8 | Non-blocker |
| 125N26F6AA | 98.0 | Blocker |
| 125Q47BA | 64.1 | Partial blocker |
| 125Q54AAAA | 46.5 | Partial blocker |
| 125R5AAAA | 63.9 | Partial blocker |

EXAMPLE 11

Method for Obtaining Normal Human Mononuclear Leukocytes

First, normal human peripheral blood mononuclear cells were prepared using Ficoll (Ficoll-PaquePLUS: produced by Amersham Pharmacia Biotech) according to a standard method. Normal human blood was collected in a blood collection bag (produced by TERUMO) containing a sodium citrate solution as an anticoagulant. The normal human blood was multi-layered in Ficoll and then specific gravity centrifugation (800 G, room temperature, and 15 minutes) was performed to separate monocytes. The intermediate layer was extracted in the form of mononuclear leukocytes, and the extracted mononuclear leukocytes were then diluted with PBS. The diluted solution was repeatedly centrifuged at 200 G for 10 minutes three times, thereby removing blood platelets remaining in the supernatant. Normal human peripheral blood mononuclear cells (hereinafter referred to as PBMC) were obtained by the above method and then used as PBMC for Example 12. Furthermore, CD4+ T cells were isolated from PBMC using a CD4+ T cell Isolation kit II (produced by Miltenyi Biotec) according to the instructions included therein. The remaining cell group was also used as PBMC for Example 12.

EXAMPLE 12

Test of the Cytotoxicity of Each Type of Purified Monoclonal Antibody

Antibody-mediated cytotoxicity was determined as follows. Cytotoxicity (antibody-dependent cellular cytotoxicity, hereinafter referred to as ADC) against target cells was determined in the presence of cells having killer activity, such as NK cells or neutrophils, and antibodies. Furthermore, cytotoxicity (complement-dependent cytotoxicity, hereinafter referred to as CDC) against target cells was determined in the presence of complements and antibodies. The antibodies used herein were: each type of purified monoclonal antibody prepared in Example 8 and a cA33 recombinant antibody as a control anti-A33 antibody. Furthermore, an anti-DNP IgG1 antibody was used as a negative control.

The method is simply described as follows. Target cells were caused to incorporate radioactive chromium ($^{51}Cr$) into the cytoplasms and γ-dose was measured to find the amounts of $^{51}Cr$ that are released in culture solutions because of cell death.

Specifically, $10^6$ cells of colorectal cancer cell line COLO205 (ATCC No. CCL-86) and $10^6$ NCI-H508 cells (ATCC No. CCL-253) were separately suspended as target cells in 15 μL of fetal calf serum (FCS). 50 μL (37 MBq/mL) of $^{51}Cr$-labeled sodium chromate (produced by PerkinElmer; hereinafter referred to as $^{51}Cr$) was added, followed by 1 hour of culture at 37° C. Next, 10 mL of medium was added. Discarding of medium by centrifugation was repeated 3 times, thereby eliminating $^{51}Cr$ that had not been incorporated within the cells.

In the ADCC assay, 5,000 $^{51}Cr$-labeled target cells and 500,000 healthy human peripheral blood mononuclear leukocytes obtained by the method described in Example 11 were cultured in a V-bottom 96-well plate (produced by Coaster) at a total volume of 200 μL with antibody having each concentration at 37° C. in the presence of 5% $CO_2$ for 4 hours.

In the CDC assay, 5000 $^{51}Cr$-labeled target cells and human serum-derived complements (produced by Sigma) at a final concentration of 5% were cultured in a V-bottom 96-well plate at a total volume of 200 μL with antibody having each concentration at 37° C. in the presence of 5% $CO_2$ for 4 hours.

In both ADCC and CDC assays, the plate was subjected to centrifugation after culture to cause the cells to precipitate. Each type of purified monoclonal antibody was prepared at a concentration of 0.4-500 ng/ml and then 50 μL of the solution was transferred to a 96-well plate (Lumaplate™-96; produced by Packard Instrument) including a powder scintillator. The resultant was dried at 55° C. for 1.5 hours. After confirming that the plate had dried, the plate was covered with a special cover (TopSeal™-A; 96-well microplates; produced by Packard Instrument). The γ-ray dose was measured with a scintillation counter (TopCount; produced by Packard Instrument).

FIG. 1A to FIG. 1D and Table 4 show the results. In the case of ADCC against COLO205 cells, the half value of the specific lysis (%) was determined to be 15%. When an antibody concentration required to reach such value was 1<=x<10 ng/ml, the cytotoxicity was represented by +++, when the same was 10<=x<100 ng/ml, the cytotoxicity was represented by ++, when the same was 100<=x<1000 ng/ml, cytotoxicity was represented by +, and when no specific lysis (%) was obtained, the cytotoxicity was represented by −. In the case of ADCC against NCI-H508 cells, the half value of the specific lysis (%) was determined to be 15%. When an antibody concentration required to reach such value was 1<=x<10 ng/ml, the cytotoxicity was represented by +++, when the same was 10<=x<100 ng/ml, the cytotoxicity was represented by ++, when the same was 100<=x<1000 ng/ml, the cytotoxicity was represented by +, and when no specific lysis (%) was observed, the cytotoxicity was represented by −.

In the case of CDC against COLO205 cells, the half value of the specific lysis (%) was determined to be 10%. When an antibody concentration required to reach such value was 10<=x<100 ng/ml, the cytotoxicity was represented by +++, when the same was 100<=x<1000 ng/ml, the activity was represented by ++, when the same required to reach such value was x>=1000 ng/ml, the activity was represented by +, and when no specific lysis (%) was obtained, the activity was represented by −. Furthermore, in the case of CDC against NCI-H508 cells, the half value of the specific lysis (%) was determined to be 25%. When an antibody concentration required to reach such value was 10<=x<100 ng/ml, the cytotoxicity was represented by +++, when the same was 100<=x<1000 ng/ml, the cytotoxicity was represented by ++, when the same was x>=1000 ng/ml, the cytotoxicity was represented by +, and when no specific lysis (%) was obtained, the cytotoxicity was represented by −.

In the case of ADCC, cA33 and 125Q54AAAA showed high cytotoxicity, while in the case of CDC, 125M10AA showed high cytotoxicity.

| 5 × Buffer | 2 µl |
|---|---|
| DTT | 1 µl |
| DNTP mix | 1 µl |
| PowerScript Reverse Transcriptase | 1 µl |

TABLE 4

| Antibody name | COLO205 | | NCI-H508 | |
|---|---|---|---|---|
| | ADCC | CDC | ADCC | CDC |
| Anti-DNP-IgG1 | − | − | − | − |
| cA33 | +++ | − | +++ | − |
| 263A17 | ++ | ++ | +++ | ++ |
| 125M10AA | ++ | +++ | +++ | +++ |
| 125M165DAAA | ++ | + | +++ | ++ |
| 125M96ABA | + | ++ | ++ | +++ |
| 125N26F6AA | ++ | − | ++ | + |
| 125Q47BA | ++ | ++ | ++ | ++ |
| 125Q54AAAA | +++ | ++ | +++ | ++ |
| 125R5AAAA | ++ | ++ | +++ | ++ |
| | Half value of specific lysis (%) 15% | Half value of specific lysis (%) 10% | Half value of specific lysis (%) 15% | Half value of specific lysis (%) 25% |
| | 1 <= x < 10 ng/ml; +++ | 10 <= x < 100 ng/ml; +++ | 1 <= x < 10 ng/ml; +++ | 10 <= x < 100 ng/ml; +++ |
| | 10 <= x < 100 ng/ml; ++ | 100 <= x < 1000 ng/ml; ++ | 10 <= x < 100 ng/ml; ++ | 100 <= x < 1000 ng/ml; ++ |
| | 100 <= x < 1000 ng/ml; + | x >= 1000 ng/ml; + | 100 <= x < 1000 ng/ml; + | x >= 1000 ng/ml; + |
| | No specific lysis; − | No specific lysis; − | No specific lysis; − | No specific lysis; − |

EXAMPLE 13

Preparation of the Gene Encoding Each Type of Monoclonal Antibody (1) cDNA Synthesis for Each Type of Monoclonal Antibody Hybridomas 263A17, 125M10AA, 125M165DAAA, 125M96ABA, 125N26F6AA, 125Q47BA, 125Q54AAAA, and 125R5AAAA were separately cultured in DMEM medium (produced by Gibco BRL) containing 10 ng/mL IL-6 or 10% HCF (produced by BIOBASE) and 10% Fetal Bovine Serum (produced by HyClone). After the cells were harvested by centrifugation, ISOGEN (produced by NIPPON GENE) was added and then total RNAs were extracted according to the relevant instruction manual. Variable regions of antibody cDNAs were cloned using a SMART RACE cDNA amplification kit (produced by Becton Dickinson Bioscience Clontech) according to instructions included therein.

1st strand cDNA was prepared using 5 µg of total RNA as a template.

1st Strand cDNA Synthesis

| Total RNA | 5 µg/3 µl |
|---|---|
| 5'CDS | 1 µl |
| SMART oligo | 1 µl |

A reaction solution with the above composition was incubated at 70° C. for 2 minutes, and then the following components were added, followed by 1.5 hours of incubation at 42° C.

Furthermore, 100 µl of a tricine buffer was added and then incubation was performed at 72° C. for 7 minutes, thereby obtaining 1st strand cDNA.

(2) PCR Amplification of Heavy Chain and Light Chain Genes and Confirmation of the Nucleotide Sequences (2)-1: PCR Amplification of the Heavy Chain and Light Chain Genes of Hybridoma 263A17 cDNA amplification was performed by preparing the following reaction solution using KOD-Plus-DNA polymerase (produced by TOYOBO).

| Sterile H$_2$O | 29.5 µl |
|---|---|
| cDNA | 2.5 µl |
| KOD-Plus-buffer (10X) | 5 µl |
| dNTP Mix (2 mM) | 4 µl |
| MgSO$_4$ (25 mM) | 2 µl |
| KOD-Plus-(1 unit/µl) | 1 µl |
| Universal primer A mix (UPM) (10X) | 5 µl |
| Gene specific primers (GSP) | 1 µl |
| Total volume | 50 µl |

The reaction solution with the above composition was adjusted to a final volume of 50 µl with re-distilled water and then subjected to PCR.

The 263A17 heavy chain gene was amplified by repeating a reaction cycle (98° C. for 1 second and 68° C. for 30 seconds) 30 times using the UPM primer included in a SMART RACE cDNA Amplification Kit and a IgG1p primer (5'-TCTTGTCCACCTTGGTGTTGCTGGGCTTGTG-3') (SEQ ID NO: 16). Meanwhile, the 263A17 light chain gene was amplified by repeating a reaction cycle (98° C. for 1 second and 68° C. for 30 seconds) 30 times using the UPM primer and an hk-2 (5'-GTT GAA GCT CTT TGT GAC GGG CGA GC-3') (SEQ ID NO: 17) primer.

(2)-2: PCR Amplification of Heavy Chain and Light Chain Genes of Hybridomas 125M10AA, 125M96ABA, 125Q47BA, 125Q54AAAA, and 125R5AAAA Reaction conditions employed herein were similar to those in (2)-1. The 125M10AA, 125M96ABA, 125Q47BA, 125Q54AAAA, and 125R5AAAA heavy chain genes were amplified by repeating a reaction cycle (98° C. for 1 second and 68° C. for 30 seconds) 30 times using the UPM primer and the IgG1p primer (SEQ ID NO: 16). Furthermore, a reaction cycle (98° C. for 1 second and 68° C. for 30 seconds) was repeated 20 times using 1 µl of the reaction solution as a template, a NUPM primer (SMART RACE cDNA amplification Kit; produced by Becton Dickinson Bioscience Clontech), and a IgG2p/G134 primer (5'-TGC ACG CCG CTG GTC AGG GCG CCT GAG TTC C-3') (SEQ ID NO: 18). Meanwhile, the 125M10AA, 125M96ABA, 125Q47BA, 125Q54AAAA, and 125R5AAAA light chain genes were amplified by repeating a reaction cycle (98° C. for 1 second and 68° C. for 30 seconds) 30 times using the UPM primer and the hk-2 primer (SEQ ID NO: 17). Furthermore, a reaction cycle (98° C. for 1 second and 68° C. for 30 seconds) was repeated 20 times using 1 µl of the reaction solution as a template, the NUPM primer, and an hk-5 primer (5'-AGG CAC ACA ACA GAG GCA GTT CCA GAT TTC-3') (SEQ ID NO: 19).

(2)-3: PCR Amplification of the Heavy Chain and Light Chain Genes of Hybridomas 125M165DAAA and 125N26F6AA Reaction conditions employed herein were similar to those in (2)-1. 125M165DAAA and 125N26F6AA heavy chain genes were amplified by repeating a reaction cycle (98° C. for 1 second and 68° C. for 30 seconds) 30 times using a UPM primer and an hh-2 primer (5'-GCT GGA GGG CAC GGT CAC CAC GCT G-3') (SEQ ID NO: 20). Furthermore, a reaction cycle (98° C. for 1 second and 68° C. for 30 seconds) was repeated 20 times using 1 µl of the reaction solution as a template, a NUPM primer, and an hh-4 primer (5'-GGT GCC AGG GGG AAG ACC GAT GG-3') (SEQ ID NO: 21). Meanwhile, the 125M165DAAA and 125N26F6AA light chain genes were amplified by repeating a reaction cycle (98° C. for 1 second and 68° C. for 30 seconds) 30 times using the UPM primer and the hk-2 primer (SEQ ID NO: 17). Furthermore, a reaction cycle (98° C. for 1 second and 68° C. for 30 seconds) was repeated 20 times using 1 µl of the reaction solution as a template, an NUPM primer, and the hk-5 primer (SEQ ID NO: 19).

PCR fragments of the heavy and light chains amplified as described above were separately harvested by ethanol precipitation, harvested by agarose gel electrophoresis, and then purified using a QIAquick Gel Extraction Kit (produced by QIAGEN), which is a DNA purification kit that uses membranes. The thus purified HV and LV amplified fragments were separately subcloned into a PCR 4 Blunt-TOPO vector of a Zero Blunt TOPO PCR Cloning Kit (produced by Invitrogen). For the plasmid DNAs of the thus obtained clones, the nucleotide sequences of the insert DNAs were analyzed. M13FW (SEQ ID NO: 3) and M13RV (SEQ ID NO: 4) were used as primers for determination of the DNA nucleotide sequences.

DNAs encoding the 263A17 heavy chain variable region and the light chain variable region and the amino acid sequences of the heavy chain variable region and the light chain variable region are each shown below.

```
<263A17 heavy chain nucleic acid sequence> (SEQ ID NO: 22)
         10         20         30         40         50         60
ATGGAGTTTG GCTGAGCTG GCTTTTTCTT GTGGCTATTT TAAAAGGTGT CCAGTGTGAG 70         80         90        100        110        120
GTGCAGTTGT TGGAGTCTGG GGGAGGCTTG GTACAGCCTG GGGGGTCCCT GAGACTCTCC 130        140        150        160        170        180
TGTGCAGCCT CTGGATTCAC CTTTAGCAGC TATGCCATGA GCTGGATCCG CCAGGCTCCA 190        200        210        220        230        240
GGGAAGGGGC TGGAGTGGGT CTCAGCTATT AGTGCTAGTG GTGGTAGCAC ATACTACGCA 250        260        270        280        290        300
GACTCCGTGA AGGGCCGGTT CACCATCTCC AGAGACAATT CCAAGAACAC GCTGTATCTG 310        320        330        340        350        360
CAAATGAACA GCCTGAGAGC CGAGGACACG GCCGTATATT ACTGTGCGAA AGATCGGATA 370        380        390        400        410        420
GTGGGAGCTA CGAACTACTA CTACGGTATG GACGTCTGGG GCCAAGGGAC CACGGTCACC 430        440        450        460        470        480
GTCTCCTCAG CTAGC.....

<263A17 heavy chain amino acid sequence> (SEQ ID NO: 23)
         10         20         30         40         50         60
MEFGLSWLFL VAILKGVQCE VQLLESGGGL VQPGGSLRLS CAASGFTFSS YAMSWIRQAP 70         80         90        100        110        120
GKGLEWVSAI SASGGSTYYA DSVKGRFTIS RDNSKNTLYL QMNSLRAEDT AVYYCAKDRI 130        140        150        160        170        180
VGATNYYYGM DVWGQGTTVT VSSAS.....
```

-continued

<263A17 light chain nucleic acid sequence> (SEQ ID NO: 24)

```
          10         20         30         40         50         60
ATGGACATGA GGGTCCCCGC TCAGCTCCTG GGGCTCCTGC TGCTCTGGTT CCCAGGTTCC 70         80         90        100        110        120
AGATGCGACA TCCAGATGAC CCAGTCTCCA CCTTCCGTGT CTGCATCTGT AGGAGACAGA 130        140        150        160        170        180
GTCACCATCA CTTGTCGGGC GAGTCAGGGT ATTAGCAGCT GGTTAGCCTG GTATCAGCAT 190        200        210        220        230        240
AAACCAGGGA AAGCCCCAAA GCTCCTGATC TATGGTGCAT CCAGTTTGCA AAGTGGGGTC 250        260        270        280        290        300
CCATCAAGGT TCAGCGGCAG TGGATCTGGG ACAGATTTCA CTCTCACCAT CAGCAGCCTG 310        320        330        340        350        360
CAGCCTGAAG ATTTTGCAAC TTACTATTGT CAACAGGCTA ATAGTTTCCC TATCACCTTC 370        380        390
GGCCAAGGGA CACGACTGGA GATTAAACGT
```

<263A17 light chain amino acid sequence> (SEQ ID NO: 25)

```
          10         20         30         40         50         60
MDMRVPAQLL GLLLLWFPGS RCDIQMTQSP PSVSASVGDR VTITCRASQG ISSWLAWYQH 70         80         90        100        110        120
KPGKAPKLLI YGASSLQSGV PSRFSGSGSG TDFTLTISSL QPEDFATYYC QQANSFPITF

130
GQGTRLEIKR
```

In the heavy chain nucleic acid sequence (SEQ ID NO: 22), the boundary between the antibody variable region and the antibody constant region is located between adenine (A) at position 429 and guanine (G) at position 430. In the heavy chain amino acid sequence (SEQ ID NO: 23), the boundary between the antibody variable region and the antibody constant region is located between serine (S) at position 143 and alanine (A) at position 144. Furthermore, in the heavy chain nucleic acid sequence (SEQ ID NO: 22), the boundary between the signal sequence and the antibody variable region is located between thymine (T) at position 57 and guanine (G) at position 58. In the heavy chain amino acid sequence (SEQ ID NO: 23), the boundary between the signal sequence and the antibody variable region is located between cysteine (C) at position 19 and glutamic acid (E) at position 20.

Accordingly, the variable region in the 263A17 antibody heavy chain has the nucleic acid sequence (SEQ ID NO: 22) ranging from guanine (G) at position 58 to adenine (A) at position 429. Further, the variable region in the heavy chain has the amino acid sequence (SEQ ID NO: 23) ranging from glutamic acid (E) at position 20 to serine (S) at position 143.

In the light chain nucleic acid sequence (SEQ ID NO: 24), the boundary between the antibody variable region and the antibody constant region is located between adenine (A) at position 387 and cytosine (C) at position 388. In the light chain amino acid sequence (SEQ ID NO: 25), the boundary between the antibody variable region and the antibody constant region is located between lysine (K) at position 129 and arginine (R) at position 130. Furthermore, in the light chain nucleic acid sequence (SEQ ID NO: 24), the boundary between the signal sequence and the antibody variable region is located between cytosine (C) at position 66 and guanine (G) at position 67. In the light chain amino acid sequence (SEQ ID NO: 25), the boundary between the signal sequence and the antibody variable region is located between cysteine (C) at position 22 and aspartic acid (D) at position 23.

Accordingly, the variable region in the 263A17 antibody light chain has the nucleic acid sequence (SEQ ID NO: 24) ranging from guanine (G) at position 67 to adenine (A) at position 387. Further, the variable region in the light chain has the amino acid sequence (SEQ ID NO: 25) ranging from aspartic acid (D) at position 23 to lysine (K) at position 129.

DNAs encoding the 125M10AA heavy chain variable region and the light chain variable region and the amino acid sequences of the heavy chain variable region and the light chain variable region are each shown below.

<125M10AA heavy chain nucleic acid sequence> (SEQ ID NO: 26)

```
          10         20         30         40         50         60
ATGGATCTCA TGTGCAAGAA AATGAAGCAC CTGTGGTTCT TCCTCCTGCT GGTGGCGGCT 70         80         90        100        110        120
CCCAGATGGG TCCTGTCCCA GCTGCAGGTG CAGGAGTCGG GCCCAGGACT GGTGAAGCCT 130        140        150        160        170        180
TCGGAGACCC TGTCCCTCAT CTGCACTGTC TCTGGTGGCT CCATCAGGAC CAGTGGTTAC 190        200        210        220        230        240
TACTGGGGCT GGTTCCGCCA GCCCCCAGGG AAGGGACTGG AGTGGATTGG GACTAGTCAT 250        260        270        280        290        300
AATAGTGGGA GCACCTACTA CAACCCGTCC CTCAAGAGTC GAGTCACCAT ATCCGTAGAC
```

```
            310        320        330        340        350        360
     ACGTCCAAGA AGCAGTTCTC CCTGAAGCTG AACTCTGTGA CCGCCGCAGA CACGGCTGTG 370        380        390        400        410        420
     TATTACTGTG CGAGACAAGG TTACGATTTT AAAGTCAATA TAGACGTCTG GGGACAAGGG 430        440        450
     ACCACGGTCA CCGTCTCCTC AGCTAGC...

<125M10AA heavy chain amino acid sequence> (SEQ ID NO: 27)
            10         20         30         40         50         60
     MDLMCKKMKH LWFFLLLVAA PRWVLSQLQV QESGPGLVKP SETLSLICTV SGGSIRTSGY 70         80         90        100        110        120
     YWGWFRQPPG KGLEWIGTSH NSGSTYYNPS LKSRVTISVD TSKNQFSLKL NSVTAADTAV 130        140        150
     YYCARQGYDF KVNIDVWGQG TTVTVSSAS.

<125M10AA light chain nucleic acid sequence> (SEQ ID NO: 28)
            10         20         30         40         50         60
     ATGGAAGCCC CAGCTCAGCT TCTCTTCCTC CTGCTACTCT GGCTCCCAGA TACCACCGGA 70         80         90        100        110        120
     GAAATTGTGT TGACACAGTC TCCAGCCACC CTGTCTTTGT CTCCAGGGGA AAGAGCCACC 130        140        150        160        170        180
     CTCTCCTGCA GGGCCAGTCA GAGTGTTAGC AGCTACTTAG CCTGGTACCA ACAGAAACCT 190        200        210        220        230        240
     GGCCAGGCTC CCAGGCTCCT CATCTATGAT GCATCCAACA GGGCCACTGG CATCCCAGCC 250        260        270        280        290        300
     AGGTTCAGTG GCAGTGGGTC TGGGACAGAC TTCACTCTCA CCATCAGCAG CCTAGAGCCT 310        320        330        340        350        360
     GAAGATTTTG CAGTTTATTA CTGTCAGCAG CGTAGCAACT GGCCGCTCAC TTTCGGCGGA 370        380        390
     GGGACCAAGG TGGAGATCAA ACGA......

<125M10AA light chain amino acid sequence> (SEQ ID NO: 29)
            10         20         30         40         50         60
     MEAPAQLLFL LLLWLPDTTG EIVLTQSPAT LSLSPGERAT LSCRASQSVS SYLAWYQQKP 70         80         90        100        110        120
     GQAPRLLIYD ASNRATGIPA RFSGSGSGTD FTLTISSLEP EDFAVYYCQQ RSNWPLTFGG

130
     GTKVEIKR..
```

In the heavy chain nucleic acid sequence (SEQ ID NO: 26), the boundary between the antibody variable region and the antibody constant region is located between adenine (A) at position 441 and guanine (G) at position 442. In the heavy chain amino acid sequence (SEQ ID NO: 27), the boundary between the antibody variable region and the antibody constant region is located between serine (S) at position 147 and alanine (A) at position 148. Furthermore, in the heavy chain nucleic acid sequence (SEQ ID NO: 26), the boundary between the signal sequence and the antibody variable region is located between cytosine (C) at position 78 and cytosine (C) at position 79. In the heavy chain amino acid sequence (SEQ ID NO: 27), the boundary between the signal sequence and the antibody variable region is located between serine (S) at position 26 and glutamine (Q) at position 27.

Accordingly, the variable region in the 125M10AA antibody heavy chain has the nucleic acid sequence (SEQ ID NO: 26) ranging from cytosine (C) at position 79 to adenine (A) at position 441. Further, the variable region in the heavy chain has the amino acid sequence (SEQ ID NO: 27) ranging from glutamine (Q) at position 27 to serine (S) at position 147.

In the light chain nucleic acid sequence (SEQ ID NO: 28), the boundary between the antibody variable region and the antibody constant region is located between adenine (A) at position 381 and cytosine (C) at position 382. In the light chain amino acid sequence (SEQ ID NO: 29), the boundary between the antibody variable region and the antibody constant region is located between lysine (K) at position 127 and arginine (R) at position 128. Furthermore, in the light chain nucleic acid sequence (SEQ ID NO: 28), the boundary between the signal sequence and the antibody variable region is located between adenine (A) at position 60 and guanine (G) at position 61. In the light chain amino acid sequence (SEQ ID NO: 29), the boundary between the signal sequence and the antibody variable region is located between glycine (G) at position 20 and glutamic acid (E) at position 21.

Accordingly, the variable region in the 125M10AA antibody light chain has the nucleic acid sequence (SEQ ID NO: 28) ranging from guanine (G) at position 61 to adenine (A) at position 381. Further, the variable region in the light chain has the amino acid sequence (SEQ ID NO: 29) ranging from glutamic acid (E) at position 21 to lysine (K) at position 127.

DNAs encoding the 125M165DAAA heavy chain variable region and the light chain variable region and the amino acid sequences of the heavy chain variable region and the chain variable region are each shown below.

<125M165DAAA heavy chain nucleic acid sequence> (SEQ ID NO: 30)
```
         10         20         30         40         50         60
ATGGAGTTTG GGCTGAGCTG GGTTTTCCTC GTTGCTCTTT TAAGAGGTGT CCAGTGTCAG 70         80         90        100        110        120
GTGCAGCTGG TGGAGTCTGG GGGAGGCGTG GTCCAGCCTG GGAGGTCCCT GAGACTCTCC 130        140        150        160        170        180
TGTGCAGCGT CTGGATTCAC CTTCAGTTAT TATGGCATGC ACTGGGTCCG CCAGGCTCCA 190        200        210        220        230        240
GGCAAGGGGC TGGAGTGGGT GGCAGTTATA TGGTATGATG GAAGTAATAA ATACTATGCA 250        260        270        280        290        300
GACTCCGTGA AGGGCCGATT CACCATCTCC AGAGACAATT CCAAGAAAAC GCTGTATCTG 310        320        330        340        350        360
CAAATGAACA GCCTGAGAGC CGAGGACACG GCTGTGTATT ACTGTGCGAG AGATGGGCAT 370        380        390        400        410        420
AGCAGTGGCT GGGGGGACTT CCAGCACTGG GGCCAGGGCA CCCTGGTCAC CGTCTCCTCA

430
GCTAGC....
```

<125M165DAAA heavy chain amino acid sequence> (SEQ ID NO: 31)
```
         10         20         30         40         50         60
MEFGLSWVFL VALLRGVQCQ VQLVESGGGV VQPGRSLRLS CAASGFTFSY YGMHWVRQAP 70         80         90        100        110        120
GKGLEWVAVI WYDGSNKYYA DSVKGRFTIS RDNSKKTLYL QMNSLRAEDT AVYYCARDGH 130        140        150
SSGWGDFQHW GQGTLVTVSS AS........
```

<125M165DAAA light chain nucleic acid sequence> (SEQ ID NO: 32)
```
         10         20         30         40         50         60
ATGGAAGCCC CAGCTCAGCT TCTCTTCCTC CTGCTACTCT GGCTCCCAGA TACCACCGGA 70         80         90        100        110        120
GAAATTGTGT TGACACAGTC TCCAGCCACC CTGTCTTTGT CTCCAGGGGA AAGAGCCACC 130        140        150        160        170        180
CTCTCCTGCA GGGCCAGTCA GAGTGTTAGC AGCTCCTTAG CCTGGTACCA ACAGAAACCT 190        200        210        220        230        240
GGCCAGGCTC CCAGGCTCCT CATCTATGAT GCATCCAACA GGGCCACTGG CATCCCAGCC 250        260        270        280        290        300
AGGTTCAGTG GCAGTGGGTC TGGGACAGAC TTCACTCTCA CCATCAGCAG CCTAGAGCCT 310        320        330        340        350        360
GAAGATTTTG CAATTTATTA CTGTCAGCAG CGTAGCAACT GGCCTCCGAC GTTCGGCCAA 370        380        390
GGGACCAAGG TGGAAATCAA ACGA......
```

<125M165DAAA light chain amino acid sequence> (SEQ ID NO: 33)
```
         10         20         30         40         50         60
MEAPAQLLFL LLLWLPDTTG EIVLTQSPAT LSLSPGERAT LSCRASQSVS SSLAWYQQKP 70         80         90        100        110        120
GQAPRLLIYD ASNRATGIPA RFSGSGSGTD FTLTISSLEP EDFAIYYCQQ RSNWPPTFGQ

130
GTKVEIKR..
```

In the heavy chain nucleic acid sequence (SEQ ID NO: 30), the boundary between the antibody variable region and the antibody constant region is located between adenine (A) at position 420 and guanine (G) at position 421. In the heavy chain amino acid sequence (SEQ ID NO: 31), the boundary between the antibody variable region and the antibody constant region is located between serine (S) at position 140 and alanine (A) at position 141. Furthermore, in the heavy chain nucleic acid sequence (SEQ ID NO: 30), the boundary between the signal sequence and the antibody variable region is located between thymine (T) at position 57 and cytosine (C) at position 58. In the heavy chain amino acid sequence (SEQ ID NO: 31), the boundary between the signal sequence and the antibody variable region is located between cysteine (C) at position 19 and glutamine (Q) at position 20.

Accordingly, the variable region in the 125M165DAAA antibody heavy chain has the nucleic acid sequence (SEQ ID NO: 30) ranging from cytosine (C) at position 58 to adenine (A) at position 420. Further, the variable region in the heavy chain has the amino acid sequence (SEQ ID NO: 31) ranging from glutamine (Q) at position 20 to serine (S) at position 140.

In the light chain nucleic acid sequence (SEQ ID NO: 32), the boundary between the antibody variable region and the antibody constant region is located between adenine (A) at position 381 and cytosine (C) at position 382. In the light chain amino acid sequence (SEQ ID NO: 33), the boundary between the antibody variable region and the antibody constant region is located between lysine (K) at position 127 and arginine (R) at position 128. Furthermore, in the light chain nucleic acid sequence (SEQ ID NO: 32), the boundary between the signal sequence and the antibody variable region is located between adenine (A) at position 60 and guanine (G) at position 61. In the light chain amino acid sequence (SEQ ID NO: 33), the boundary between the signal sequence and the antibody variable region is located between glycine (G) at position 20 and glutamic acid (E) at position 21.

Accordingly, the variable region in the 125M165DAAA antibody light chain has the nucleic acid sequence (SEQ ID NO: 32) ranging from guanine (G) at position 61 to adenine (A) at position 381. Further, the variable region in the light chain has the amino acid sequence (SEQ ID NO: 33) ranging from glutamic acid (E) at position 21 to lysine (K) at position 127.

DNAs encoding the 125M96ABA heavy chain variable region and the light chain variable region and the amino acid sequences of the heavy chain variable region and the light chain variable region are each shown below.

```
<125M96ABA heavy chain nucleic acid sequence> (SEQ ID NO: 34)
         10         20         30         40         50         60
ATGAAGCACC TGTGGTTCTT CCTCCTGCTG GTGGCGGCTC CCAGATGGGT CCTGTCCCAA 70         80         90        100        110        120
CTGCAGCTGC AGGAGTCGGG CCCAGGACTG GTGAAGCCTT CGGAGACCCT GTCCCTCACC 130        140        150        160        170        180
TGCACTGTCT CTGGTGGCTC CATCAGCACT AGTAGTTACT ACTGGGGCTG GATCCGCCAG 190        200        210        220        230        240
CCCCCCGGGA AGGGCCTGGA ATGGATTGGG ACTATCTATT ATAATGGGAG CACCTACTAC 250        260        270        280        290        300
AGCCCGTCCC TCAAGAGTCG AGTCAGTATA TCCGTAGACA CGTCCAAGAA CCAGTTCTCC 310        320        330        340        350        360
CTGAAGCTGA GCTCTGTGAC CGCCGCAGAC ACGTCTGTGT ATTACTGTGC GAGACAAGGT 370        380        390        400        410        420
TACGATATTA AAATCAATAT AGACGTCTGG GGCCAAGGGA CCACGGTCAC CGTCTCCTCA

430
GCTAGC....

<125M96ABA heavy chain amino acid sequence> (SEQ ID NO: 35)
         10         20         30         40         50         60
MKHLWFFLLL VAAPRWVLSQ LQLQESGPGL VKPSETLSLT CTVSGGSIST SSYYWGWIRQ 70         80         90        100        110        120
PPGKGLEWIG TIYYNGSTYY SPSLKSRVSI SVDTSKNQFS LKLSSVTAAD TSVYYCARQG 130        140        150
YDIKINIDVW GQGTTVTVSS AS........

<125M96ABA light chain nucleic acid sequence> (SEQ ID NO: 36)
         10         20         30         40         50         60
ATGGAAGCCC CAGCTCAGCT TCTCTTCCTC CTGCTACTCT GGCTCCCAGA TACCACCGGA 70         80         90        100        110        120
GAAATTGTGT TGACACAGTC TCCAGCCACC CTGTCTTTGT CTCCAGGGGA AAGAGCCACC 130        140        150        160        170        180
CTCTCCTGCA GGGCCAGTCA GAGTGTTAGC AGCTACTTAG CCTGGTACCA ACAGAAACCT 190        200        210        220        230        240
GGCCAGGCTC CCAGGCTCCT CATCTATGTT GCATCCAACA GGGCCACTGG CATCCCAGCC 250        260        270        280        290        300
AGGTTCAGTG GCAGTGGGTC TGGGACAGAC TTCACTCTCA CCATCAGCAG CCTAGAGCCT 310        320        330        340        350        360
GAAGATTTTG CAGTTTATTA CTGTCAGCAG CGTAGCAACT GGCCGCTCAC TTTCGGCGGA 370        380        390
GGGACCAAGG TGGAGATCAA ACGA......

<125M96ABA light chain amino acid sequence> (SEQ ID NO: 37)
         10         20         30         40         50         60
MEAPAQLLFL LLLWLPDTTG EIVLTQSPAT LSLSPGERAT LSCRASQSVS SYLAWYQQKP 70         80         90        100        110        120
```

-continued
GQAPRLLIYV ASNRATGIPA RFSGSGSGTD FTLTISSLEP EDFAVYYCQQ RSNWPLTFGG
         130
GTKVEIKR..

In the heavy chain nucleic acid sequence (SEQ ID NO: 34), the boundary between the antibody variable region and the antibody constant region is located between adenine (A) at position 420 and guanine (G) at position 421. In the heavy chain amino acid sequence (SEQ ID NO: 35), the boundary between the antibody variable region and the antibody constant region is located between serine (S) at position 140 and alanine (A) at position 141. Furthermore, in the heavy chain nucleic acid sequence (SEQ ID NO: 34), the boundary between the signal sequence and the antibody variable region is located between cytosine (C) at position 57 and cytosine (C) at position 58. In the heavy chain amino acid sequence (SEQ ID NO: 35), the boundary between the signal sequence and the antibody variable region is located between serine (S) at position 19 and glutamine (Q) at position 20.

Accordingly, the variable region in the 125M96ABA antibody heavy chain has the nucleic acid sequence (SEQ ID NO: 34) ranging from cytosine (C) at position 58 to adenine (A) at position 420. Further, the variable region in the heavy chain has the amino acid sequence (SEQ ID NO: 35) ranging from glutamine (Q) at position 20 to serine (S) at position 140.

In the light chain nucleic acid sequence (SEQ ID NO: 36), the boundary between the antibody variable region and the antibody constant region is located between adenine (A) at position 381 and cytosine (C) at position 382. In the light chain amino acid sequence (SEQ ID NO: 37), the boundary between the antibody variable region and the antibody constant region is located between lysine (K) at position 127 and arginine (R) at position 128. Furthermore, in the light chain nucleic acid sequence (SEQ ID NO: 36), the boundary between the signal sequence and the antibody variable region is located between adenine (A) at position 60 and guanine (G) at position 61. In the light chain amino acid sequence (SEQ ID NO: 37), the boundary between the signal sequence and the antibody variable region is located between glycine (G) at position 20 and glutamic acid (E) at position 21.

Accordingly, the variable region in the 125M165DAAA antibody light chain has the nucleic acid sequence (SEQ ID NO: 36) ranging from guanine (G) at position 61 to adenine (A) at position 381. Further, the variable region in the light chain has the amino acid sequence (SEQ ID NO: 37) ranging from glutamic acid (E) at position 21 to lysine (K) at position 127.

DNAs encoding the 125N26F6AA heavy chain variable region and the light chain variable region and the amino acid sequences of the heavy chain variable region and the light chain variable region are each shown below.

```
<125N26F6AA heavy chain nucleic acid sequence> (SEQ ID NO: 38)
         10         20         30         40         50         60
ATGGAGTTTG GCTGAGCTG GGTTTTCCTC GTTGCTCTTT TAAGAGGTGT CGAGTGTCAG 70         80         90        100        110        120
GTGCAGTTGG TGGAGTCTGG GGGAGGCGTG GTCCAGCCTG GGAGGTCCCT GAGACTCTCC 130        140        150        160        170        180
TGTGCAGCGT CTGGATTCAC CTTCAGTCAC TATGGCATGC ACTGGGTCCG CCAGGCTCCA 190        200        210        220        230        240
GGCAAGGGGC TGGAGTGGGT GGCACTTATA TGGTATGATG GAAGTAATAA ATACTATGCA 250        260        270        280        290        300
GACTCCGTGA AGGGCCGATT CACCATCTCC AGAGACAATT CCAAGAACAC GCTGTATCTG 310        320        330        340        350        360
CAAATGAACA GCCTGAGAGC CGAGGACACG GCTGTGTATT ACTGTGCGAG AGATCCCTTA 370        380        390        400        410        420
GCAGCTGGTA CGTCCTACTT TGACTACTGG GGCCAGGGAA CCCTGGTCAC CGTCTCCTCA

430
GCTAGC....

<125N26F6AA heavy chain amino acid sequence> (SEQ ID NO: 39)
         10         20         30         40         50         60
MEFGLSWVFL VALLRGVQCQ VQLVESGGGV VQPGRSLRLS CAASGFTFSH YGMHWVRQAP 70         80         90        100        110        120
GKGLEWVALI WYDGSNKYYA DSVKGRFTIS RDNSKNTLYL QMNSLRAEDT AVYYCARDPL 130        140        150
AAGTSYFDYW GQGTLVTVSS AS........

<125N26F6AA light chain nucleic acid sequence> (SEQ ID NO: 40)
         10         20         30         40         50         60
ATGTCGCCAT CACAACTCAT TGGGTTTCTG CTGCTCTGGG TTCCAGCCTC CAGGGGTGAA 70         80         90        100        110        120
ATTGTGCTGA CTCAGTCTCC AGACTTTCAG TCTGTGACTC CAAAGGAGAA AGTCACCATC
```

-continued

```
          130        140        150        160        170        180
    ACCTGCCGGG CCAGTCAGAG CATTGGTAGT AGCTTACACT GGTACCAGCA GAAACCAGAT 190        200        210        220        230        240
    CAGTCTCCAA AGCTCCTCAT CAAGTATGCT TCCCAGTCCT TCTCAGGGGT CCCCTCGAGG 250        260        270        280        290        300
    TTCAGTGGCA GTGGATCTGG GACAGATTTC ACCCTCACCA TCAATAGCCT GGAAGCTGAA 310        320        330        340        350        360
    GATGCTGCAG CGTATTACTG TCATCAGAGT AGTAGTTTAC CATTCACTTT CGGCCCTGGG 370        380
    ACCAAAGTGG ATATCAAACG A

<125N26F6AA light chain amino acid sequence> (SEQ ID NO: 41)
           10         20         30         40         50         60
    MSPSQLIGFL LLWVPASRGE IVLTQSPDFQ SVTPKEKVTI TCRASQSIGS SLHWYQQKPD 70         80         90        100        110        120
    QSPKLLIKYA SQSFSGVPSR FSGSGSGTDF TLTINSLEAE DAAAYYCHQS SSLPFTFGPG

130
    TKVDIKR...
```

In the heavy chain nucleic acid sequence (SEQ ID NO: 38), the boundary between the antibody variable region and the antibody constant region is located between adenine (A) at position 420 and guanine (G) at position 421. In the heavy chain amino acid sequence (SEQ ID NO: 39), the boundary between the antibody variable region and the antibody constant region is located between serine (S) at position 140 and alanine (A) at position 141. Furthermore, in the heavy chain nucleic acid sequence (SEQ ID NO: 38), the boundary between the signal sequence and the antibody variable region is located between thymine (T) at position 57 and cytosine (C) at position 58. In the heavy chain amino acid sequence (SEQ ID NO: 39), the boundary between the signal sequence and the antibody variable region is located between cysteine (C) at position 19 and glutamine (Q) at position 20.

Accordingly, the variable region in the 125M96ABA antibody heavy chain has the nucleic acid sequence (SEQ ID NO: 38) ranging from cytosine (C) at position 58 to adenine (A) at position 420. Further, the variable region in the heavy chain has the amino acid sequence (SEQ ID NO: 39) ranging from glutamine (Q) at position 20 to serine (S) at position 140.

In the light chain nucleic acid sequence (SEQ ID NO: 40), the boundary between the antibody variable region and the antibody constant region is located between adenine (A) at position 388 and cytosine (C) at position 389. In the light chain amino acid sequence (SEQ ID NO: 41), the boundary between the antibody variable region and the antibody constant region is located between lysine (K) at position 126 and arginine (R) at position 127. Furthermore, in the light chain nucleic acid sequence (SEQ ID NO: 40), the boundary between the signal sequence and the antibody variable region is located between thymine (T) at position 57 and guanine (G) at position 58. In the light chain amino acid sequence (SEQ ID NO: 41), the boundary between the signal sequence and the antibody variable region is located between glycine (G) at position 19 and glutamic acid (E) at position 20.

Accordingly, the variable region in the 125M96ABA antibody light chain has the nucleic acid sequence (SEQ ID NO: 40) ranging from guanine (G) at position 58 to adenine (A) at position 388. Further, the variable region in the light chain has the amino acid sequence (SEQ ID NO: 41) ranging from glutamic acid (E) at position 20 to lysine (K) at position 126.

DNAs encoding the 125Q47BA heavy chain variable region and the light chain variable region and the amino acid sequences of the heavy chain variable region and the light chain variable region are each shown below.

```
    <125Q47BA heavy chain nucleic acid sequence> (SEQ ID NO: 42)
           10         20         30         40         50         60
    ATGGAGTTTG GGCTGAGCTG GCTTTTTCTT GTGGCTATTT TAAAAGGTGT CCAGTGTGAG 70         80         90        100        110        120
    GTGCAGCTGT TGGAGTCTGG GGGAGGCTTG GTACAGCCTG GGGGGTCCCT GAGACTCTCC 130        140        150        160        170        180
    TGTGCAGCCT CTGGATTCAC CTTTAGCAGC TATGCCATGA GCTGGGTCCG CCAGGCTCCA 190        200        210        220        230        240
    GGGAAGGGGC TGGAGTGGGT CTCAGATATT AGTGGTAGTG GTGGTTACAC ATACTACGCA 250        260        270        280        290        300
    GACTCCGTGA AGGGCCGGTT CACCATCTCC AGAGACAATT CCAAGAACAC GCTGTATCTG 310        320        330        340        350        360
    CAAATGAACA GCCTGAGAGC CGAGGACACG GCCGTATATT ACTGTGCGAA AACAGGCGAT 370        380        390        400        410        420
    GGTTCGGGGA GTTATTCCCC TGACTCCTGG GGCCAGGGAA CCCTGGTCAC CGTCTCCTCA
```

```
        430
GCTAGC....

<125Q47BA heavy chain amino acid sequence> (SEQ ID NO: 43)
        10         20         30         40         50         60
MEFGLSWLFL VAILKGVQCE VQLLESGGGL VQPGGSLRLS CAASGFTFSS YAMTWVRQAP 70         80         90        100        110        120
GKGLEWVSDI SGSGGYTYYA DSVKGRFTIS RDNSKNTLYL QMNSLRAEDT AVYYCAKTGA 130        140        150
GSGSYSPDSW GQGTLVTVSS AS........

<125Q47BA light chain nucleic acid sequence> (SEQ ID NO: 44)
        10         20         30         40         50         60
ATGGACATGA GGGTCCTCGC TCAGCTCCTG GGGCTCCTGC TGCTCTGTTT CCCAGGTGCC 70         80         90        100        110        120
AGATGTGACA TCCAGATGAC CCAGTCTCCA TCCTCACTGT CTGCATCTGT AGGAGACAGA 130        140        150        160        170        180
GTCACCATCA CTTGTCGGGC GAGTCAGGGT ATTAGCAGCT GGTTAGCCTG GTATCAGCAG 190        200        210        220        230        240
AAACCAGAGA AAGCCCCTAA GTCCCTGATC TATGCTGCAT CCAGTTTGCA AAGTGGGGTC 250        260        270        280        290        300
CCATCAAGGT TCAGCGGCAG TGGATCTGGG ACAGATTTCA CTCTCACCAT CAGCAGCCTG 310        320        330        340        350        360
CAGCCTGAAG ATTTTGCAAC TTATTACTGC AACAGTATA ATAGTTACCC GTACACTTTT 370        380        390
GGCCAGGGGA CCAAGCTGGA GATCAAACGA <125Q47BA light chain amino acid sequence> (SEQ ID NO: 45)
        10         20         30         40         50         60
MDMRVLAQLL GLLLLCFPGA RCDIQMTQSP SSLSASVGDR VTITCRASQG ISSWLAWYQQ 70         80         90        100        110        120
KPEKAPKSLI YAASSLQSGV PSRFSGSGSG TDFTLTISSL QPEDFATYYC QQYNSYPYTF

130
GQGTKLEIKR
```

In the heavy chain nucleic acid sequence (SEQ ID NO: 42), the boundary between the antibody variable region and the antibody constant region is located chain adenine (A) at position 420 and guanine (G) at position 421. In the heavy chain amino acid sequence (SEQ ID NO: 43), the boundary between the antibody variable region and the antibody constant region is located between serine (S) at position 140 and alanine (A) at position 141. Furthermore, in the heavy chain nucleic acid sequence (SEQ ID NO: 42), the boundary between the signal sequence and the antibody variable region is located between thymine (T) at position 57 and guanine (G) at position 58. In the heavy chain amino acid sequence (SEQ ID NO: 43), the boundary between the signal sequence and the antibody variable region is located between cysteine (C) at position 19 and glutamic acid (E) at position 20.

Accordingly, the variable region in the 125Q47BA antibody heavy chain has the nucleic acid sequence (SEQ ID NO: 42) ranging from guanine (G) at position 58 to adenine (A) at position 420. Further, the variable region in the heavy chain has the amino acid sequence (SEQ ID NO: 43) ranging from glutamic acid (E) at position 20 to serine (S) at position 140.

In the light chain nucleic acid sequence (SEQ ID NO: 44), the boundary between the antibody variable region and the antibody constant region is located between adenine (A) at position 387 and cytosine (C) at position 388. In the light chain amino acid sequence (SEQ ID NO: 45), the boundary between the antibody variable region and the antibody constant region is located between lysine (K) at position 129 and arginine (R) at position 130. Furthermore, in the light chain nucleic acid sequence (SEQ ID NO: 44), the boundary between the signal sequence and the antibody variable region is located between thymine (T) at position 66 and guanine (G) at position 67. In the light chain amino acid sequence (SEQ ID NO: 45), the boundary between the signal sequence and the antibody variable region is located between cysteine (C) at position 22 and aspartic acid (D) at position 23.

Accordingly, the variable region in the 125Q47BA antibody light chain has the nucleic acid sequence (SEQ ID NO: 44) ranging from guanine (G) at position 67 to adenine (A) at position 387. Further, the variable region in the light chain has the amino acid sequence (SEQ ID NO: 45) ranging from aspartic acid (D) at position 23 to lysine (K) at position 129.

DNAs encoding the 125Q54AAAA heavy chain variable region and the light chain variable region and the amino acid sequences of the heavy chain variable region and the light chain variable region are each shown below.

```
<125Q54AAAA heavy chain nucleic acid sequence> (SEQ ID NO: 46)
         10         20         30         40         50         60
ATGGAGTTTG GGCTGAGCTG GCTTTTTCTT GTGGCTATTT TAAAAGGTGT CCAGTGTGAG 70         80         90        100        110        120
GTGCAGCTGT TGGAGTCTGG GGGAGGCTTG GTACAGCCTG GGGGGTCCCT GAGACTCTCC 130        140        150        160        170        180
TGTGCAGCCT CTGGATTCAC CTTTAGCAGC TATGCCATGA GCTGGGTCCG CCAGGCTCCA 190        200        210        220        230        240
GGGAAGGGGC TGGAGTGGGT CTCAGATATT AGTGGTAGTG GTGGTTACAC ATACTACGCA 250        260        270        280        290        300
GACTCCGTGA AGGGCCGGTT CACCATCTCC AGAGACAATT CCAAGAACAC GCTGTATCTG 310        320        330        340        350        360
CAAATGAACA GCCTGAGAGC CGAGGACACG GCCGTATATT ACTGTGCGAA AACAGGCGAT 370        380        390        400        410        420
GGTTCGGGGA GTTATTCCCC TGACTCCTGG GGCCAGGGAA CCCTGGTCAC CGTCTCCTCA

430
GCTAGC....

<125Q54AAAA heavy chain amino acid sequence> (SEQ ID NO: 47)
         10         20         30         40         50         60
MEFGLSWLFL VAILKGVQCE VQLLESGGGL VQPGGSLRLS CAASGFTFSS YAMSWVRQAP 70         80         90        100        110        120
GKGLEWVSDI SGSGGYTYYA DSVKGRFTIS RDNSKNTLYL QMNSLRAEDT AVYYCAKTGD 130        140        150
GSGSYSPDSW GQGTLVTVSS AS........

<125Q54AAAA light chain nucleic acid sequence> (SEQ ID NO: 48)
         10         20         30         40         50         60
ATGGACATGA GGGTCCTCGC TCAGCTCCTG GGGCTCCTGC TGCTCTGTTT CCCAGGTGCC 70         80         90        100        110        120
AGATGTGACA TCCAGATGAC CCAGTCTCCA TCCTCACTGT CTGCATCTGT AGGAGACAGA 130        140        150        160        170        180
GTCACCATCA CTTGTCGGGC GAGTCAGGGT ATTAGCAGGT GGTTAGCCTG GTATCAGCAG 190        200        210        220        230        240
AAACCAGAGA AAGCCCCTAA GTCCCTGATC TATGCTGCAT CCAGTTTGCA AAGTGGGGTC 250        260        270        280        290        300
CCATCAAGGT TCAGCGGCAG TGGATCTGGG ACAGATTTCA CTCTCACCAT CAGCAGCCTG 310        320        330        340        350        360
CAGCCTGAAG ATTTTGCAAC TTATTACTGC CAACAGTATA ATAGTTACCC GTACACTTTT 370        380        390
GGCCAGGGGA CCAAGCTGGA GATCAAACGA <125Q54AAAA light chain amino acid sequence> (SEQ ID NO: 49)
         10         20         30         40         50         60
MDMRVLAQLL GLLLLCFPGA RCDIQMTQSP SSLSASVGDR VTITCRASQG ISRWLAWYQQ 70         80         90        100        110        120
KPEKAPKSLI YAASSLQSGV PSRFSGSGSG TDFTLTISSL QPEDFATYYC QQYNSYPYTF

130
GQGTKLEIKR
```

In the heavy chain nucleic acid sequence (SEQ ID NO: 46), the boundary between the antibody variable region and the antibody constant region is located between adenine (A) at position 420 and guanine (G) at position 421. In the heavy chain amino acid sequence (SEQ ID NO: 47), the boundary between the antibody variable region and the antibody constant region is located between serine (S) at position 140 and alanine (A) at position 141. Furthermore, in the heavy chain nucleic acid sequence (SEQ ID NO: 46), the boundary between the signal sequence and the antibody variable region is located between thymine (T) at position 57 and guanine (G) at position 58. In the heavy chain amino acid sequence (SEQ ID NO: 47), the boundary between the signal sequence and the antibody variable region is located between cysteine (C) at position 19 and glutamic acid (E) at position 20.

Accordingly, the variable region in the 125Q54AAAA antibody heavy chain has the nucleic acid sequence (SEQ ID NO: 46) ranging from guanine (G) at position 58 to adenine (A) at position 420. Further, the variable region in the heavy chain has the amino acid sequence (SEQ ID NO: 47) ranging from glutamic acid (E) at position 20 to serine (S) at position 140.

In the light chain nucleic acid sequence (SEQ ID NO: 48), the boundary between the antibody variable region and the antibody constant region is located between adenine (A) at position 387 and cytosine (C) at position 388. In the light chain amino acid sequence (SEQ ID NO: 49), the boundary between the antibody variable region and the antibody constant region is located between lysine (K) at position 129 and arginine (R) at position 130. Furthermore, in the light chain nucleic acid sequence (SEQ ID NO: 48), the boundary between the signal sequence and the antibody variable region is located between thymine (T) at position 66 and guanine (G) at position 67. In the light chain amino acid sequence (SEQ ID NO: 49), the boundary between the signal sequence and the antibody variable region is located between cysteine (C) at position 22 and aspartic acid (D) at position 23.

Accordingly, the variable region in the 125Q54AAAA antibody light chain has the nucleic acid sequence (SEQ ID NO: 48) ranging from guanine (G) at position 67 to adenine (A) at position 387. Further, the variable region in the light chain has the amino acid sequence (SEQ ID NO: 49) ranging from aspartic acid (D) at position 23 to lysine (K) at position 129.

DNAs encoding the 125R5AAAA heavy chain variable region and the light chain variable region and the amino acid sequences of the heavy chain variable region and the light chain variable region are each shown below.

```
<125R5AAAA heavy chain nucleic acid sequence> (SEQ ID NO: 50)
         10         20         30         40         50         60
ATGGAGTTTG GGCTGAGCTG GCTTTTTCTT GTGGCTATTT TAAAAGGTGT CCAGTGTGAG 70         80         90        100        110        120
GTGCAGCTGT TGGAGTCTGG GGAGGCTTG GTACAGCCTG GGGGGTCCCT GAGACTCTCC 130        140        150        160        170        180
TGTGCAGCCT CTGGATTCAC CTTTAGCAGC TATGCCATGA GCTGGGTCCG CCAGGCTCCA 190        200        210        220        230        240
GGGAAGGGGC TGGAGTGGGT CTCAGATATT AGTGGTAGTG GTGGTTACAC ATACTACGCA 250        260        270        280        290        300
GACTCCGTGA AGGGCCGGTT CACCATCTCC AGAGACAATT CCAAGAAAAC GCTGTATCTG 310        320        330        340        350        360
CAAATGAACA GCCTGAGAGC CGAGGACACG GCCGTATATT ACTGTGCGAA AACAGGCGAT 370        380        390        400        410        420
GGTTCGGGGA GTTATTCCCC TGACTACTGG GGCCAGGGAA CCCTGGTCAC CGTCTCCTCA

430
GCTAGC....

<125R5AAAA heavy chain amino acid sequence> (SEQ ID NO: 51)
         10         20         30         40         50         60
MEFGLSWLFL VAILKGVQCE VQLLESGGGL VQPGGSLRLS CAASGFTFSS YAMSWVRQAP 70         80         90        100        110        120
GKGLEWVSDI SGSGGYTYYA DSVKGRFTIS RDNSKKTLYL QMNSLRAEDT AVYYCAKTGD 130        140        150
GSGSYSPDYW GQGTLVTVSS AS........

<125R5AAAA light chain nucleic acid sequence> (SEQ ID NO: 52)
         10         20         30         40         50         60
ATGGACATGA GGGTCCTCGC TCAGCTCCTG GGGCTCCTGC TGCTCTGTTT CCCAGGTGCC 70         80         90        100        110        120
AGATGTGACA TCCAGATGAC CCAGTCTCCA TCCTCACTGT CTGCATCTGT AGGAGACAGA 130        140        150        160        170        180
GTCACCATCA CTTGTCGGGC GAGTCAGGGT ATTAGCAGCT GGTTAGCCTG GTATCAGCAG 190        200        210        220        230        240
AAACCAGAGA AAGCCCCTAA GTCCCTGATC TATGCTGCAT CCAGTTTGCA AAGTGGGGTC 250        260        270        280        290        300
CCATCAAGGT TCAGCGGCAG TGGATCTGGG ACAGATTTCA CTCTCACCAT CAGCAGCCTG 310        320        330        340        350        360
CAGCCTGAAG ATTTTGCAAC TTATTACTGC CAACAGTATA ATAGTTACCC GTACACTTTT 370        380        390
GGCCAGGGGA CCAAGCTGGA GATCAAACGA <125R5AAAA light chain amino acid sequence> (SEQ ID NO: 53)
         10         20         30         40         50         60
MDMRVLAQLL GLLLLCFPGA RCDIQMTQSP SSLSASVGDR VTITCRASQG ISSWLAWYQQ
```

```
         70         80         90        100        110        120
KPEKAPKSLI YAASSLQSGV PSRFSGSGSG TDFTLTISSL QPEDFATYYC QQYNSYPYTF

130
GQGTKLEIKR
```

In the heavy chain nucleic acid sequence (SEQ ID NO: 50), the boundary between the antibody variable region and the antibody constant region is located between adenine (A) at position 420 and guanine (G) at position 421. In the heavy chain amino acid sequence (SEQ ID NO: 51), the boundary between the antibody variable region and the antibody constant region is located between serine (S) at position 140 and alanine (A) at position 141. Furthermore, in the heavy chain nucleic acid sequence (SEQ ID NO: 50), the boundary between the signal sequence and the antibody variable region is located between thymine (T) at position 57 and guanine (G) at position 58. In the heavy chain amino acid sequence (SEQ ID NO: 51), the boundary between the signal sequence and the antibody variable region is located between cysteine (C) at position 19 and glutamic acid (E) at position 20.

Accordingly, the variable region in the 125R5AAAA antibody heavy chain has the nucleic acid sequence (SEQ ID NO: 50) ranging from guanine (G) at position 58 to adenine (A) at position 420. Further, the variable region in the heavy chain has the amino acid sequence (SEQ ID NO: 51) ranging from glutamic acid (E) at position 20 to serine (S) at position 140.

In the light chain nucleic acid sequence (SEQ ID NO: 52), the boundary between the antibody variable region and the antibody constant region is located between adenine (A) at position 387 and cytosine (C) at position 388. In the light chain amino acid sequence (SEQ ID NO: 53), the boundary between the antibody variable region and the antibody constant region is located between lysine (K) at position 129 and arginine (R) at position 130. Furthermore, in the light chain nucleic acid sequence (SEQ ID NO: 52), the boundary between the signal sequence and the antibody variable region is located between thymine (T) at position 66 and guanine (G) at position 67. In the light chain amino acid sequence (SEQ ID NO: 53), the boundary between the signal sequence and the antibody variable region is located between cysteine (C) at position 22 and aspartic acid (D) at position 23.

Accordingly, the variable region in the 125R5AAAA antibody light chain has the nucleic acid sequence (SEQ ID NO: 52) ranging from guanine (G) at position 67 to adenine (A) at position 387. Further, the variable region in the light chain has the amino acid sequence (SEQ ID NO: 53) ranging from aspartic acid (D) at position 23 to lysine (K) at position 129.

EXAMPLE 14

Determination of Full-length Sequences Containing Constant Regions of Human Antibody Heavy Chain and Light Chain Genes Expressed by Hybridomas 125N26F6AA and 125M10AA The DNA nucleotide sequence and the amino acid sequence of the antibody variable region of each antibody were determined in Example 13. For the hybridomas 125N26F6AA and 125M10AA derived from KM mice, full-length sequences containing constant regions were analyzed. cDNA synthesis was performed according to Example 13 using as materials total RNAs prepared from the hybridomas 125N26F6AA and 125M10AA and a SMART RACE cDNA amplification Kit (produced by Becton Dickinson Bioscience Clontech).

1st Strand cDNA Synthesis

| Total RNA | 5 µg/3 µl |
|---|---|
| 3'CDS primer | 1 µl |
| H$_2$O | 1 µl |

A reaction solution with the above composition was incubated at 70° C. for 2 minutes and then the following components were added, followed by 1.5 hours of incubation at 42° C.

| 5 x Buffer | 2 µl |
|---|---|
| DTT | 1 µl |
| dNTP mix | 1 µl |
| PowerScript Reverse Transcriptase | 1 µl |

Furthermore, 50 µl of a tricine buffer was added and then incubation was performed at 72° C. for 7 minutes, thereby obtaining 1st strand cDNA.

To obtain a DNA containing the entire coding region of a constant region, a PCR amplification reaction was performed using the above synthesized cDNA as a template and a primer set of: a synthetic DNA (5' primer) having a sequence binding around the ATG initiation codon at the 5'end of each antibody gene; and a synthetic DNA (3' primer) specifically binding to the 3' non-translation region of a human antibody gene. As a result of the amplification reaction, the full-length sequence of an antibody gene (cDNA) ranging from the ATG initiation codon to the 3' non-translation region, including the stop codon, could be obtained.

The 125N26F6AA heavy chain DNA was amplified by repeating an incubation cycle (94° C. for 15 seconds and 68° C. for 2 minutes) 35 times using a primer set of an H chain 5' primer: N26H5Sal1 (SEQ ID NO: 58) and an H chain 3' primer: H_3UTR1848 (5'-CGGGGTACGTGCCAAG-CATCCTCGTG-3', SEQ ID NO: 74) or a primer set of the H chain 5' primer: N26H5Sal1 (SEQ ID NO: 58) and an H chain 3' primer: H_3UTR1875 (5'-ATGCTGGGCGCCCGG-GAAGTATGTAC-3', SEQ ID NO: 75). Meanwhile, the 125N26F6AA light chain (κ) was amplified using a primer set of an L chain 5' primer: N26KA10 Minor L Bgl (SEQ ID NO: 64) and an L chain 3' primer: L_3UTR_823 (5'-GAAAGAT-GAGCTGGAGGACCGCAATA-3', SEQ ID NO: 76). Except for primers, amplification was performed with a reaction solution having the same composition as that employed in Example 13 (2)-1.

For amplification of the 125M10AA heavy chain DNA, a primer set of an H chain 5' primer: M10H5Sal (SEQ ID NO: 70) and the H chain 3' primer: H_3UTR1848 (SEQ ID NO: 74) or a primer set of the H chain 5' primer: M10H5Sal (SEQ ID NO: 70) and the H chain 3' primer: H_3UTR1875 (SEQ ID NO: 75) was used. For amplification of the 125M10AA light chain (κ) DNA, a primer set of an L chain 5' primer: M10KBgl (SEQ ID NO: 66) and the L chain 3' primer: L__3UTR__823 (SEQ ID NO: 76) were used.

The amplified PCR fragments were separately harvested by ethanol precipitation, harvested by agarose gel electrophoresis, and then purified using a QIAquick Gel Extraction Kit (produced by QIAGEN). The thus purified amplified fragments were separately subcloned into a PCR 4 Blunt-TOPO vector of a Zero Blunt TOPO PCR Cloning Kit (produced by Invitrogen). For the thus obtained clones, sequencing template DNAs were prepared using a TempliPhi DNA Amplification Kit (produced by Amersham Biosciences) including reagents for preparation of sequencing template DNA according to the protocols included therein. Thus, the nucleotide sequences of the insert DNAs were determined. Primers used for analyses of the DNA nucleotide sequences of the human antibody heavy chains were M13FW (SEQ ID NO: 3), M13RV (SEQ ID NO: 4), hh4 (SEQ ID NO: 21), hh1 (5'-CCAAGGGCCCATCGGTCTTCCCCCTGGCAC-3') (SEQ ID NO: 77), CMVH903F (5'-GACACCCTCATGATCTC-CCGGACC-3') (SEQ ID NO: 78), CMVHR1303 (5'-TGT-TCTCCGGCTGCCCATTGCTCT-3') (SEQ ID NO: 79), hh-6 (5'-GGTCCGGGAGATCATGAGGGTGTCCTT-3') (SEQ ID NO: 80), hh-2 (SEQ ID NO: 20), H_3UTR1848 (SEQ ID NO: 74), and H_3UTR1875 (SEQ ID NO: 75). Primers used for analyses of the DNA nucleotide sequences of the human antibody light chains (κ) were M13FW (SEQ ID NO: 3), M13RV (SEQ ID NO: 4), hk-5 (SEQ ID NO: 19), and hk-1 (5'-TGGCTGCACCATCTGTCTTCATCTTC-3') (SEQ ID NO: 81).

DNAs encoding the entire 125N26F6AA antibody heavy chain region and the entire light chain region and the amino acid sequences of the entire heavy chain region and the entire light chain region are each shown below.

```
<125N26F6AA heavy chain nucleic acid sequence> (SEQ ID NO: 82)
         10         20         30         40         50         60
ATGGAGTTTG GGCTGAGCTG GGTTTTCCTC GTTGCTCTTT TAAGAGGTGT CCAGTGTCAG 70         80         90        100        110        120
GTGCAGTTGG TGGAGTCTGG GGGAGGCGTG GTCCAGCCTG GGAGGTCCCT GAGACTCTCC 130        140        150        160        170        180
TGTGCAGCGT CTGGATTCAC CTTCAGTCAC TATGGCATGC ACTGGGTCCG CCAGGCTCCA 190        200        210        220        230        240
GGCAAGGGGC TGGAGTGGGT GGCACTTATA TGGTATGATG GAAGTAATAA ATACTATGCA 250        260        270        280        290        300
GACTCCGTGA AGGGCCGATT CACCATCTCC AGAGACAATT CCAAGAACAC GCTGTATCTG 310        320        330        340        350        360
CAAATGAACA GCCTGAGAGC CGAGGACACG GCTGTGTATT ACTGTGCGAG AGATCCCTTA 370        380        390        400        410        420
GCAGCTGGTA CGTCCTACTT TGACTACTGG GGCCAGGGAA CCCTGGTCAC CGTCTCCTCA 430        440        450        460        470        480
GCCTCCACCA AGGGCCCATC GGTCTTCCCC CTGGCACCCT CCTCCAAGAG CACCTCTGGG 490        500        510        520        530        540
GGCACAGCGG CCCTGGGCTG CCTGGTCAAG GACTACTTCC CCGAACCGGT GACGGTGTCG 550        560        570        580        590        600
TGGAACTCAG GCGCCCTGAC CAGCGGCGTG CACACCTTCC CGGCTGTCCT ACAGTCCTCA 610        620        630        640        650        660
GGACTCTACT CCCTCAGCAG CGTGGTGACC GTGCCCTCCA GCAGCTTGGG CACCCAGACC 670        680        690        700        710        720
TACATCTGCA ACGTGAATCA CAAGCCCAGC AACACCAAGG TGGACAAGAA AGTTGAGCCC 730        740        750        760        770        780
AAATCTTGTG ACAAAACTCA CACATGCCCA CCGTGCCCAG CACCTGAACT CCTGGGGGGA 790        800        810        820        830        840
CCGTCAGTCT TCCTCTTCCC CCCAAAACCC AAGGACACCC TCATGATCTC CCGGACCCCT 850        860        870        880        890        900
GAGGTCACAT GCGTGGTGGT GGACGTGAGC CACGAAGACC CTGAGGTCAA GTTCAACTGG 910        920        930        940        950        960
TACGTGGACG GCGTGGAGGT GCATAATGCC AAGACAAAGC CGCGGGAGGA GCAGTACAAC 970        980        990       1000       1010       1020
AGCACGTACC GTGTGGTCAG CGTCCTCACC GTCCTGCACC AGGACTGGCT GAATGGCAAG 1030       1040       1050       1060       1070       1080
GAGTACAAGT GCAAGGTCTC CAACAAAGCC CTCCCAGCCC CCATCGAGAA AACCATCTCC 1090       1100       1110       1120       1130       1140
```

```
                                -continued
AAAGCCAAAG GGCAGCCCCG AGAACCACAG GTGTACACCC TGCCCCCATC CCGGGATGAG 1150      1160       1170       1180       1190       1200
CTGACCAAGA ACCAGGTCAG CCTGACCTGC CTGGTCAAAG GCTTCTATCC CAGCGACATC 1210      1220       1230       1240       1250       1260
GCCGTGGAGT GGGAGAGCAA TGGGCAGCCG GAGAACAACT ACAAGACCAC GCCTCCCGTG 1270      1280       1290       1300       1310       1320
CTGGACTCCG ACGGCTCCTT CTTCCTCTAC AGCAAGCTCA CCGTGGACAA GAGCAGGTGG 1330      1340       1350       1360       1370       1380
CAGCAGGGGA ACGTCTTCTC ATGCTCCGTG ATGCATGAGG CTCTGCACAA CCACTACACG 1390      1400       1410
CAGAAGAGCC TCTCCCTGTC TCCGGGTAAA TGA <125N26F6AA heavy chain amino acid sequence> (SEQ ID NO: 83)
     10        20         30         40         50         60
MEFGLSWVFL VALLRGVQCQ VQLVESGGGV VQPGRSLRLS CAASGFTFSH YGMHWVRQAP 70        80         90        100        110        120
GKGLEWVALI WYDGSNKYYA DSVKGRFTIS RDNSKNTLYL QMNSLRAEDT AVYYCARDPL 130       140        150        160        170        180
AAGTSYFDYW GQGTLVTVSS ASTKGPSVFP LAPSSKSTSG GTAALGCLVK DYFPEPVTVS 190       200        210        220        230        240
WNSGALTSGV HTFPAVLQSS GLYSLSSVVT VPSSSLGTQT YICNVNHKPS NTKVDKKVEP 250       260        270        280        290        300
KSCDKTHTCP PCPAPELLGG PSVFLFPPKP KDTLMISRTP EVTCVVVDVS HEDPEVKFNW 310       320        330        340        350        360
YVDGVEVHNA KTKPREEQYN STYRVVSVLT VLHQDWLNGK EYKCKVSNKA LPAPIEKTIS 370       380        390        400        410        420
KAKGQPREPQ VYTLPPSRDE LTKNQVSLTC LVKGFYPSDI AVEWESNGQP ENNYKTTPPV 430       440        450        460        470        480
LDSDGSFFLY SKLTVDKSRW QQGNVFSCSV MHEALHNHYT QKSLSLSPGK <125N26F6AA light chain nucleic acid sequence> (SEQ ID NO: 84)
     10        20         30         40         50         60
ATGTCGCCAT CACAACTCAT TGGGTTTCTG CTGCTCTGGG TTCCAGCCTC CAGGGGTGAA 70        80         90        100        110        120
ATTGTGCTGA CTCAGTCTCC AGACTTTCAG TCTGTGACTC CAAAGGAGAA AGTCACCATC 130       140        150        160        170        180
ACCTGCCGGG CCAGTCAGAG CATTGGTAGT AGCTTACACT GGTACCAGCA GAAACCAGAT 190       200        210        220        230        240
CAGTCTCCAA AGCTCCTCAT CAAGTATGCT TCCCAGTCCT TCTCAGGGGT CCCCTCGAGG 250       260        270        280        290        300
TTCAGTGGCA GTGGATCTGG GACAGATTTC ACCCTCACCA TCAATAGCCT GGAAGCTGAA 310       320        330        340        350        360
GATGCTGCAG CGTATTACTG TCATCAGAGT AGTAGTTTAC CATTCACTTT CGGCCCTGGG 370       380        390        400        410        420
ACCAAAGTGG ATATCAAACG AACTGTGGCT GGACCATCTG TCTTCATCTT CCCGCCATCT 430       440        450        460        470        480
GATGAGCAGT TGAAATCTGG AACTGCCTCT GTTGTGTGCC TGCTGAATAA CTTCTATCCC 490       500        510        520        530        540
AGAGAGGCCA AGTACAGTG GAAGGTGGAT AACGCCCTCC AATCGGGTAA CTCCCAGGAG 550       560        570        580        590        600
AGTGTCACAG AGCAGGACAG CAAGGACAGC ACCTACAGCC TCAGCAGCAC CCTGACGCTG 610       620        630        640        650        660
AGCAAAGCAG ACTACGAGAA ACACAAAGTC TACGCCTGCG AAGTCACCCA TCAGGGCCTG 670       680        690        700
AGCTCGCCCG TCACAAAGAG CTTCAACAGG GGAGAGTGTT AG <125N26F6AA light chain amino acid sequence> (SEQ ID NO: 85)
```

```
                         -continued
        10          20          30          40          50          60
MSPSQLIGFL  LLWVPASRGE  IVLTQSPDFQ  SVTPKEKVTI  TCRASQSIGS  SLHWYQQKPD 70          80          90         100         110         120
QSPKLLIKYA  SQSFSGVPSR  FSGSGSGTDF  TLTINSLEAE  DAAAYYCHQS  SSLPFTFGPG 130         140         150         160         170         180
TKVDIKRTVA  APSVFIFPPS  DEQLKSGTAS  VVCLLNNFYP  REAKVQWKVD  NALQSGNSQE 190         200         210         220         230
SVTEQDSKDS  TYSLSSTLTL  SKADYEKHKV  YACEVTHQGL  SSPVTKSFNR  GEC
```

DNAs encoding the entire 125M10AA antibody heavy chain region and the entire light chain region and the amino acid sequences of the entire heavy chain region and the entire light chain region are each shown below.

```
<125M10AA heavy chain nucleic acid sequence> (SEQ ID NO: 86)
        10          20          30          40          50          60
ATGGATCTCA  TGTGCAAGAA  AATGAAGCAC  CTGTGGTTCT  TCCTCCTGCT  GGTGGCGGCT 70          80          90         100         110         120
CCCAGATGGG  TCCTGTCCCA  GCTGCAGGTG  CAGGAGTCGG  GCCCAGGACT  GGTGAAGCCT 130         140         150         160         170         180
TCGGAGACCC  TGTCCCTCAT  CTGCACTGTC  TCTGGTGGCT  CCATCAGGAC  CAGTGGTTAC 190         200         210         220         230         240
TACTGGGGCT  GGTTCCGCCA  GCCCCCAGGG  AAGGGACTGG  AGTGGATTGG  GACTAGTCAT 250         260         270         280         290         300
AATAGTGGGA  GCACCTACTA  CAACCCGTCC  CTCAAGAGTC  GAGTCACCAT  ATCCGTAGAC 310         320         330         340         350         360
ACGTCCAAGA  ACCAGTTCTC  CCTGAAGCTG  AACTCTGTGA  CCGCCGCAGA  CACGGCTGTG 370         380         390         400         410         420
TATTACTGTG  CGAGACAAGG  TTACGATTTT  AAAGTCAATA  TAGACGTCTG  GGGACAAGGG 430         440         450         460         470         480
ACCACGGTCA  CCGTCTCCTC  AGCCTCCACC  AAGGGCCCAT  CGGTCTTCCC  CCTGGCACCC 490         500         510         520         530         540
TCCTCCAAGA  GCACCTCTGG  GGGCACAGCG  GCCCTGGGCT  GCCTGGTCAA  GGACTACTTC 550         560         570         580         590         600
CCCGAACCGG  TGACGGTGTC  GTGGAACTCA  GGCGCCCTGA  CCAGCGGCGT  GCACACCTTC 610         620         630         640         650         660
CCGGCTGTCC  TACAGTCCTC  AGGACTCTAC  TCCCTCAGCA  GCGTGGTGAC  CGTGCCCTCC 670         680         690         700         710         720
AGCAGCTTGG  GCACCCAGAC  CTACATCTGC  AACGTGAATC  ACAAGCCCAG  CAACACCAAG 730         740         750         760         770         780
GTGGACAAGA  AAGTTGAGCC  CAAATCTTGT  GACAAAACTC  ACACATGCCC  ACCGTGCCCA 790         800         810         820         830         840
GCACCTGAAC  TCCTGGGGGG  ACCGTCAGTC  TTCCTCTTCC  CCCCAAAACC  CAAGGACACC 850         860         870         880         890         900
CTCATGATCT  CCCGGACCCC  TGAGGTCACA  TGCGTGGTGG  TGGACGTGAG  CCACGAAGAC 910         920         930         940         950         960
CCTGAGGTCA  AGTTCAACTG  GTACGTGGAC  GGCGTGGAGG  TGCATAATGC  CAAGACAAAG 970         980         990        1000        1010        1020
CCGCGGGAGG  AGCAGTACAA  CAGCACGTAC  CGTGTGGTCA  GCGTCCTCAC  CGTCCTGCAC 1030        1040        1050        1060        1070        1080
CAGGACTGGC  TGAATGGCAA  GGAGTACAAG  TGCAAGGTCT  CCAACAAAGC  CCTCCCAGCC 1090        1100        1110        1120        1130        1140
CCCATCGAGA  AAACCATCTC  CAAAGCCAAA  GGGCAGCCCC  GAGAACCACA  GGTGTACACC 1150        1160        1170        1180        1190        1200
CTGCCCCCAT  CCCGGGATGA  GCTGACCAAG  AACCAGGTCA  GCCTGACCTG  CCTGGTCAAA
```

-continued

```
           1210       1220       1230       1240       1250       1260
       GGCTTCTATC CCAGCGACAT CGCCGTGGAG TGGGAGAGCA ATGGGCAGCC GGAGAACAAC 1270       1280       1290       1300       1310       1320
       TACAAGACCA CGCCTCCCGT GCTGGACTCC GACGGCTCCT TCTTCCTCTA CAGCAAGCTC 1330       1340       1350       1360       1370       1380
       ACCGTGGACA AGAGCAGGTG GCAGCAGGGG AACGTCTTCT CATGCTCCGT GATGCATGAG 1390       1400       1410       1420       1430
       GCTCTGCACA ACCACTACAC GCAGAAGAGC CTCTCCCTGT CTCCGGGTAA ATGA

<125M10AA heavy chain amino acid sequence> (SEQ ID NO: 87)
             10         20         30         40         50         60
       MDLMCKKMKH LWFFLLLVAA PRWVLSQLQV QESGPGLVKP SETLSLICTV SGGSIRTSGY 70         80         90        100        110        120
       YWGWFRQPPG KGLEWIGTSH NSGSTYYNPS LKSRVTISVD TSKNQFSLKL NSVTAADTAV 130        140        150        160        170        180
       YYCARQGYDF KVNIDVWGQG TTVTVSSAST KGPSVFPLAP SSKSTSGGTA ALGCLVKDYF 190        200        210        220        230        240
       PEPVTVSWNS GALTSGVHTF PAVLQSSGLY SLSSVVTVPS SSLGTQTYIC NVNHKPSNTK 250        260        270        280        290        300
       VDKKVEPKSC DKTHTCPPCP APELLGGPSV FLFPPKPKDT LMISRTPEVT CVVVDVSHED 310        320        330        340        350        360
       PEVKFNWYVD GVEVHNAKTK PREEQYNSTY RVVSVLTVLH QDWLNGKEYK CKVSNKALPA 370        380        390        400        410        420
       PIEKTISKAK GQPREPQVYT LPPSRDELTK NQVSLTCLVK GFYPSDIAVE WESNGQPENN 430        440        450        460        470        480
       YKTTPPVLDS DGSFFLYSKL TVDKSRWQQG NVFSCSVMHE ALHNHYTQKS LSLSPGK <125M10AA light chain nucleic acid sequence> (SEQ ID NO: 88)
             10         20         30         40         50         60
       ATGGAAGCCC CAGCTCAGCT TCTCTTCCTC CTGCTACTCT GGCTCCCAGA TACCACCGGA 70         80         90        100        110        120
       GAAATTGTGT TGACACAGTC TCCAGCCACC CTGTCTTTGT CTCCAGGGGA AAGAGCCACC 130        140        150        160        170        180
       CTCTCCTGCA GGGCCAGTCA GAGTGTTAGC AGCTACTTAG CCTGGTACCA ACAGAAACCT 190        200        210        220        230        240
       GGCCAGGCTC CCAGGCTCCT CATCTATGAT GCATCCAACA GGGCCACTGG CATCCCAGCC 250        260        270        280        290        300
       AGGTTCAGTG GCAGTGGGTC TGGGACAGAC TTCACTCTCA CCATCAGCAG CCTAGAGCCT 310        320        330        340        350        360
       GAAGATTTTG CAGTTTATTA CTGTCAGCAG CGTAGCAACT GGCCGCTCAC TTTCGGCGGA 370        380        390        400        410        420
       GGGACCAAGG TGGAGATCAA ACGAACTGTG GCTGCACCAT CTGTCTTCAT CTTCCCGCCA 430        440        450        460        470        480
       TCTGATGAGC AGTTGAAATC TGGAACTGCC TCTGTTGTGT GCCTGCTGAA TAACTTCTAT 490        500        510        520        530        540
       CCCAGAGAGG CCAAAGTACA GTGGAAGGTG GATAACGCCC TCCAATCGGG TAACTCCCAG 550        560        570        580        590        600
       GAGAGTGTCA CAGAGCAGGA CAGCAAGGAC AGCACCTACA GCCTCAGCAG CACCCTGACG 610        620        630        640        650        660
       CTGAGCAAAG CAGACTACGA GAAACACAAA GTCTACGCCT GCGAAGTCAC CCATCAGGGC 670        680        690        700
       CTGAGCTCGC CCGTCACAAA GAGCTTCAAC AGGGGAGAGT GTTAG <125M10AA light chain amino acid sequence> (SEQ ID NO: 89)
             10         20         30         40         50         60
       MEAPAQLLFL LLLWLPDTTG EIVLTQSPAT LSLSPGERAT LSCRASQSVS SYLAWYQQKP 70         80         90        100        110        120
       GQAPRLLIYD ASNRATGIPA RFSGSGSGTD FTLTISSLEP EDFAVYYCQQ RSNWPLTFGG
```

-continued

```
         130        140        150        160        170        180
GTKVEIKRTV AAPSVFIFPP SDEQLKSGTA SVVCLLNNFY PREAKVQWKV DNALQSGNSQ 190        200        210        220        230
ESVTEQDSKD STYSLSSTLT LSKADYEKHK VYACEVTHQG LSSPVTKSFN RGEC
```

EXAMPLE 15

Construction of Vectors for Expression of Recombinant Antibodies

Vectors for expression of 263A17, 125M10AA, 125M165DAAA, 125N26F6AA, and 125Q54AAAA recombinant antibodies were constructed.

For the 263A17, 125M165DAAA, or 125N26F6AA antibody, a plasmid DNA containing the HV chain of each type of obtained antibody was used as a template. Primers used herein were designed to add restriction enzyme sites (Sal I on the 5' terminus and Nhe I on the 3' terminus) to the termini for ligation. Specifically, the primers used herein are as follows.

```
263A17:
5' primer for HV chain:
A33 2-6A2 H VH3-23 Sal I
5'-GCG ACT AAG TCG ACC ATG GAG TTT    (SEQ ID NO: 54)
GGG CTG AGC TG-3'

3' primer for HV chain:
A33 2-6A2 H VH3-23 Nhe I
5'-TGG GCC CTT GGT GCT AGC TGA GGA    (SEQ ID NO: 55)
GAC GGT GAC CG-3'

125M165DAAA:
5' primer for HV chain:
M165H5Sal
5'-AGA GAG AGA GGT CGA CCA CCA TGG    (SEQ ID NO: 56)
AGT TTG GGC TGA GCT GGG TTT-3'

3' primer for HV chain:
M165H3Nhe
5'-AGA GAG AGA GGC TAG CTG AGG AGA    (SEQ ID NO: 57)
CGG TGA CCA GGG TGC-3'

125N26F6AA:
5' primer for HV chain:
N26H5Sal1
5'-AGA GAG AGA GGT CGA CCA CCA TGG    (SEQ ID NO: 58)
AGT TTG GGC TGA GCT GGG TTT-3'

3' primer for HV chain:
N26H3Nhe1
5'-AGA GAG AGA GGC TAG CTG AGG AGA    (SEQ ID NO: 59)
CGG TGA CCA GGG TTC CC-3'
```

The HV of each type of A33 antibody was amplified by PCR (94° C. for 3 minutes→94° C. for 10 seconds and 68° C. for 45 seconds (35 cycles)→72° C. for 7 minutes). The amplified DNA fragment was digested with Sal I and Nhe I. The digested fragment was then introduced into an N5KG1-Val Lark vector (IDEC Pharmaceuticals, a modified vector of N5KG1 (U.S. Pat. No. 6,001,358)) that had been cleaved with the same enzymes. It was confirmed by sequencing with the use of the vector as a template that the inserted sequence was identical to the nucleotide sequence of the subcloned HV as determined by DNA nucleotide sequence analysis.

Subsequently, LV was inserted into the thus obtained plasmid vector into which the HV had been inserted. A plasmid DNA containing the LV chain of each type of obtained antibody was used as a template. Primers used herein were designed to add restriction enzyme sites (Bgl II on the 5' terminus and BsiW I on the 3' terminus) to the termini for ligation. Specifically, primers used herein are as follows.

```
263A17:
5' primer for LV chain:
A33 2-6A2 K L19 Bgl II
5'-ATC ACA GAT CTC TCA CCA TGG ACA    (SEQ ID NO: 60)
TGA GGG TCC CC-3'

3' primer for LV chain:
A33 2-6A2 K L19 BsiW I
5'-ACA GAT GGT GCA GCC ACC GTA CGT    (SEQ ID NO: 61)
TTA ATC TCC AG-3'

125M165DAAA:
5' primer for LV chain:
M165K5L6Bgl2
5'-AGA GAG AGA GAG ATC TCA CCA TGG    (SEQ ID NO: 62)
AAG CCC CAG CTC AGC TTC TCT-3'

3' primer for LV chain:
M165K3L6BsiW1
5'-AGA GAG AGA GCG TAC GTT TGA TTT    (SEQ ID NO: 63)
CCA CCT TGG TCC CTT GGC-3'

125N26F6AA:
5' primer for LV chain:
N26KA10 Minor L Bgl
5'-AGA GAG AGA GAT CTC TCA CCA TGT    (SEQ ID NO: 64)
CGC CAT CAC AAC TCA TTG GG-3'

3' primer for LV chain:
N26KA10 Minor L Bsi
5'-AGA GAG AGA GCG TAC GTT TGA TAT    (SEQ ID NO: 65)
CCA CTT TGG TCC CAG GG-3',
```

The LV of each type of A33 antibody was amplified by PCR (94° C. for 3 minutes→94° C. for 10 seconds and 68° C. for 45 seconds (35 cycles)→72° C. for 7 minutes). The amplified DNA fragment was digested with Bgl II and BsiW I. The digested fragment was then introduced into an N5KG1-HV vector that had been cleaved with the same enzymes. It was confirmed by sequencing with the use of the vector as a template that the inserted sequence was identical to the nucleotide sequence of the subcloned LV as determined by DNA nucleotide sequence analysis.

For the 125M10AA or 125Q54AAAA antibody, a plasmid DNA containing the LV chain of each type of obtained antibody was used as a template. Primers used herein were designed to add restriction enzyme sites (Bgl II on the 5' terminus and BsiW I on the 3' terminus) to the termini for ligation. Specifically, primers used herein are as follows.

```
125M10AA:
5' primer for LV chain: M10KBgl
5'-AGAGAGAGAGAGATCTCACCATGGAAGCCCC    (SEQ ID NO: 66)
AGCTCAGCTTCTCT-3'

3' primer for LV chain: M10KBsi
5'-AGAGAGAGAGCGTACGTTTGATCTCCACCT    (SEQ ID NO: 67)
TGGTCCCTCCG-3'

125Q54AAAA:
5' primer for LV chain: Q54K5Bgl
```

```
-continued
5'-AGAGAGAGAGAGATCTCACCATGGACATGA    (SEQ ID NO: 68)
GGGTCCTCGCTCAGC-3'

3' primer for LV chain: Q54K3Bsi
5'-AGAGAGAGAGCGTACGTTTGATCTCCAGCT    (SEQ ID NO: 69)
TGGTCCCCTGG-3'
```

The LV of each type of A33 antibody was amplified by PCR (94° C. for 3 minutes→94° C. for 10 seconds and 68° C. for 45 seconds (35 cycles)→72° C. for 7 minutes). The amplified DNA fragment was digested with Bgl II and BsiW I. The digested fragment was then introduced into a N5KG1-Val Lark vector that had been cleaved with the same enzymes. It was confirmed by sequencing with the use of the vector as a template that the inserted sequence was identical to the nucleotide sequence of the subcloned LV as determined by DNA nucleotide sequence analysis.

Subsequently, HV was inserted into the thus obtained plasmid vector into which the LV had been inserted. A plasmid DNA containing the HV chain of each type of obtained antibody was used as a template. Primers used herein were designed to add restriction enzyme sites (Sal I on the 5' terminus and Nhe I on the 3' terminus) to the termini for ligation. Specifically, primers used herein are as follows. 125 M10AA:

```
5' primer for HV chain: M10H5Sal
5'-AGA GAG AGA GGT CGA CCA CCA TGG    (SEQ ID NO: 70)
ATC TCA TGT GCA AGA AAA TGA AGC-3'

3' primer for HV chain: M10H3Nhe
5'-AGA GAG AGA GGC TAG CTG AGG AGA    (SEQ ID NO: 71)
CGG TGA CCG TGG TCC CT-3'

125 Q54AAAA:
5' primer for HV chain: Q54H5Sal
5'-AGA GAG AGA GGT CGA CCA CCA TGG    (SEQ ID NO: 72)
AGT TTG GGC TGA GCT GGC TTT-3'

3' primer for HV chain: Q54H3Nhe
5'-AGA GAG AGA GGC TAG CTG AGG AGA    (SEQ ID NO: 73)
CGG TGA CCA GGG TTC CC-3'
```

The HV of each type of A33 antibody was amplified by PCR (94° C. for 3 minutes→94° C. for 10 seconds and 68° C. for 45 seconds (35 cycles)→72° C. for 7 minutes). The amplified DNA fragment was digested with Sal I and Nhe I. The digested fragment was then introduced into an N5KG1-LV vector that had been cleaved with the same enzymes. It was confirmed by sequencing with the use of the vector as a template that the inserted sequence was identical to the nucleotide sequence of the subcloned HV as determined by DNA nucleotide sequence analysis.

Table 5 lists the nucleotide sequences of the synthetic DNAs. Table 6 lists the names of the recombinant vectors and the names of the antibodies produced.

TABLE 5

| No | Primer name | Sequence (5' to 3') | Length | SEQ ID NO: |
|---|---|---|---|---|
| 1 | GPAHvR3Nhe | GCC CTT GGT GCT AGC TGA AGA GAC GGT GAC CAG AGT CCC TTG | 42 | 1 |
| 2 | GPALvR3Bsi | GTG CAC GCC GCT GGT CAG GGC GCC TG | 26 | 2 |
| 3 | M13FW | GTA AAA CGA CGG CCA GTG | 18 | 3 |
| 4 | M13RV | CAG GAA ACA GCT ATG AC | 17 | 4 |
| 5 | GPAHv2F5Sal | AGA GAG AGG TCG ACC CAC CAT GAA CTT TGG GCT GAG CTT AGT T | 43 | 5 |
| 6 | GPALv2FBgl | AGA GAG AGA GAT CTC TCA CCA TGG GCA TCA AGA TGG AGT TTC AG | 44 | 6 |
| 7 | A33-F2 | GCA GAC GAA TTC AAG ACC ATG GTG GGG AAG AT | 32 | 13 |
| 8 | A33-R1 | CTC GAG CGG CCG CTC TGC TGC TGG CCT GTC ACT GGT CGA GGT G | 43 | 14 |
| 9 | GPA-EXCRR2 | CTC GAG CGG CCG CCA GTT CAT GGA GGG AGA TCT GAC G | 37 | 15 |
| 10 | IgG1p | TCT TGT CCA CCT TGG TGT TGC TGG GCT TGT G | 31 | 16 |
| 11 | hk-2 | GTT GAA GCT CTT TGT GAC GGG CGA GC | 26 | 17 |
| 12 | IgG2p/G134 | TGC ACG CCG CTG GTC AGG GCG CCT GAG TTC C | 31 | 18 |
| 13 | hk-5 | AGG CAC ACA ACA GAG GCA GTT CCA GAT TTC | 30 | 19 |
| 14 | hh-2 | GCT GGA GGG CAC GGT CAC CAC GCT G | 25 | 20 |
| 15 | hh-4 | GGT GCC AGG GGG AAG ACC GAT GG | 23 | 21 |
| 16 | A33 2-6A2 H VH3-23 SalI | GCG ACT AAG TCG ACC ATG GAG TTT GGG CTG AGC TG | 35 | 54 |
| 17 | A33 2-6A2 H VH3-23 NheI | TGG GCC CTT GGT GCT AGC TGA GGA GAC GGT GAC CG | 35 | 55 |
| 18 | M165H5Sal | AGA GAG AGA GGT CGA CCA CCA TGG AGT TTG GGC TGA GCT GGG TTT | 45 | 56 |
| 19 | M165H3Nhe | AGA GAG AGA GGC TAG CTG AGG AGA CGG TGA CCA GGG TGC | 39 | 57 |

TABLE 5-continued

| No | Primer name | Sequence (5' to 3') | Length | SEQ ID NO: |
|---|---|---|---|---|
| 20 | N26H5Sal1 | AGA GAG AGA GGT CGA CCA CCA TGG AGT TTG GGC TGA GCT GGG TTT | 45 | 58 |
| 21 | N26H3Nhe1 | AGA GAG AGA GGC TAG CTG AGG AGA CGG TGA CCA GGG TTC CC | 41 | 59 |
| 22 | A33 2-6A2 K L19 BglII | ATC ACA GAT CTC TCA CCA TGG ACA TGA GGG TCC CC | 35 | 60 |
| 23 | A33 2-6A2 K L19 BsiWI | ACA GAT GGT GCA GCC ACC GTA CGT TTA ATC TCC AG | 35 | 61 |
| 24 | M165K5L6Bgl2 | AGA GAG AGA GAG ATC TCA CCA TGG AAG CCC CAG CTC AGC TTC TCT | 45 | 62 |
| 25 | M165K3L6BsiW1 | AGA GAG AGA GCG TAC GTT TGA TTT CCA CCT TGG TCC CTT GGC | 42 | 63 |
| 26 | N26KA10Minor L Bgl | AGA GAG AGA GAT CTC TCA CCA TGT CGC CAT CAC AAC TCA TTG GG | 44 | 64 |
| 27 | N26KA10Minor L Bsi | AGA GAG AGA GCG TAC GTT TGA TAT CCA CTT TGG TCC CAG GG | 41 | 65 |
| 28 | M10KBgl | AGA GAG AGA GAG ATC TCA CCA TGG AAG CCC CAG CTC AGC TTC TCT | 45 | 66 |
| 29 | M10KBsi | AGA GAG AGA GCG TAC GTT TGA TCT CCA CCT TGG TCC CTC CG | 41 | 67 |
| 30 | Q54K5Bgl | AGA GAG AGA GAG ATC TCA CCA TGG ACA TGA GGG TCC TCG CTC AGC | 45 | 68 |
| 31 | Q54K3Bsi | AGA GAG AGA GCG TAC GTT TGA TCT CCA GCT TGG TCC CCT GG | 41 | 69 |
| 32 | M10H5Sal | AGA GAG AGA GGT CGA CCA CCA TGG ATC TCA TGT GCA AGA AAA TGA AGC | 48 | 70 |
| 33 | M10H3Nhe | AGA GAG AGA GGC TAG CTG AGG AGA CGG TGA CCG TGG TCC CT | 41 | 71 |
| 34 | Q54H5Sal | AGA GAG AGA GGT CGA CCA CCA TGG AGT TTG GGC TGA GCT GGC TTT | 45 | 72 |
| 35 | Q54H3Nhe | AGA GAG AGA GGC TAG CTG AGG AGA CGG TGA CCA GGG TTC CC | 41 | 73 |
| 36 | H_3UTR1848 | CGG GGT ACG TGC CAA GCA TCC TCG TG | 26 | 74 |
| 37 | H_3UTR1875 | ATG CTG GGC GCC CGG GAA GTA TGT AC | 26 | 75 |
| 38 | L_3UTR_823 | GAA AGA TGA GCT GGA GGA CCG CAA TA | 26 | 76 |
| 39 | hh-1 | CCA AGG GCC CAT CGG TCT TCC CCC TGG CAC | 30 | 77 |
| 40 | CMVH903F | GAC ACC CTC ATG ATC TCC CGG ACC | 24 | 78 |
| 41 | CMVHR1303 | TGT TCT CCG GCT GCC CAT TGC TCT | 24 | 79 |
| 42 | hh-6 | GGT CCG GGA GAT CAT GAG GGT GTC CTT | 27 | 80 |
| 43 | hk-1 | TGG CTG CAC CAT CTG TCT TCA TCT TC | 26 | 81 |

TABLE 6

| Antibody | Vector name | Subclass | Recombinant antibody name |
|---|---|---|---|
| 263A17 | N5KG1-Val Lark | IgG1 | rec263 |
| 125M10AA | N5KG1-Val Lark | IgG1 | recM10 |
| 125M165DAAA | N5KG1-Val Lark | IgG1 | recM165 |
| 125N26F6AA | N5KG1-Val Lark | IgG1 | recN26 |
| 125Q54AAAA | N5KG1-Val Lark | IgG1 | recQ54 |

EXAMPLE 16

Preparation of Recombinant Antibodies

Host cells were transfected with the vectors for expression of recombinant antibodies constructed in Example 15, thereby preparing recombinant-antibody-expressing cells. Host cells to be used for expression were CHO cells of a dhfr-deficient cell line (ATCC CRL-9096), CHO-Ras (Katakura Y., et al., Cytotechnology, 31: 103-109, 1999), or HEK293T (ATCC CRL-11268), for example.

Host cells were transfected with each type of vector by electroporation, lipofection, or the like. Approximately 2 μg of the antibody expression vector was linearized using restriction enzymes and then subjected to electroporation using a Bio-Rad electrophoreter under conditions of 350 V and 500 μF. $4 \times 10^6$ CHO cells were thus transfected with each type of gene, and then the cells were inoculated on a 96-well culture plate. Lipofection was performed using LipofectAMINE Plus (produced by Gibco BRL) according to the manual included therein. After transfection with such vector, a drug corresponding to the selection marker used in the expression vector was added, and then culture was continued. After confirmation of colonies, antibody-expressing cell lines were selected by the method described in Example 6. Antibody sented by –. Each type of recombinant antibody showed binding to all cells expressing the A33 antigen.

TABLE 7

| Antibody name | COLO205 | LS174T | NCI-H508 | HT-29 |
|---|---|---|---|---|
| Anti-DNP-IgG1 | – | – | – | – |
| cA33 | +++ | +++ | +++ | – |
| rec263 | ++ | ++ | ++ | – |
| recM10 | +++ | +++ | +++ | – |
| recM165 | ++ | ++ | ++ | – |
| recN26 | ++ | +++ | +++ | – |
| recQ54 | +++ | +++ | +++ | – |
| | Half value of the mean fluorescence intensity 45 | Half value of the mean fluorescence intensity 100 | Half value of the mean fluorescence intensity 175 | |
| | 10 <= x < 100 ng/ml; +++ | 10 <= x < 100 ng/ml; +++ | 10 <= x < 100 ng/ml; +++ | |
| | 100 <= x < 1000 ng/ml; ++ | 100 <= x < 1000 ng/ml; ++ | 100 <= x < 1000 ng/ml; ++ | |
| | 1000 <= x < 10000 ng/ml; + | 1000 <= x < 10000 ng/ml; + | 1000 <= x < 10000 ng/ml; + | |
| | No binding; – | No binding; – | No binding; – | | purification was performed from the selected cells by washing twice with PBS after adsorption and then eluting using 20 mM (glycine) sodium citrate and a 50 mM NaCl (pH 2.7) buffeu sing a Mab Select Protein A 3.2×10 cm column (produced by Amersham Pharmacia Biotech). The eluted solution was neutralized with a 50 mM sodium phosphate buffer (pH 7.0). Next, purification was performed using a Hitrap Q HP Sepharose column (produced by Amersham Pharmacia Biotech), which is an anion exchange column, and then similarly performed using a Hitrap SP HP Sepharose column (produced by Amersham Pharmacia Biotech) which is a cation column. The thus prepared antibody solution was substituted with PBS using a dialysis membrane (10000 cut-off produced by Spectrum Laboratories) and then sterilized by filtration using a membrane filter MILLEX-GV (produced by Millipore) with a pore size of 0.22 µm. Thus purified antibodies with purity of at least 95% or higher and with endotoxin levels of 0.1 EU/mg or less endotoxin were obtained. The concentration of each type of recombinant purified anti-A33 antibody was obtained by measurement of absorbance at 280 nm and calculation with 1.4 OD being equivalent to 1 mg/mL (antibody concentration).

EXAMPLE 17

Test of the Reactivity of Recombinant Antibodies

The reactivity of each type of recombinant antibody obtained in Example 16 to A33-antigen-expressing human colorectal cancer cell line COLO205 cells, LS174T cells (ATCC No. CL-188), or NCI-H508 cells (ATCC No. CCL-253) was examined by FCM. The reactivity of human colorectal cancer cell line HT-29 cells (ATCC No. HTB-38) expressing no A33 antigen was also examined as negative control cells. The test method conducted herein was similar to that in Example 9.

Table 7 shows the results. For COLO205 cells, the half value of the mean fluorescence intensity was determined to be 45. For LS174T cells, the half value of the mean fluorescence intensity was determined to be 100. For NCI-H508 cells, the half value of the mean fluorescence intensity was determined to be 175. When an antibody concentration required to reach such value was 10<=x<100 ng/ml, the reactivity was represented by +++, when the same was 100<=x<1000 ng/ml, the reactivity was represented by ++, and when the same was 1000<=x<10000 ng/ml, the reactivity was represented by +. When no binding was observed, the reactivity was repre-

EXAMPLE 18

Competition Test Regarding Each Type of Recombinant Antibody and Mouse Anti-A33 Antibody Whether or not each type of type of recombinant antibody obtained in Example 16 recognizes an epitope similar to that of the mouse anti-A33 antibody was examined by a competition test using FCM. The test method conducted herein was similar to that in Example 10.

Similar to the results for each type of purified monoclonal antibody in Example 10, rec263 and recM10 were classified as "non-blockers," recM165 and recN26 were classified as "blockers," and recQ54 was classified as "a partial blocker." Table 8 shows the results.

TABLE 8

| Antibody name | Inhibition (%) | Classification |
|---|---|---|
| cA33 | 94.6 | Blocker |
| rec263 | 15.3 | Non-blocker |
| recM10 | 0.2 | Non-blocker |
| recM165 | 93.4 | Blocker |
| recN26 | 95.3 | Blocker |
| recQ54 | 44.6 | Partial blocker |

EXAMPLE 19

Test of the Cytotoxicity of Recombinant Antibodies

ADCC and CDC of the recombinant antibodies obtained in Example 16 were determined. In the ADCC assay, 5,000 $^{51}$Cr-labeled target cells (COLO205 or NCI-H508) and 500,000 healthy human peripheral blood mononuclear leukocytes obtained by the method described in Example 11 were cultured in a V-bottom 96-well plate (produced by Coaster) at a total volume of 200 µL with antibody having each concentration at 37° C. in the presence of 5% $CO_2$ for 4 hours.

In the CDC assay, 5000 $^{51}$Cr-labeled target cells (COLO205 or NCI-H508) and human serum-derived complements (produced by Sigma) at a final concentration of 5% were cultured in a V-bottom 96-well plate at a total volume of 200 µL with antibody having each concentration at 37° C. in the presence of 5% $CO_2$ for 4 hours.

The test method conducted herein was similar to that in Example 12.

FIG. 2A to FIG. 2D and Table 9 show the results. In the case of ADCC against COLO205 cells as target cells, the half value of the specific lysis (%) was determined to be 12.5%. In the case of ADCC against NCI-H508 cells as target cells, the half value of the specific lysis (%) was determined to be 30%. When an antibody concentration required to reach such value was 1<=x<10 ng/ml, the cytotoxicity was represented by +++, when the same was 10<=x<100 ng/ml, the cytotoxicity was represented by ++, when the same was 100<=x<1000 ng/ml, the cytotoxicity was represented by +, and when no specific lysis (%) was obtained, the cytotoxicity was represented by –. In the case of CDC against COLO205 cells as target cells, the half value of the specific lysis (%) was determined to be 7%. In the case of CDC against NCI-H508 cells as target cells, the half value of the specific lysis (%) was determined to be 20%. When an antibody concentration required to reach such value was 10<=x<100 ng/ml, the cytotoxicity was represented by +++, when the same was 100<=x<1000 ng/ml, the cytotoxicity was represented by ++, when the same was x>=1000 ng/ml, the cytotoxicity was represented by +, and when no specific lysis (%) was observed, the cytotoxicity was represented by –. In the case of ADC, cA33, recM10, and recQ54 showed high cytotoxicity, while in the case of CDC, recM10 showed high cytotoxicity.

Standard BroadRange (produced by Bio-Rad Laboratories) was also applied to one lane as a marker. The shA33EX-hFc protein was blotted onto a PVDF membrane using Panther Semidry Electroblotter (Daiichi Pure Chemicals) at 150 mA/membrane for 1 hour. The membrane onto which the protein had been blotted was washed using a TBS buffer and TBS (TTBS) containing 0.05% Tween. Blocking was performed using BlockAce (produced by Dainippon Pharmaceutical). Washing was performed twice with TTBS. Each type (1 µg/ml) of antibody purified from 125M10AA, 125Q54AAAA, 125M96ABA, 125Q47BA, and 125R5AAAA hybridomas was caused to react at room temperature for 60 minutes. In the meantime, each type (1 µg/ml) of recombinant antibody including the chimeric anti-A33 antibody, 125M165DAAA (that is, recM165), and 125N26F6AA (that is, recN26), was caused to react at room temperature for 60 minutes. After washing with TTBS, a goat anti-human Kappa chain F(ab')$_2$ antibody (produced by Biosource) labeled with horseradish peroxidase (diluted 1000-fold) was used as an antibody for detection. At this time, streptavidin labeled with horseradish peroxidase (diluted 3000 fold) was also added and caused to react so as to detect markers. After washing twice with TTBS and then once with PBS, band detection was performed using Western blotting detection system ECL-plus (produced by Amersham Biosciences). Chemoluminescence was incorporated using an

TABLE 9

| Antibody name | Cell name | | | |
|---|---|---|---|---|
| | COLO205 | | NCI-H508 | |
| | ADCC | CDC | ADCC | CDC |
| Anti-DNP-IgG1 | – | – | – | – |
| cA33 | +++ | ± | ++ | ++ |
| rec263 | ++ | ++ | ++ | ++ |
| recM10 | +++ | +++ | ++ | +++ |
| recM165 | ++ | + | ++ | ++ |
| recN26 | ++ | + | ++ | ++ |
| recQ54 | +++ | ++ | ++ | ++ |
| | Half value of specific lysis (%) 12.5% 1 <= x < 10 ng/ml; +++ 10 <= x < 100 ng/ml; ++ 100 <= x < 1000 ng/ml; + No specific lysis; – | Half value of specific lysis (%) 7% 10 <= x < 100 ng/ml; +++ 100 <= x < 1000 ng/ml; ++ 1000 <= x < 10000 ng/ml; + x >= 10000 ng/ml; ± No specific lysis; – | Half value of specific lysis (%) 30% 1 <= x < 10 ng/ml; +++ 10 <= x < 100 ng/ml; ++ 100 <= x < 1000 ng/ml; + No specific lysis; – | Half value of specific lysis (%) 20% 10 <= x < 100 ng/ml; +++ 100 <= x < 1000 ng/ml; ++ 1000 <= x < 10000 ng/ml; + x >= 10000 ng/ml; ± No specific lysis; – |

EXAMPLE 20

Western Blot Analysis of the Purified Antibodies and Recombinant Antibodies

Mouse anti-A33 and humanized A33 antibodies have been reported to recognize conformational epitopes. Specifically, in the cases of these antibodies, it has been reported that no reactivity was observed via Western blot analysis under reducing conditions (5% β-mercaptoethanol). Hence, Western blot analysis was performed in order to examine the reactivity of the purified human anti-A33 and recombinant antibodies.

The shA33EX-hFc protein prepared in Example 3 was separated by SDS-PAGE using 10% to 20% polyacrylamide gradient gel (produced by Daiichi Pure Chemicals) under reducing (5% β-mercaptoethanol) and non-reducing conditions. At this time, the shA33EX-hFc protein was diluted to 2.5 ng per lane. In the meantime, biotinylated SDS-PAGE image analyzer LAS-100 (produced by Fuji Photo Film) and then image processing was performed.

Figure 3A:
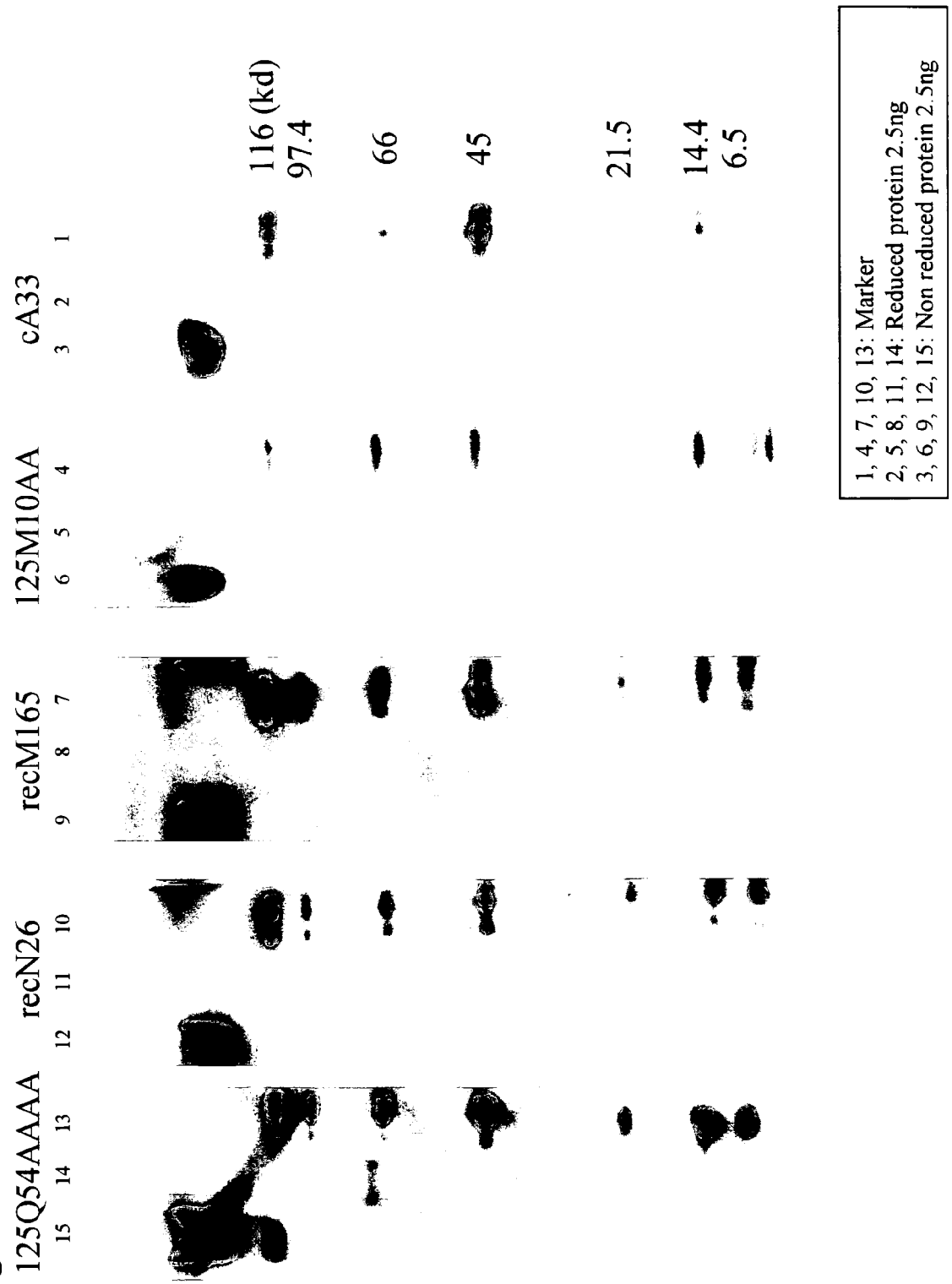
FIG. 3A is a photograph showing the results of Western blot analysis using a purified antibody and recombinant antibodies.
Figure 3B:
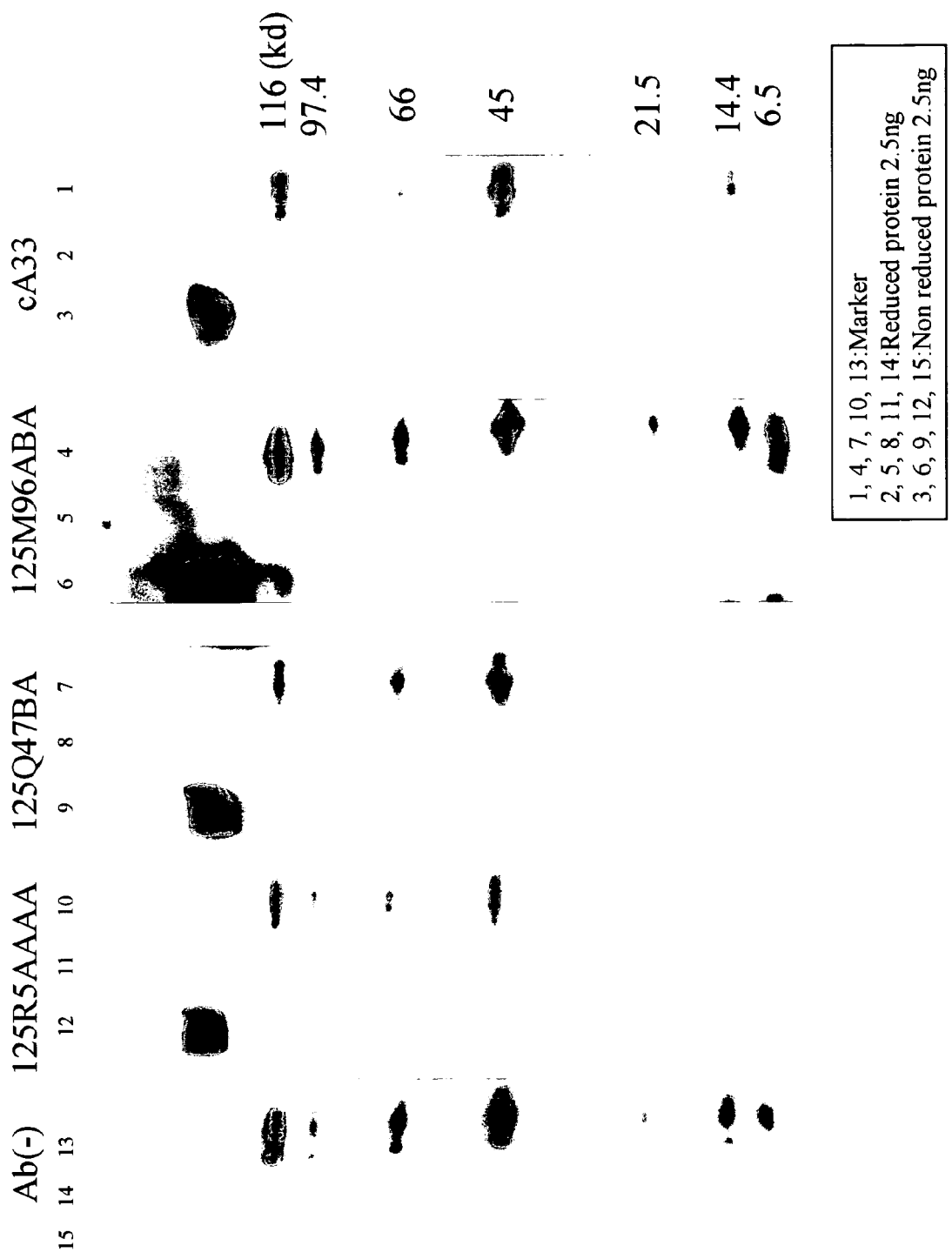
FIG. 3B is a photograph showing the results of Western blot analysis using a purified antibody and recombinant antibodies.

FIG. 3A and FIG. 3B show the results. It was found as a result that only 125Q54AAAA reacted with a protein band of approximately 67 kD even under reducing conditions. In the cases of the other antibodies, reaction was observed only under non-reducing conditions, similar to the case of the chimeric anti-A33 antibody.

EXAMPLE 21

Immunohistochemical Analysis of the Purified Antibodies and Recombinant Antibodies To evaluate whether or not each type of human anti-A33 antibody is equivalent to the chimeric anti-A33 antibody in terms of specificity and selectivity, the reactivity of tumor tissue sections and that of normal tissue sections were analyzed by immunohistochemical analysis.

(1) Fluorescent Labeling of the Purified Antibodies and Recombinant Antibodies

Each type of purified monoclonal antibody prepared in Example 8 was directly labeled with Alexa Fluor™ 488 (produced by Molecular Probe). Each type of recombinant antibody (rec263, 125M10AA, recM165, recN26, and 125Q54AAA) prepared in Example 16 was also directly labeled with the same. Similarly, the chimeric anti-A33 antibody was directly labeled as a positive control and an anti-DNP-IgG1 antibody was directly labeled as a negative control. Fluorescent labeling was performed for the purified and recombinant antibodies as described below. Alexa Fluor™ 488 was bound to each type of anti-A33 antibody prepared in Example 8 or 16 according to the instructions included therein. 50 µl of a 1 M carbonate buffer was added to 2 mg/ml of each type of purified antibody and to 0.5 ml of each type of recombinant antibody. The solutions were mixed with Alexa Fluor™488, followed by 1 hour of reaction at room temperature while stirring of the solutions took place. Hydroxylamine was added to stop the reactions. Each of the mixed solutions was applied to a gel filtration column (NAP5, produced by Amersham Pharmacia Biotech), thereby removing Alexa Fluor™488 that had not bound to the antibodies. 4 to 6 fluorescent substances bound to 1 molecule of antibody under these conditions. The fluorescent-labeled antibodies bound to COLO205 cells and showed binding activity equivalent to those of unlabeled antibodies.

(2) Immunohistochemistry

Tissue sections used herein were frozen human adult colon cancer tissue sections (produced by BioChain), frozen human adult normal colon tissue sections (produced by BioChain), frozen human adult small intestine tissue sections (produced by BioChain), and frozen human adult stomach tissue sections (produced by BioChain). Blocking was performed for 1 to 2 hours at room temperature using PBS containing 10% goat serum (produced by Gibco BRL). Washing was performed twice with PBS. Each type of purified monoclonal or recombinant antibody labeled with Alexa Fluor™488 in Example 21 (1) was caused to react at 1 µg/ml at room temperature for 30 to 60 minutes. Subsequently, the sections were mounted and then observed under a fluorescence microscope (BX51 produced by Olympus). The images were analyzed using DP70 (produced by Olympus).

Figure 4:
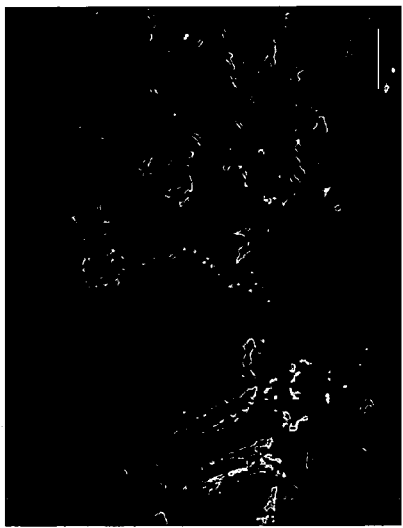
FIG. 4 shows photographs showing the results of immunohistostaining of human colon cancer tissues using a purified antibody and recombinant antibodies (FIG. 4a: chimeric anti-A33 antibody, FIG. 4b: rec263, FIG. 4c: 125M10AA, FIG. 4d: recM165, FIG. 4e: recN26, FIG. 4f: 125 Q54AAA).
Figure 4:
Figure 4:
Figure 4:
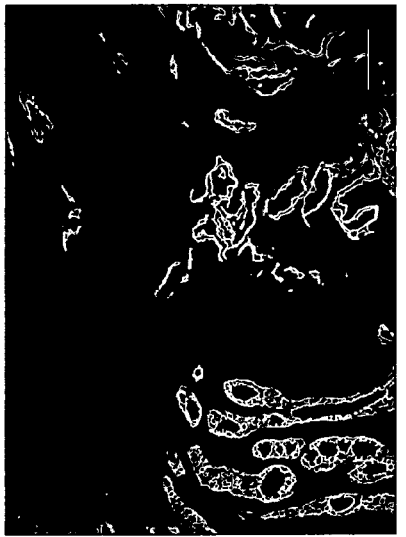
Figure 4:
Figure 4:
Figure 5:
FIG. 5 shows photographs, showing the results of immunohistostaining of human normal small intestine tissues using a purified antibody and recombinant antibodies (FIG. 5a: chimeric anti-A33 antibody, FIG. 5b: rec263, FIG. 5c: 125M10AA, FIG. 5d: recM165, FIG. 5e: recN26, FIG. 5f: 125Q54AAA).
Figure 5:
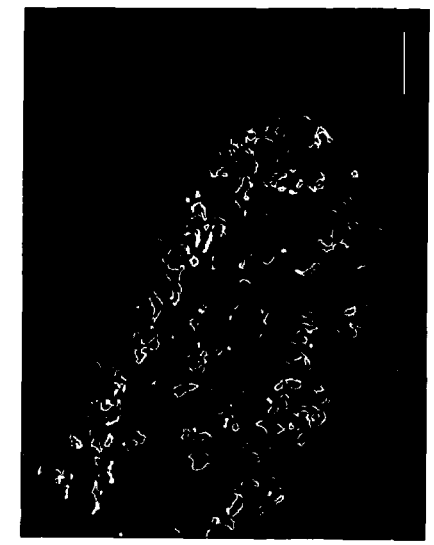
Figure 5:
Figure 5:
Figure 5:
Figure 5:
Figure 6:
FIG. 6 shows photographs showing the results of immunohistostaining of human normal colon tissues using a purified antibody and recombinant antibodies (FIG. 6a:, chimeric anti-A33 antibody, FIG. 6b: rec263, FIG. 6c: 125M10AA, FIG. 6d: recM165, FIG. 6e: recN26, FIG. 6f: 125Q54AAA).
Figure 6:
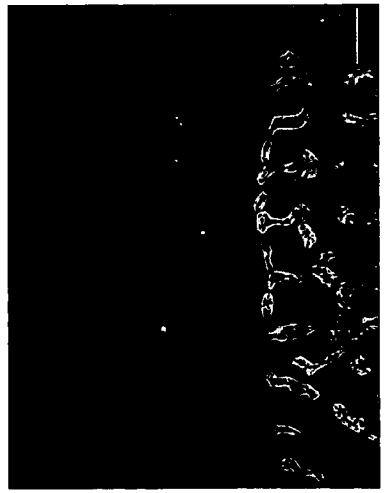
Figure 6:
Figure 6:
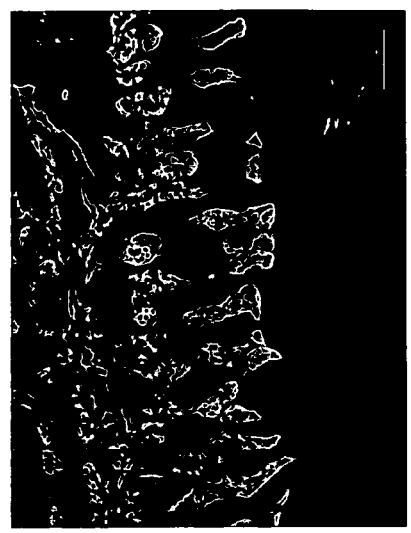
Figure 6:
Figure 6:
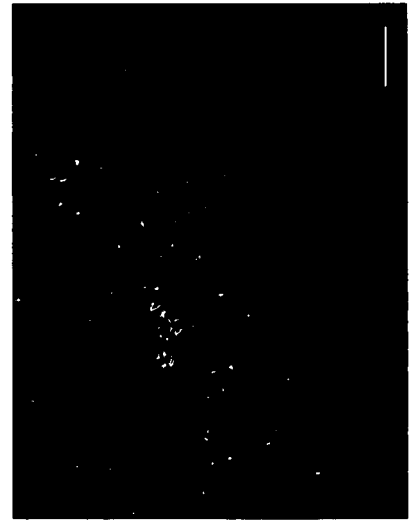

FIGS. 4 to 6 show the results. Similar to the results of immunohistostaining of colorectal cancer tissues as reported by Garin-Chesa P et al. (Int. J. Oncology 1996 9: 465-471), extensive, uniform, and strong staining of glandular epithelium cells or dysplastic gland structures of colon cancer tissues were observed in the cases of the chimeric anti-A33 antibody, rec263, 125M10AA, recM165, recN26, and 125Q54AAA (FIG. 4). Moreover, it was observed that normal small intestine tissues (FIG. 5) and normal colon tissues (FIG. 6) had been stained in a manner similar to that in the case of the chimeric anti-A33 antibody. In contrast, no staining of normal gastric tissues was observed even in the cases of the antibodies, similar to the results of the aforementioned paper. Furthermore, in the case of the anti-DNP-IgG1 antibody as a negative control, staining was not observed in any tissues.

EXAMPLE 22

Effects of Antibodies Purified from Hybridomas and Recombinant Antibodies on Mouse Tumor-bearing Models The effects of the human anti-A33 recombinant antibodies obtained in Example 16 were examined using mouse tumor-bearing models according to the method described below. The cells of colorectal cancer cell lines used herein were COLO205 cells and NCI-H508 cells.

A method for preparing a mouse tumor-bearing model using the COLO205 cell line is described below. The cells of the colorectal cancer cell line COLO205 were subcutaneously engrafted at $5 \times 10^6$/mouse in the dorsal regions of 6-week-old Balb/c nude mice (purchased from CLEA Japan). On days 1, 2, 7, and 10 after the engrafting of the cells, the chimeric anti-A33 or rec263 antibody (dissolved in 200 µl of 1% nude mouse serum-containing PBS) was administered intraperitoneally at 10 µg/mouse or 100 µg/mouse to tumor-bearing mice (10 mice per group). Tumor sizes were measured on days 7, 9, 11, 14, 17, and 21 after the engrafting of the cells. A human anti-DNP-IgG1 antibody was used as a negative control antibody in amounts identical to those of the above antibodies. "Vehicle" denotes 1% nude mouse serum-containing PBS (200 µl) that was used as medium for dissolution upon antibody administration.

A method for preparing a mouse tumor-bearing model using the NCI-H508 cell line is described below. The cells of the colorectal cancer cell line NCI-H508 and Matrigel (produced by Becton Dickinson Bioscience) comprising mouse malignant sarcoma (which improves the survival and proliferation of tumor cells) were subcutaneously engrafted at $1 \times 10^7$/mouse in the dorsal regions of 6-week-old Balb/c nude mice (purchased from CLEA Japan), so that the ratio of NCI-H508 to Matrigel would be 1:1. The chimeric anti-A33 or rec263 antibody (dissolved in 200 µl of 1% nude mouse serum-containing PBS) was administered intraperitoneally at 10 µg/mouse or 100 µg/mouse to tumor-bearing mice (10 mice per group) on days 1, 4, and 7 after the engrafting of the cells. Tumor sizes were measured on days 7, 11, 14, 18, 21, 27, 33, 40, 48, 55, and 62 after the engrafting of the cells. A human anti-DNP-IgG1 antibody was used as a negative control antibody in amounts identical to those of the above antibodies. "Vehicle" denotes 0.1% nude mouse serum-containing PBS (200 µl) that was used as a medium for dissolution upon antibody administration.

FIG. 7 shows the results of the above experiment.

Figure 7A:
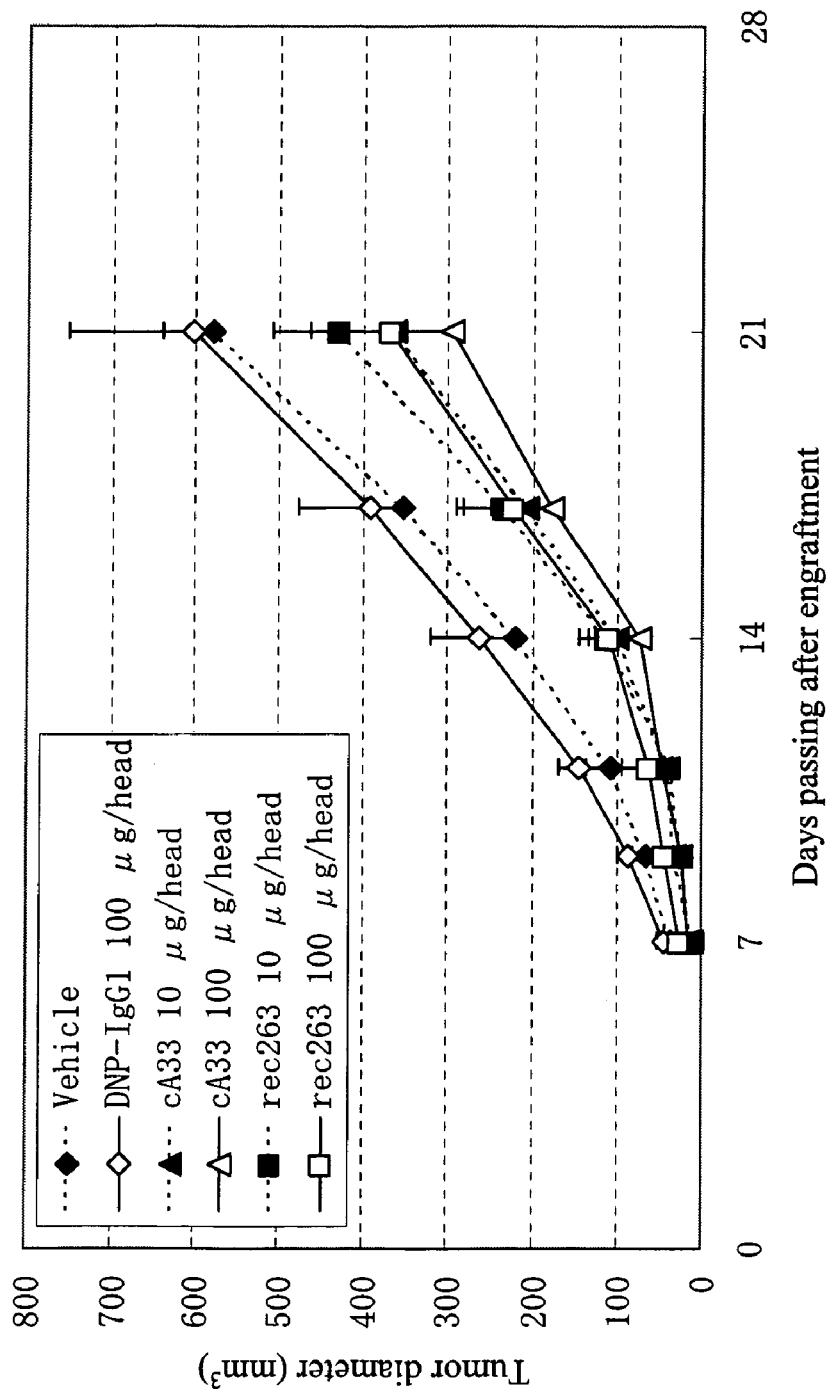
FIG. 7A shows the antitumor effects of recombinant antibodies cA33 and rec263 against a mouse tumor-bearing model wherein COLO205 cells were implanted.

Regarding the mouse line in which the COLO205 cell line had been engrafted, significant tumor suppression ($p<0.05$) was observed on days 7, 9, and 11 after the engrafting of the cells in the case of the group to which the rec263 antibody had been administered at 10 µg/mouse, compared with the group to which the vehicle had been administered. Compared with the group to which the anti-DNP-IgG1 antibody had been administered, significant differences in tumor size ($p<0.05$) were observed on days 7, 9, 11, and 14 after the engrafting of the cells. Furthermore, compared with the group to which the anti-DNP-IgG1 antibody had been administered, significant tumor suppression ($p<0.05$) was observed on days 14 and 17 after the engrafting of the cells in the case of the group to which the rec263 antibody had been administered at 100 µg/mouse. In contrast, significant tumor suppression ($p<0.05$) was observed on days 7 and 11 after the engrafting of the cells in the case of the group to which the chimeric anti-A33 recombinant antibody had been administered at 10 µg/mouse, compared with the group to which the vehicle had been administered. Compared with the group to which the anti-DNP-IgG1 antibody had been administered, significant tumor suppression ($p<0.05$) was observed on days 7, 9, 11, 14, 17, and 21 after the engrafting of the cells. Moreover, significant tumor suppression ($p<0.05$) was observed on days 7, 9, and 14 after the engrafting of the cells in the case of the group to which the chimeric anti-A33 recombinant antibody had been administered at 100 µg/mouse, compared with the group to which the vehicle had been administered. Compared with the group to which the anti-DNP-IgG1 antibody had been administered, significant tumor suppression ($p<0.05$) was observed on days 7, 9, 11, 14, 17, and 21 after the engrafting of the cells (FIG. 7A).

On the other hand, regarding the mouse line in which the NCI-H508 cell line had been engrafted, no antitumor effects were exerted in the case of the group to which the rec263 antibody had been administered at 10 µg/mouse. In contrast, significant tumor suppression ($p<0.05$) was observed more than 18 days after the engrafting of the cells in the case of the group to which the rec263 antibody had been administered at 100 µg/mouse, compared with the group to which the vehicle had been administered. Moreover, compared with the group to which the anti-DNP-IgG1 antibody had been administered, significant tumor suppression ($p<0.05$) was observed on nearly all measuring days. In contrast, significant tumor suppression ($p<0.05$) was observed on days 21, 55, and 62 after the engrafting of the cells in the case of the group to which the chimeric anti-A33 recombinant antibody had been administered at 10 µg/mouse, compared with the group to which the vehicle had been administered. Furthermore, compared with the group to which the anti-DNP-IgG1 antibody had been administered, significant tumor suppression ($p<0.05$) was observed on days 7, 21, and 33 after the engrafting of the cells. Moreover, significant tumor suppression ($p<0.05$) was observed on nearly all measuring days in the case of the group to which the chimeric anti-A33 recombinant antibody had been administered at 100 µg/mouse, compared with the group to which the vehicle had been administered. Furthermore, compared with the group to which the anti-DNP-IgG1 antibody had been administered, significant tumor suppression ($p<0.05$) was observed by day 33 after the engrafting of the cells.

Figure 7B:
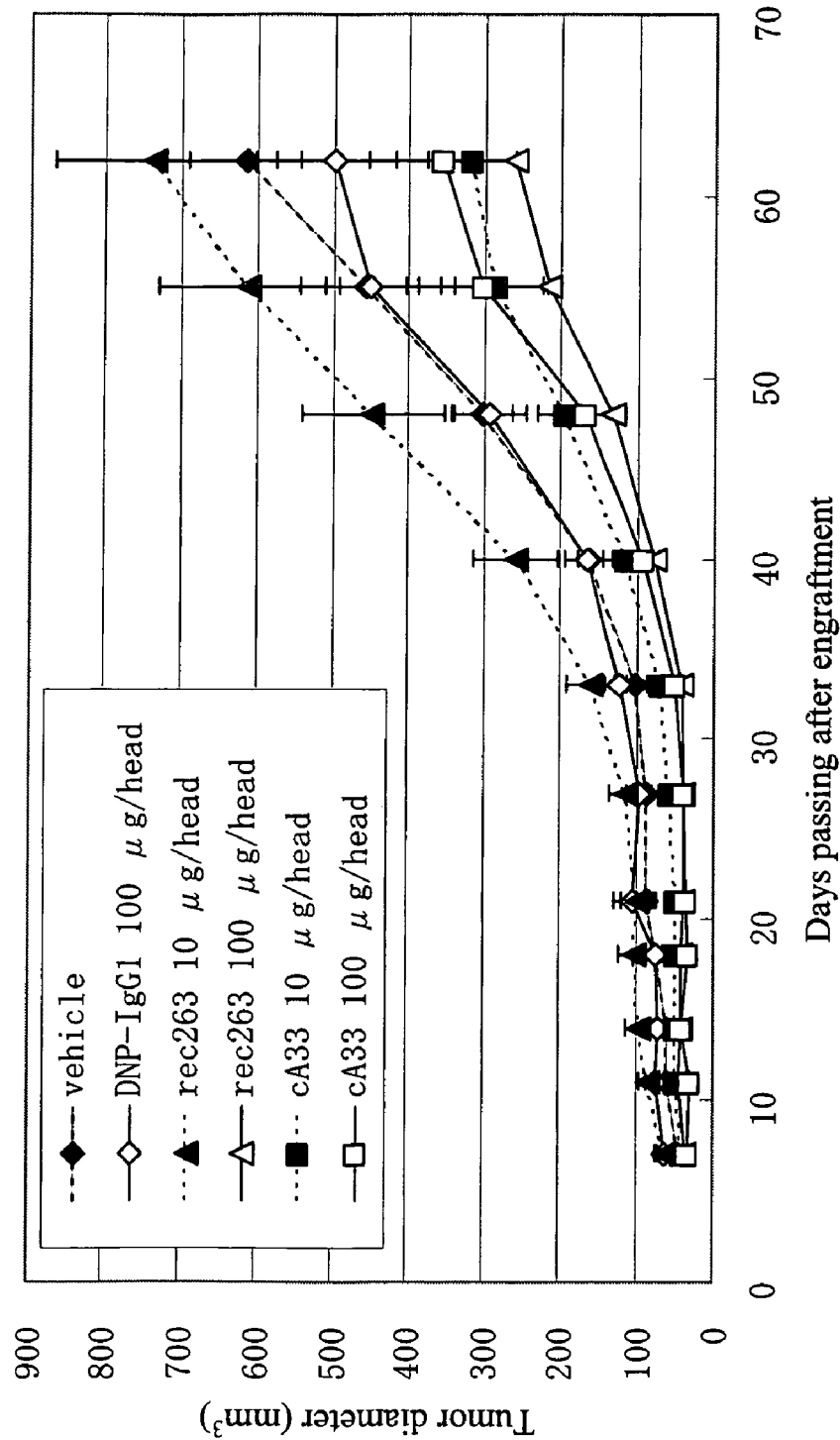
FIG. 7B shows the antitumor effects of recombinant antibodies cA33 and rec263 against a mouse tumor-bearing model wherein NCI-H508 cells were implanted.

As described above, it was demonstrated that the antibodies of the present invention had high antitumor effects on the mouse tumor-bearing models using 2 types of the colorectal cancer cell lines (FIG. 7B).

The effects of the antibodies purified from human anti-A33-producing hybridomas and the human anti-A33 recombinant antibodies were examined using the mouse tumor-bearing models. The cells of colorectal cancer cell lines used herein were COLO205 cells and NCI-H508 cells.

(Antitumor Effects of the Antibodies Purified from 125M10AA, 125M165DAAA and 125M96ABA Hybridomas on the COLO205 Cell Line)

The cells of the colorectal cancer cell line COLO205 were subcutaneously engrafted at $5\times10^6$/mouse in the dorsal regions of 6-week-old Balb/c nude mice (purchased from CLEA Japan). On days 1, 3, 7, 10, 14, and 17 after the engrafting of the cells, the 125M10AA, 125M165DAAA, or 125M96ABA antibody (dissolved in 200 µl of 1% nude mouse serum-containing PBS) was administered intraperitoneally at 20 µg/mouse to tumor-bearing mice (15 mice per group in the case of the group to which the vehicle was administered and 10 mice per group in the other cases). Tumor sizes were measured on days 7, 10, 12, 14, and 17 after the engrafting of the cells. "Vehicle" denotes 1% nude mouse serum-containing PBS (200 µl) that was used as medium for dissolution upon antibody administration.

Figure 7C:
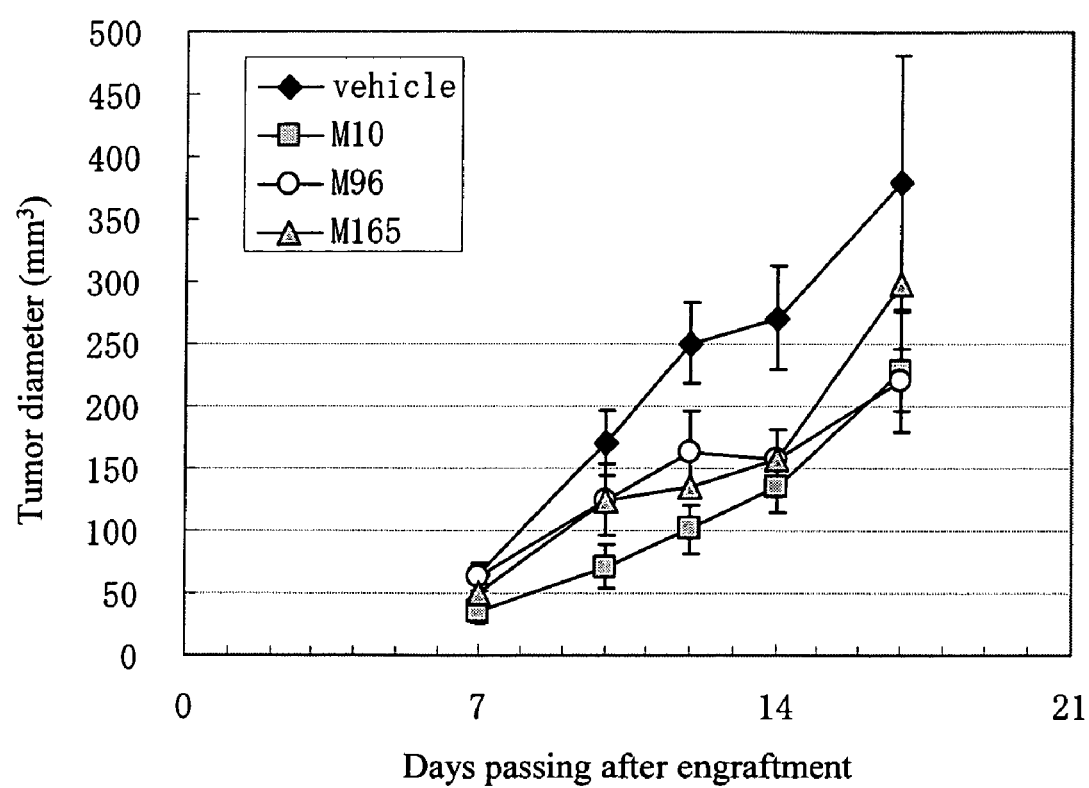
FIG. 7C shows the antitumor effects of purified hybridoma antibodies 125M10AA, 125M165DAAA, and 125M96ABA against a mouse tumor-bearing model wherein COLO205 cells were implanted.

FIG. 7C shows the results of the above experiment. In FIG. 7C, M10 denotes the 125M10AA antibody, M96 denotes the 125M96ABA antibody, and M165 denotes 125M165DAAA antibody. Significant tumor suppression ($p<0.05$) was observed on all measuring days after the engrafting of the cells in the case of the group to which the 125M10AA antibody had been administered, compared with the group to which the vehicle had been administered. Furthermore, significant tumor suppression ($p<0.05$) was observed on days 12, 14, and 17 after the engrafting of the cells in the case of the group to which the 125M165DAAA antibody had been administered, compared with the group to which the vehicle had been administered. In contrast, significant tumor suppression ($p<0.05$) was observed on days 12 and 14 after the engrafting of the cells in the case of the group to which the 125M96ABA antibody had been administered, compared with the group to which the vehicle had been administered.

(Antitumor Effects of N26 and M165 Recombinant Antibodies on COLO205 and NCI-H508 Cell Lines)

The cells of the colorectal cancer cell line COLO205 were subcutaneously engrafted at $5\times10^6$/mouse in the dorsal regions of 6-week-old Balb/c nude mice (purchased from CLEA Japan). On days 1, 3, and 6 after the engrafting of the cells, the recN26 or recM165 antibody (dissolved in 200 µl of 1% nude mouse serum-containing PBS) was administered intraperitoneally at 10 µg/mouse or 100 µg/mouse to tumor-bearing mice (10 mice per group). Tumor sizes were measured on days 8, 10, 13, 15, 17, 20, and 23 after the engrafting of the cells.

Figure 7D:
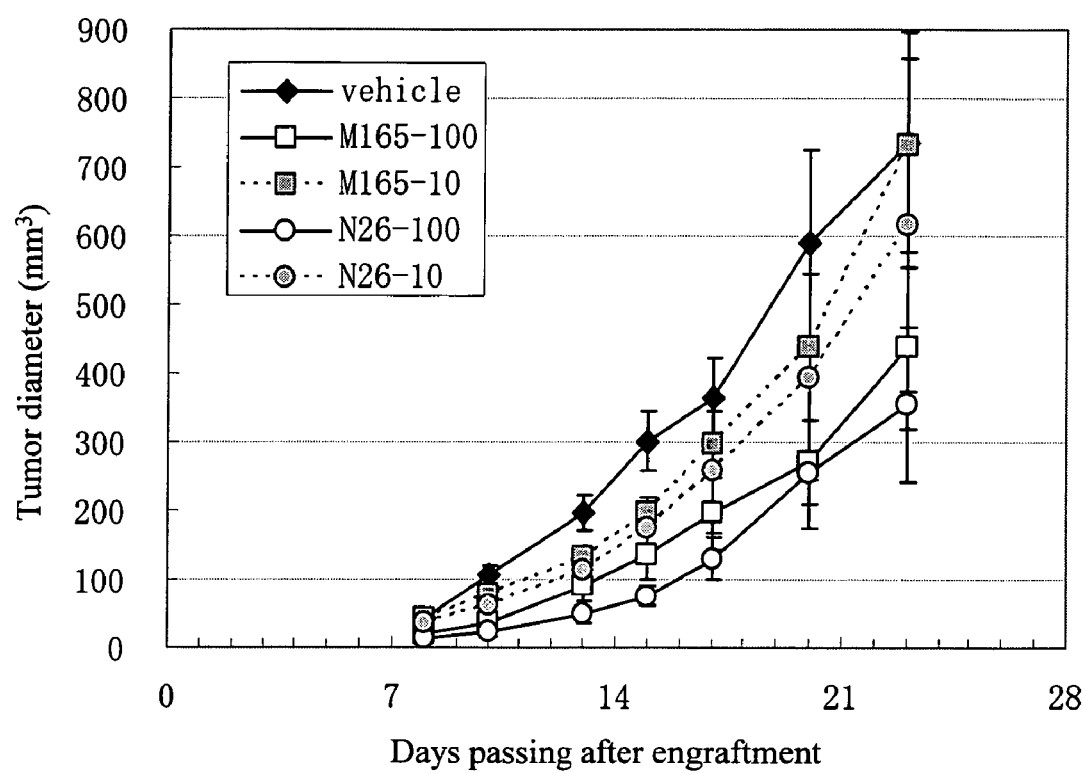
FIG. 7D shows the antitumor effects of recombinant antibodies recN26 and recM165 against a mouse tumor-bearing model wherein NCI-H508 cells were implanted.

FIG. 7D shows the results of the above experiment. In FIG. 7D, M165-10 denotes the recM165 antibody (administered at 10 µg/mouse), M165-100 denotes the recM165 antibody (administered at 100 µg/mouse), N26-10 denotes the recN26 antibody (administered at 10 µg/mouse), and N26-100 denotes the recN26 antibody (100 µg/mouse). Significant tumor suppression ($p<0.05$) was observed on days 10 and 13 after the engrafting of the cells in the case of the group to which the recN26 antibody had been administered at 10 µg/head, compared with the group to which the vehicle had been administered. Furthermore, significant tumor suppression ($p<0.05$) was observed on days 8, 10, 13, 15, 17, and 20 after the engrafting of the cells in the case of the group to which the recN26 antibody had been administered at 100 µg/head, compared with the group to which the vehicle had been administered. Furthermore, significant tumor suppression ($p<0.05$) was observed on days 8, 10, 13, 15, 17, and 20 after the engrafting of the cells in the case of the group to which the recM165 antibody had been administered at 100 µg/head, compared with the group to which the vehicle had been administered.

The cells of the colorectal cancer cell line NCI-H508 and Matrigel (produced by Becton Dickinson Bioscience) comprising mouse malignant sarcoma (that improves the survival and proliferation of engrafted tumor cells) were subcutaneously engrafted at $1\times10^7$/mouse to the dorsal regions of 6-week-old Balb/c nude mice (purchased from CLEA Japan), so that the ratio of NCI-H508 to Matrigel would be 1:1. The recN26 or recM165 antibody (dissolved in 200 µl of 1% nude mouse serum-containing PBS) was administered intraperitoneally at 10 µg/mouse or 100 µg/mouse to tumor-bearing mice (12 mice per group in the case of the group to which the vehicle was administered and 10 mice per group in the other cases) on days 1, 4, and 7 after the engrafting of the cells.

Tumor sizes were measured on days 11, 18, 28, 36, 43, 50, 57, and 64 after the engrafting of the cells.

Figure 7E:
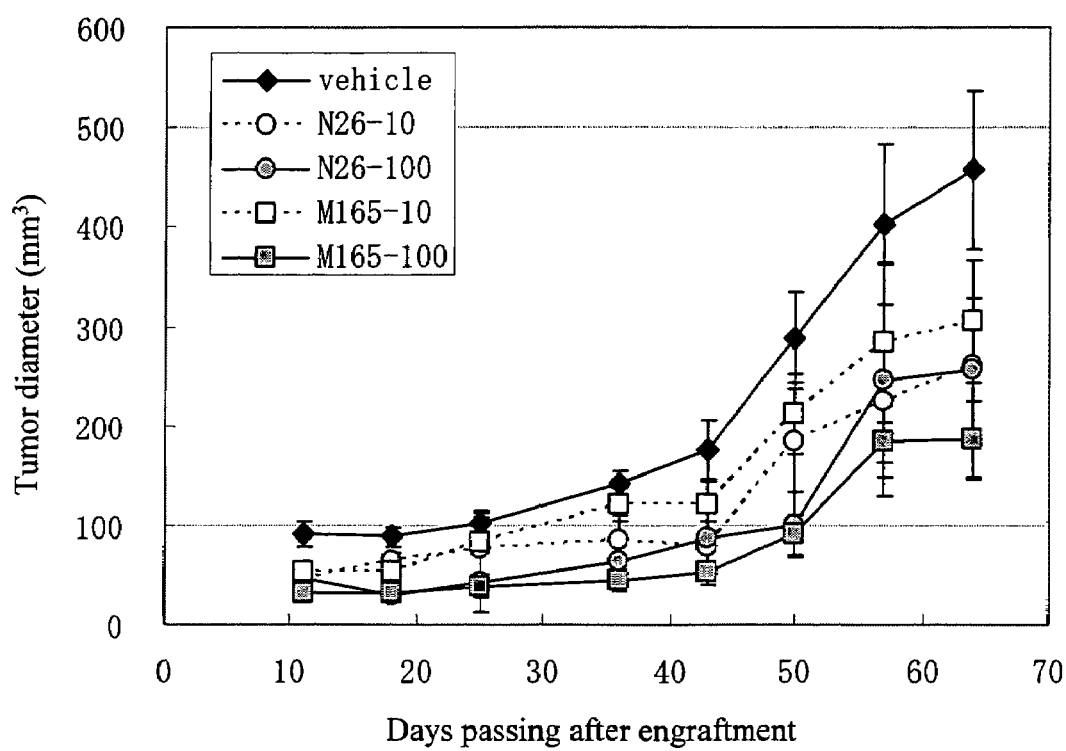
FIG. 7E shows the antitumor effects of recombinant antibodies recN26 and recM165 against a mouse tumor-bearing model wherein NCI-H508 cells were implanted with Matrigel.

FIG. 7E shows the results of the above experiment. In FIG. 7E, N26-10 denotes the recN26 antibody (administered at 10 μg/mouse), N26-100 denotes the recN26 antibody (administered at 100 μg/mouse), M165-10 denotes the recM165 antibody (administered at 10 μg/mouse), and M165-100 denotes the recM165 antibody (administered at 100 μg/mouse). Regarding the mouse line to which the NCI-H508 cell line had been engrafted, significant tumor suppression ($p<0.05$) was observed on days 11, 18, 36, and 43 after the engrafting of the cells in the case of the group to which the recN26 antibody had been administered at 10 μg/mouse, compared with the group to which the vehicle had been administered. Furthermore, compared with the group to which the vehicle had been administered, significant tumor suppression ($p<0.05$) was observed on days 11, 18, 28, 36, and 50 after the engrafting of the cells in the case of the group to which the recN26 antibody had been administered at 100 μg/mouse. In contrast, significant tumor suppression ($p<0.05$) was observed on days 11 and 18 after the engrafting of the cells in the case of the group to which the recM165 antibody had been administered at 10 μg/mouse, compared with the group to which the vehicle had been administered. Compared with the group to which the vehicle had been administered, significant tumor suppression ($p<0.05$) was observed on all measuring days after the engrafting of the cells in the case of the group to which the recM165 antibody had been administered at 100 μg/mouse.

(Antitumor Effects of the M10 and Q54 Recombinant Antibodies on the NCI-H508 Cell Line)

The cells of the colorectal cancer cell line NCI-H508 and Matrigel (produced by Becton Dickinson Bioscience) comprising mouse malignant sarcoma (that improves the survival and proliferation of engrafted tumor cells) were subcutaneously engrafted at $1\times10^7$/mouse to the dorsal regions of 6-week-old Balb/c nude mice (purchased from CLEA Japan), so that the ratio of NCI-H508 to Matrigel would be 1:1. The recM10 or recQ54 antibody (dissolved in 200 μl of 1% nude mouse serum-containing PBS) was administered intraperitoneally at 10 μg/mouse or 100 μg/mouse to tumor-bearing mice (10 mice per group) on days 1, 4, and 7 after the engrafting of the cells. Tumor sizes were measured on days 14, 21, 28, 35, 42, 49, 56, and 63 after the engrafting of the cells.

Figure 7F:
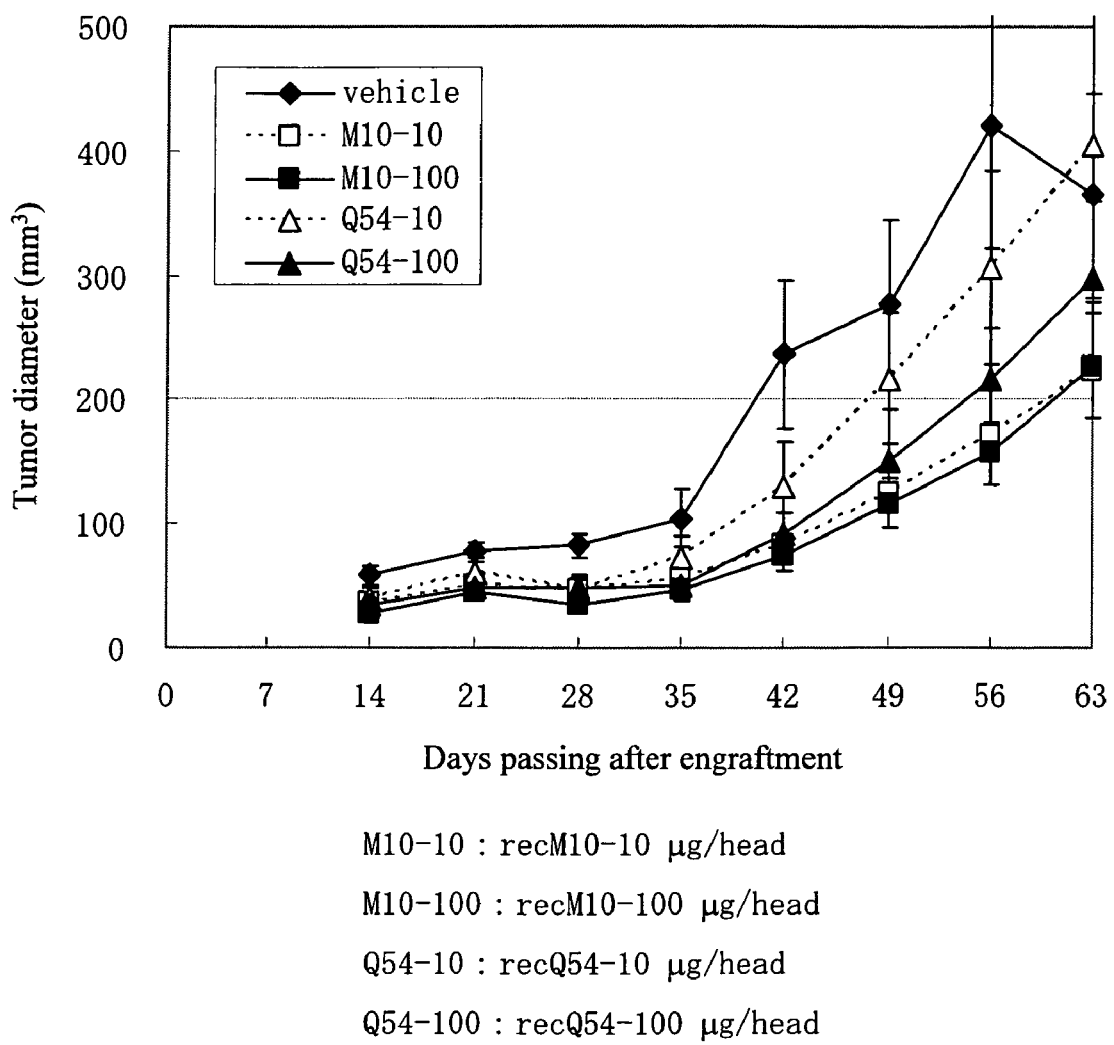
FIG. 7F shows the antitumor effects of recombinant antibodies recM 10 and recQ54 against a mouse tumor-bearing model wherein NCI-H508 cells were implanted with Matrigel.

FIG. 7F shows the results of the above experiment. In FIG. 7F, M10-10 denotes the recM10 antibody (administered at 10 μg/mouse), M10-100 denotes the recM10 antibody (administered at 100 μg/mouse), Q54-10 denotes the recQ54 antibody (administered at 10 μg/mouse), and Q54-100 denotes the recQ54 antibody (administered at 100 μg/mouse). Regarding the mouse line to which the NCI-H508 cell line had been engrafted, significant tumor suppression ($p<0.05$) was observed on days 14, 21, 28, 42, 49, and 56 after the engrafting of the cells in the case of the group to which the recM10 antibody had been administered at 10 μg/mouse, compared with the group to which the vehicle had been administered. Furthermore, compared with the group to which the vehicle had been administered, significant tumor suppression ($p<0.05$) was observed on days 14, 21, 28, 35, 42, 49, and 56 after the engrafting of the cells in the case of the group to which the recM10 antibody had been administered at 100 μg/mouse. In contrast, significant tumor suppression ($p<0.05$) was observed on days 28 and 42 after the engrafting of the cells in the case of the group to which the recQ54 antibody had been administered at 10 μg/mouse, compared with the group to which the vehicle had been administered. Furthermore, compared with the group to which the vehicle had been administered, significant tumor suppression ($p<0.05$) was observed on days 14, 21, 28, 35, 42, and 56 after the engrafting of the cells in the case of the group to which the recQ54 antibody had been administered at 100 μg/mouse.

All publications cited herein are incorporated herein in their entirety. Persons skilled in the art would easily understand that various modifications and changes of the present invention are feasible within the technical idea and the scope of the invention as disclosed in the attached claims. The present invention is intended to include such modifications and changes.

INDUSTRIAL APPLICABILITY

According to the present invention, a preventive or therapeutic agent for diseases due to A33-expressing cells, and in particular, a molecule that is also useful as a malignant tumor remedy for patients with A33 polymorphism, are provided.

9 polymorphisms are currently known for A33 mRNA and 7 such polymorphisms are present in the non-translation region. Furthermore, one of the remaining 2 polymorphisms is present in the $3^{rd}$ codon. Hence, this polymorphism is a silent mutation that does not undergo amino acid substitution. Furthermore, the other one of the remaining two polymorphisms undergoes amino acid substitution, but is present within the signal sequence. Accordingly, the antibody of the present invention is effective for therapeutic or preventive agents, regardless of A33 polymorphism.

All publications, patents, and patent applications cited in this description are herein incorporated by reference in their entirety.

The invention claimed is:

1. A hybridoma identified as N26 and having the International Patent Organism Depository Accession No. FERM BP-10109.

2. An isolated human antibody or a functional fragment thereof, which binds to the A33 polypeptide and recognizes the same epitope as that recognized by the antibody produced by a hybridoma according to claim 1.

3. An isolated human antibody or a functional fragment thereof, which binds to the A33 polypeptide and has the heavy chain variable region and the light chain variable region of the antibody produced by a hybridoma according to claim 1.

4. The human antibody or a functional fragment thereof according to claim 3, wherein the subclass of the antibody heavy chain constant region is IgG1.

5. A pharmaceutical composition, comprising the human antibody or the functional fragment thereof according to any one of claims 2-4 as an active ingredient.

6. A method for treating or preventing cancer in a mammal, comprising administering an effective amount of the pharmaceutical composition of claim 5 to a mammal in need thereof.

7. A method for producing an antibody which binds to the A33 polypeptide, comprising: a) culturing the hybridoma according to claim 1, and b) obtaining the antibody from the culture product.

8. A method for producing an antibody, comprising: a) isolating the polynucleotide encoding the heavy chain variable region and the light chain variable region of an antibody that binds to the A33 polypeptide from the hybridoma according to claim 1, b) constructing an expression vector comprising the polynucleotide, c) introducing the expression vector into a host, d) culturing the host, and e) obtaining the antibody from the culture product.

9. The method according to claim 8, wherein the host is selected from the group consisting of *Escherichia coil*, a yeast cell, an insect cell, a mammalian cell, a plant cell, a plant, and a mammal.

* * * * *

UNITED STATES PATENT AND TRADEMARK OFFICE
CERTIFICATE OF CORRECTION

PATENT NO.        : 7,579,187 B2
APPLICATION NO.   : 11/629779
DATED             : August 25, 2009
INVENTOR(S)       : Shiro Kataoka, Takafumi Tomura and Noriko Otani It is certified that error appears in the above-identified patent and that said Letters Patent is hereby corrected as shown below:

Item (73), Assignee: Please delete "Kyoma" and replace it with Kyowa.

The corrected Item (73) should read: Kyowa Hakko Kirin Co., Ltd., Tokyo

Signed and Sealed this

First Day of December, 2009

David J. Kappos
*Director of the United States Patent and Trademark Office*

SEQUENCE LISTING

<160> NUMBER OF SEQ ID NOS: 89

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence:primer

<400> SEQUENCE: 1
gcccttggtg ctagctgaag agacggtgac cagagtccct tg                42

<210> SEQ ID NO 2
<211> LENGTH: 26
<212> TYPE: DNA

```
<213> ORGANISM: Artificial Sequence
<220> FEATURE:
<223> OTHER INFORMATION: Description of Artificial Sequence:primer

<400> SEQUENCE: 2
gtgcacgccg ctggtcaggg cgcctg                                            26

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 3
gtaaaacgac ggccagtg                                                     18

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 4
caggaaacag ctatgac                                                      17

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence:primer

<400> SEQUENCE: 5
agagagaggt cgacccacca tgaactttgg gctgagctta gtt                         43

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence:primer

<400> SEQUENCE: 6
agagagagag atctctcacc atgggcatca agatggagtt tcag                        44

<210> SEQ ID NO 7
<211> LENGTH: 414
<212> TYPE: DNA
<213> ORGANISM: Homo sapiens

<400> SEQUENCE: 7
atgaactttg ggctgagctt gattttcctt gtcctaattt taaaaggtgt ccagtgtgaa       60
gtgaagctgg tggagtctgg gggaggctta gtgaagcctg gagggtccct gaaactctcc      120
tgtgcagcct ctggattcgc tttcagtacc tatgacatgt cttgggttcg ccagactccg      180
gagaagaggc tggagtgggt cgcaaccatt agtagtggtg gtagttacac ctactattta      240
gacagtgtga agggccgatt caccatctcc agagacagtg ccaggaacac cctataccetg    300 caaatgagca gtctgaggtc tgaggacacg gccttgtatt actgtgcacc gactacggta      360
gtcccgtttg cttactgggg ccaagggact ctggtcaccg tctcttcagc tagc            414
```

<210> SEQ ID NO 8
<211> LENGTH: 138
<212> TYPE: PRT
<213> ORGANISM: Homo sapiens

<400> SEQUENCE: 8

Met Asn Phe Gly Leu Ser Leu Ile Phe Leu Val Leu Ile Leu Lys Gly
 1               5                  10                  15

Val Gln Cys Glu Val Lys Leu Val Glu Ser Gly Gly Gly Leu Val Lys
             20                  25                  30

Pro Gly Gly Ser Leu Lys Leu Ser Cys Ala Ala Ser Gly Phe Ala Phe
         35                  40                  45

Ser Thr Tyr Asp Met Ser Trp Val Arg Gln Thr Pro Glu Lys Arg Leu
     50                  55                  60

Glu Trp Val Ala Thr Ile Ser Ser Gly Gly Ser Tyr Thr Tyr Tyr Leu
 65                  70                  75                  80

Asp Ser Val Lys Gly Arg Phe Thr Ile Ser Arg Asp Ser Ala Arg Asn
                 85                  90                  95

Thr Leu Tyr Leu Gln Met Ser Ser Leu Arg Ser Glu Asp Thr Ala Leu
            100                 105                 110

Tyr Tyr Cys Ala Pro Thr Thr Val Val Pro Phe Ala Tyr Trp Gly Gln
        115                 120                 125

Gly Thr Leu Val Thr Val Ser Ser Ala Ser
    130                 135

<210> SEQ ID NO 9
<211> LENGTH: 396
<212> TYPE: DNA
<213> ORGANISM: Homo sapiens

<400> SEQUENCE: 9
atgggcatca agatggagtt tcagacccag gtctttgtat tcgtgttgct ctggttgtct     60
ggtgttgatg gagacattgt gatgacccag tctcaaaaat tcatgtccac atcagtagga    120
gacagggtca gcatcacctg caaggccagt cagaatgttc gtactgttgt agcctggtat    180
caacagaaac cagggcagtc tcctaaaaca ctgatttact tggcctccaa ccggcacact    240
ggagtccctg atcgcttcac aggcagtgga tctgggacag atttcactct caccattagc    300
aatgtgcaat ctgaagacct ggcagattat ttctgtctgc aacattggag ttatcctctc    360
acgttcggct cggggacaaa gttggaagta aaacgt                              396

<210> SEQ ID NO 10
<211> LENGTH: 132
<212> TYPE: PRT
<213> ORGANISM: Homo sapiens

<400> SEQUENCE: 10

Met Gly Ile Lys Met Glu Phe Gln Thr Gln Val Phe Val Phe Val Leu
 1               5                  10                  15

Leu Trp Leu Ser Gly Val Asp Gly Asp Ile Val Met Thr Gln Ser Gln
             20                  25                  30

Lys Phe Met Ser Thr Ser Val Gly Asp Arg Val Ser Ile Thr Cys Lys
         35                  40                  45

Ala Ser Gln Asn Val Arg Thr Val Val Ala Trp Tyr Gln Gln Lys Pro
     50                  55                  60

Gly Gln Ser Pro Lys Thr Leu Ile Tyr Leu Ala Ser Asn Arg His Thr
 65                  70                  75                  80

Gly Val Pro Asp Arg Phe Thr Gly Ser Gly Ser Gly Thr Asp Phe Thr
                85                  90                  95

Leu Thr Ile Ser Asn Val Gln Ser Glu Asp Leu Ala Asp Tyr Phe Cys
            100                 105                 110

Leu Gln His Trp Ser Tyr Pro Leu Thr Phe Gly Ser Gly Thr Lys Leu
        115                 120                 125

Glu Val Lys Arg
        130

<210> SEQ ID NO 11
<211> LENGTH: 2793
<212> TYPE: DNA
<213> ORGANISM: Homo sapiens

<400> SEQUENCE: 11

| | | | | | |
|---|---|---|---|---|---|
| ctacccctt | gtgagcagtc | taggactttg | tacacctgtt | aagtagggag | aaggcagggg | 60 |
| aggtggctgg | tttaagggga | acttgaggga | agtaggaag | actcctcttg | ggacctttgg | 120 |
| agtaggtgac | acatgagccc | agccccagct | cacctgccaa | tccagctgag | gagctcacct | 180 |
| gccaatccag | ctgaggctgg | gcagaggtgg | gtgagaagag | ggaaaattgc | agggacctcc | 240 |
| agttgggcca | ggccagaagc | tgctgtagct | taaccagac | agctcagacc | tgtctggagg | 300 |
| ctgccagtga | caggttaggt | ttagggcaga | gaagaagcaa | gaccatggtg | gggaagatgt | 360 |
| ggcctgtgtt | gtggacactc | tgtgcagtca | gggtgaccgt | cgatgccatc | tctgtggaaa | 420 |
| ctccgcagga | cgttcttcgg | gcttcgcagg | gaaagagtgt | caccctgccc | tgcacctacc | 480 |
| acacttccac | ctccagtcga | gagggactta | ttcaatggga | taagctcctc | ctcactcata | 540 |
| cggaaagggt | ggtcatctgg | ccgttttcaa | acaaaaacta | catccatggt | gagctttata | 600 |
| agaatcgcgt | cagcatatcc | aacaatgctg | agcagtccga | tgcctccatc | accattgatc | 660 |
| agctgaccat | ggctgacaac | ggcacctacg | agtgttctgt | ctcgctgatg | tcagacctgg | 720 |
| agggcaacac | caagtcacgt | gtccgcctgt | tggtcctcgt | gccaccctcc | aaaccagaat | 780 |
| gcggcatcga | gggagagacc | ataattggga | acaacatcca | gctgacctgc | aatcaaagg | 840 |
| agggctcacc | aacccctcag | tacagctgga | agaggtacaa | catcctgaat | caggagcagc | 900 |
| ccctggccca | gccagcctca | ggtcagcctg | tctccctgaa | gaatatctcc | acagacacat | 960 |
| cgggttacta | catctgtacc | tccagcaatg | aggagggac | gcagttctgc | aacatcacgg | 1020 |
| tggccgtcag | atctccctcc | atgaacgtgg | ccctgtatgt | gggcatcgcg | gtgggcgtgg | 1080 |
| ttgcagccct | cattatcatt | ggcatcatca | tctactgctg | ctgctgccga | gggaaggacg | 1140 |
| acaacactga | agacaaggag | gatgcaaggc | cgaaccggga | agcctatgag | gagccaccag | 1200 |
| agcagctaag | agaactttcc | agagagaggg | aggaggagga | tgactacagg | caagaagagc | 1260 |
| agaggagcac | tgggcgtgaa | tccccggacc | acctcgacca | gtgacaggcc | agcagcagag | 1320 |
| ggcggcggag | gaagggttag | gggttcattc | tcccgcttcc | tggcctccct | tctccttttct | 1380 |
| aagccctgtt | ctcctgtccc | tccatcccag | acattgatgg | ggacatttct | tccccagtgt | 1440 |
| cagctgtggg | gaacatggct | ggcctggtaa | gggggtccct | gtgctgatcc | tgctgacctc | 1500 |
| actgtcctgt | gaagtaaccc | ctcctggctg | tgacacctgg | tgcgggcctg | gccctcactc | 1560 |
| aagaccaggc | tgcagcctcc | acttccctcg | tagttggcag | gagctcctgg | aagcacagcg | 1620 |
| ctgagcatgg | ggcgctccca | ctcagaactc | tccaggagg | cgatgccagc | cttggggggt | 1680 |
| gggggctgtc | ctgctcacct | gtgtgcccag | cacctggagg | ggcaccaggt | ggagggttg | 1740 |
| cactccacac | atctttcttg | aatgaatgaa | agaataagtg | agtatgcttg | ggccctgcat | 1800 |

```
tggcctggcc tccagctccc actcccttc caacctcact tcccgtagct gccagtatgt    1860
tccaaaccct cctgggaagg ccacctccca ctcctgctgc acaggccctg gggagctttt    1920
gcccacacac tttccatctc tgcctgtcaa tatcgtacct gtccctccag gcccatctca    1980
aatcacaagg atttctctaa ccctatccta attgtccaca tacgtggaaa caatcctgtt    2040
actctgtccc acgtccaatc atgggccaca aggcacagtc ttctgagcga gtgctctcac    2100
tgtattagag cgccagctcc ttggggcagg gcctgggcct catggctttt gctttccctg    2160
aagccctagt agctggcgcc catcctagtg ggcacttaag cttaattggg gaaactgctt    2220
tgattggttg tgccttccct tctctggtct ccttgagatg atcgtagaca cagggatgat    2280
tcccacccaa acccacgtat tcattcagtg agttaaacac gaattgattt aaagtgaaca    2340
cacacaaggg agcttgcttg cagatggtct gagttcttgt gtcctggtaa ttcctctcca    2400
ggccagaata attggcatgt ctcctcaacc cacatggggt tcctggttgt tcctgcatcc    2460
cgatacctca gccctggccc tgcccagccc atttgggctc tggttttctg gtggggctgt    2520
cctgctgccc tcccacagcc tccttctgtt tgtcgagcat ttcttctact cttgagagct    2580
caggcagcgt tagggctgct taggtctcat ggaccagtgg ctggtctcac ccaactgcag    2640
tttactattg ctatcttttc tggatgatca gaaaaataat tccataaatc tattgtctac    2700
ttgcgatttt ttaaaaaatg tatatttta tatatattgt taaatccttt gcttcattcc    2760
aaatgctttc agtaataata aaattgtggg tgg                                 2793

<210> SEQ ID NO 12
<211> LENGTH: 319
<212> TYPE: PRT
<213> ORGANISM: Homo sapiens

<400> SEQUENCE: 12

Met Val Gly Lys Met Trp Pro Val Leu Trp Thr Leu Cys Ala Val Arg
 1               5                  10                  15

Val Thr Val Asp Ala Ile Ser Val Glu Thr Pro Gln Asp Val Leu Arg
                20                  25                  30

Ala Ser Gln Gly Lys Ser Val Thr Leu Pro Cys Thr Tyr His Thr Ser
            35                  40                  45

Thr Ser Ser Arg Glu Gly Leu Ile Gln Trp Asp Lys Leu Leu Leu Thr
        50                  55                  60

His Thr Glu Arg Val Val Ile Trp Pro Phe Ser Asn Lys Asn Tyr Ile
65                  70                  75                  80

His Gly Glu Leu Tyr Lys Asn Arg Val Ser Ile Ser Asn Asn Ala Glu
                85                  90                  95

Gln Ser Asp Ala Ser Ile Thr Ile Asp Gln Leu Thr Met Ala Asp Asn
            100                 105                 110

Gly Thr Tyr Glu Cys Ser Val Ser Leu Met Ser Asp Leu Glu Gly Asn
        115                 120                 125

Thr Lys Ser Arg Val Arg Leu Leu Val Leu Val Pro Pro Ser Lys Pro
    130                 135                 140

Glu Cys Gly Ile Glu Gly Glu Thr Ile Ile Gly Asn Asn Ile Gln Leu
145                 150                 155                 160

Thr Cys Gln Ser Lys Glu Gly Ser Pro Thr Pro Gln Tyr Ser Trp Lys
                165                 170                 175

Arg Tyr Asn Ile Leu Asn Gln Glu Gln Pro Leu Ala Gln Pro Ala Ser
            180                 185                 190
```

```
Gly Gln Pro Val Ser Leu Lys Asn Ile Ser Thr Asp Thr Ser Gly Tyr
            195                 200                 205

Tyr Ile Cys Thr Ser Ser Asn Glu Glu Gly Thr Gln Phe Cys Asn Ile
        210                 215                 220

Thr Val Ala Val Arg Ser Pro Ser Met Asn Val Ala Leu Tyr Val Gly
225                 230                 235                 240

Ile Ala Val Gly Val Val Ala Ala Leu Ile Ile Gly Ile Ile Ile
                245                 250                 255

Tyr Cys Cys Cys Cys Arg Gly Lys Asp Asp Asn Thr Glu Asp Lys Glu
                260                 265                 270

Asp Ala Arg Pro Asn Arg Glu Ala Tyr Glu Glu Pro Pro Glu Gln Leu
            275                 280                 285

Arg Glu Leu Ser Arg Glu Arg Glu Glu Asp Asp Tyr Arg Gln Glu
        290                 295                 300

Glu Gln Arg Ser Thr Gly Arg Glu Ser Pro Asp His Leu Asp Gln
305                 310                 315

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 13
gcagacgaat tcaagaccat ggtggggaag at                              32

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence:primer

<400> SEQUENCE: 14
ctcgagcggc cgctctgctg ctggcctgtc actggtcgag gtg                  43

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 15
ctcgagcggc cgccagttca tggagggaga tctgacg                         37

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 16
tcttgtccac cttggtgttg ctgggcttgt g                               31

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence:primer
```

<400> SEQUENCE: 17
gttgaagctc tttgtgacgg gcgagc                                          26

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 18
tgcacgccgc tggtcagggc gcctgagttc c                                    31

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 19
aggcacacaa cagaggcagt tccagatttc                                      30

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 20
gctggagggc acggtcacca cgctg                                           25

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 21
ggtgccaggg ggaagaccga tgg                                             23

<210> SEQ ID NO 22
<211> LENGTH: 435
<212> TYPE: DNA
<213> ORGANISM: Homo sapiens

<400> SEQUENCE: 22
atggagtttg gctgagctg gcttttctt gtggctattt taaaaggtgt ccagtgtgag       60
gtgcagttgt tggagtctgg gggaggcttg gtacagcctg ggggtccct gagactctcc      120 tgtgcagcct ctggattcac ctttagcagc tatgccatga gctggatccg ccaggctcca     180 gggaagggc tggagtgggt ctcagctatt agtgctagtg gtggtagcac atactacgca      240
gactccgtga agggccggtt caccatctcc agagacaatt ccaagaacac gctgtatctg     300
caaatgaaca gcctgagagc cgaggacacg gccgtatatt actgtgcgaa agatcggata     360
gtgggagcta cgaactacta ctacggtatg gacgtctggg gccaagggac cacggtcacc     420
gtctcctcag ctagc                                                      435

<210> SEQ ID NO 23

<211> LENGTH: 145
<212> TYPE: PRT
<213> ORGANISM: Homo sapiens

<400> SEQUENCE: 23

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Ile Arg Gln Ala Pro Gly Lys Gly Leu
    50                  55                  60

Glu Trp Val Ser Ala Ile Ser Ala Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Thr Ala Val
            100                 105                 110

Tyr Tyr Cys Ala Lys Asp Arg Ile Val Gly Ala Thr Asn Tyr Tyr Tyr
        115                 120                 125

Gly Met Asp Val Trp Gly Gln Gly Thr Thr Val Thr Val Ser Ser Ala
    130                 135                 140

Ser
145

<210> SEQ ID NO 24
<211> LENGTH: 390
<212> TYPE: DNA
<213> ORGANISM: Homo sapiens

<400> SEQUENCE: 24
atggacatga gggtccccgc tcagctcctg gggctcctgc tgctctggtt cccaggttcc     60
agatgcgaca tccagatgac ccagtctcca ccttccgtgt ctgcatctgt aggagacaga    120
gtcaccatca cttgtcgggc gagtcagggt attagcagct ggttagcctg gtatcagcat    180
aaaccaggga aagcccccaa gctcctgatc tatggtgcat ccagtttgca aagtggggtc    240
ccatcaaggt tcagcggcag tggatctggg acagatttca ctctcaccat cagcagcctg    300
cagcctgaag attttgcaac ttactattgt caacaggcta atagtttccc tatcaccttc    360
ggccaaggga cacgactgga gattaaacgt                                     390

<210> SEQ ID NO 25
<211> LENGTH: 130
<212> TYPE: PRT
<213> ORGANISM: Homo sapiens

<400> SEQUENCE: 25

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Pro Ser
            20                  25                  30

Val Ser Ala Ser Val Gly Asp Arg Val Thr Ile Thr Cys Arg Ala Ser
        35                  40                  45

Gln Gly Ile Ser Ser Trp Leu Ala Trp Tyr Gln His Lys Pro Gly Lys
    50                  55                  60

Ala Pro Lys Leu Leu Ile Tyr Gly Ala Ser Ser Leu Gln Ser Gly Val

```
                65                  70                  75                  80
Pro Ser Arg Phe Ser Gly Ser Gly Ser Gly Thr Asp Phe Thr Leu Thr
                    85                  90                  95

Ile Ser Ser Leu Gln Pro Glu Asp Phe Ala Thr Tyr Tyr Cys Gln Gln
                100                 105                 110

Ala Asn Ser Phe Pro Ile Thr Phe Gly Gln Gly Thr Arg Leu Glu Ile
                115                 120                 125

Lys Arg
    130

<210> SEQ ID NO 26
<211> LENGTH: 447
<212> TYPE: DNA
<213> ORGANISM: Homo sapiens

<400> SEQUENCE: 26
atggatctca tgtgcaagaa aatgaagcac ctgtggttct tcctcctgct ggtggcggct       60
cccagatggg tcctgtccca gctgcaggtg caggagtcgg gcccaggact ggtgaagcct      120
tcggagaccc tgtccctcat ctgcactgtc tctggtggct ccatcaggac cagtggttac      180
tactggggct ggttccgcca gcccccaggg aagggactgg agtggattgg actagtcat       240 aatagtggga gcacctacta caacccgtcc ctcaagagtc gagtcaccat atccgtagac      300
acgtccaaga accagttctc cctgaagctg aactctgtga ccgccgcaga cacggctgtg      360
tattactgtg cgagacaagg ttacgatttt aaagtcaata tagacgtctg gggacaaggg      420
accacggtca ccgtctcctc agctagc                                          447

<210> SEQ ID NO 27
<211> LENGTH: 149
<212> TYPE: PRT
<213> ORGANISM: Homo sapiens

<400> SEQUENCE: 27

Met Asp Leu Met Cys Lys Lys Met Lys His Leu Trp Phe Phe Leu Leu
  1               5                  10                  15

Leu Val Ala Ala Pro Arg Trp Val Leu Ser Gln Leu Gln Val Gln Glu
                 20                  25                  30

Ser Gly Pro Gly Leu Val Lys Pro Ser Glu Thr Leu Ser Leu Ile Cys
             35                  40                  45

Thr Val Ser Gly Gly Ser Ile Arg Thr Ser Gly Tyr Tyr Trp Gly Trp
         50                  55                  60

Phe Arg Gln Pro Pro Gly Lys Gly Leu Glu Trp Ile Gly Thr Ser His
 65                  70                  75                  80

Asn Ser Gly Ser Thr Tyr Tyr Asn Pro Ser Leu Lys Ser Arg Val Thr
                 85                  90                  95

Ile Ser Val Asp Thr Ser Lys Asn Gln Phe Ser Leu Lys Leu Asn Ser
                100                 105                 110

Val Thr Ala Ala Asp Thr Ala Val Tyr Tyr Cys Ala Arg Gln Gly Tyr
                115                 120                 125

Asp Phe Lys Val Asn Ile Asp Val Trp Gly Gln Gly Thr Thr Val Thr
            130                 135                 140

Val Ser Ser Ala Ser
145

<210> SEQ ID NO 28
<211> LENGTH: 384
```

<212> TYPE: DNA
<213> ORGANISM: Homo sapiens

<400> SEQUENCE: 28

```
atggaagccc cagctcagct tctcttcctc ctgctactct ggctcccaga taccaccgga      60
gaaattgtgt tgacacagtc tccagccacc ctgtctttgt ctccagggga aagagccacc     120
ctctcctgca gggccagtca gagtgttagc agctacttag cctggtacca acagaaacct     180
ggccaggctc ccaggctcct catctatgat gcatccaaca gggccactgg catcccagcc     240
aggttcagtg gcagtgggtc tgggacagac ttcactctca ccatcagcag cctagagcct     300
gaagattttg cagtttatta ctgtcagcag cgtagcaact ggccgctcac tttcggcgga     360
gggaccaagg tggagatcaa acga                                             384
```

<210> SEQ ID NO 29
<211> LENGTH: 128
<212> TYPE: PRT
<213> ORGANISM: Homo sapiens

<400> SEQUENCE: 29

```
Met Glu Ala Pro Ala Gln Leu Leu Phe Leu Leu Leu Trp Leu Pro
  1               5                  10                  15
Asp Thr Thr Gly Glu Ile Val Leu Thr Gln Ser Pro Ala Thr Leu Ser
                 20                  25                  30
Leu Ser Pro Gly Glu Arg Ala Thr Leu Ser Cys Arg Ala Ser Gln Ser
             35                  40                  45
Val Ser Ser Tyr Leu Ala Trp Tyr Gln Gln Lys Pro Gly Gln Ala Pro
         50                  55                  60
Arg Leu Leu Ile Tyr Asp Ala Ser Asn Arg Ala Thr Gly Ile Pro Ala
 65                  70                  75                  80
Arg Phe Ser Gly Ser Gly Ser Gly Thr Asp Phe Thr Leu Thr Ile Ser
                     85                  90                  95
Ser Leu Glu Pro Glu Asp Phe Ala Val Tyr Tyr Cys Gln Gln Arg Ser
                100                 105                 110
Asn Trp Pro Leu Thr Phe Gly Gly Gly Thr Lys Val Glu Ile Lys Arg
            115                 120                 125
```

<210> SEQ ID NO 30
<211> LENGTH: 426
<212> TYPE: DNA
<213> ORGANISM: Homo sapiens

<400> SEQUENCE: 30

```
atggagtttg ggctgagctg ggttttcctc gttgctcttt taagaggtgt ccagtgtcag      60
gtgcagctgg tggagtctgg gggaggcgtg gtccagcctg gaggtccct gagactctcc      120
tgtgcagcgt ctggattcac cttcagttat tatggcatgc actgggtccg ccaggctcca     180
ggcaaggggc tggagtgggt ggcagttata tggtatgatg gaagtaataa atactatgca     240
gactccgtga agggccgatt caccatctcc agagacaatt ccaagaaaac gctgtatctg     300
caaatgaaca gcctgagagc cgaggacacg gctgtgtatt actgtgcgag agatgggcat     360
agcagtggct gggggactt ccagcactgg ggccagggca cctggtcac cgtctcctca      420
gctagc                                                                 426
```

<210> SEQ ID NO 31
<211> LENGTH: 142
<212> TYPE: PRT

-continued

<213> ORGANISM: Homo sapiens

<400> SEQUENCE: 31

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Tyr Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Lys
                85                  90                  95

Thr Leu Tyr Leu Gln Met Asn Ser Leu Arg Ala Glu Asp Thr Ala Val
            100                 105                 110

Tyr Tyr Cys Ala Arg Asp Gly His Ser Ser Gly Trp Gly Asp Phe Gln
        115                 120                 125

His Trp Gly Gln Gly Thr Leu Val Thr Val Ser Ser Ala Ser
    130                 135                 140

<210> SEQ ID NO 32
<211> LENGTH: 384
<212> TYPE: DNA
<213> ORGANISM: Homo sapiens

<400> SEQUENCE: 32
atggaagccc cagctcagct tctcttcctc ctgctactct ggctcccaga taccaccgga      60
gaaattgtgt tgacacagtc tccagccacc ctgtctttgt ctccagggga aagagccacc     120
ctctcctgca gggccagtca gagtgttagc agctccttag cctggtacca acagaaacct     180
ggccaggctc ccaggctcct catctatgat gcatccaaca gggccactgg catcccagcc     240
aggttcagtg gcagtgggtc tgggacagac ttcactctca ccatcagcag cctagagcct     300
gaagattttg caatttatta ctgtcagcag cgtagcaact ggcctccgac gttcggccaa     360
gggaccaagg tggaaatcaa acga                                            384

<210> SEQ ID NO 33
<211> LENGTH: 128
<212> TYPE: PRT
<213> ORGANISM: Homo sapiens

<400> SEQUENCE: 33

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Ser Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

-continued

```
Ser Leu Glu Pro Glu Asp Phe Ala Ile Tyr Tyr Cys Gln Gln Arg Ser
            100                 105                 110

Asn Trp Pro Pro Thr Phe Gly Gln Gly Thr Lys Val Glu Ile Lys Arg
        115                 120                 125

<210> SEQ ID NO 34
<211> LENGTH: 426
<212> TYPE: DNA
<213> ORGANISM: Homo sapiens

<400> SEQUENCE: 34
atgaagcacc tgtggttctt cctcctgctg gtggcggctc ccagatgggt cctgtcccaa      60
ctgcagctgc aggagtcggg cccaggactg gtgaagcctt cggagaccct gtccctcacc     120
tgcactgtct ctggtggctc catcagcact agtagttact actggggctg gatccgccag     180
ccccccggga agggcctgga atggattggg actatctatt ataatgggag cacctactac     240
agcccgtccc tcaagagtcg agtcagtata tccgtagaca cgtccaagaa ccagttctcc     300
ctgaagctga gctctgtgac cgccgcagac acgtctgtgt attactgtgc gagacaaggt     360
tacgatatta aaatcaatat agacgtctgg ggccaaggga ccacggtcac cgtctcctca     420
gctagc                                                               426

<210> SEQ ID NO 35
<211> LENGTH: 142
<212> TYPE: PRT
<213> ORGANISM: Homo sapiens

<400> SEQUENCE: 35

Met Lys His Leu Trp Phe Phe Leu Leu Leu Val Ala Ala Pro Arg Trp
  1               5                  10                  15

Val Leu Ser Gln Leu Gln Leu Gln Glu Ser Gly Pro Gly Leu Val Lys
             20                  25                  30

Pro Ser Glu Thr Leu Ser Leu Thr Cys Thr Val Ser Gly Gly Ser Ile
         35                  40                  45

Ser Thr Ser Ser Tyr Tyr Trp Gly Trp Ile Arg Gln Pro Pro Gly Lys
     50                  55                  60

Gly Leu Glu Trp Ile Gly Thr Ile Tyr Tyr Asn Gly Ser Thr Tyr Tyr
 65                  70                  75                  80

Ser Pro Ser Leu Lys Ser Arg Val Ser Ile Ser Val Asp Thr Ser Lys
                 85                  90                  95

Asn Gln Phe Ser Leu Lys Leu Ser Ser Val Thr Ala Ala Asp Thr Ser
            100                 105                 110

Val Tyr Tyr Cys Ala Arg Gln Gly Tyr Asp Ile Lys Ile Asn Ile Asp
        115                 120                 125

Val Trp Gly Gln Gly Thr Thr Val Thr Val Ser Ser Ala Ser
    130                 135                 140

<210> SEQ ID NO 36
<211> LENGTH: 384
<212> TYPE: DNA
<213> ORGANISM: Homo sapiens

<400> SEQUENCE: 36
atggaagccc agctcagct tctcttcctc ctgctactct ggctcccaga taccaccgga      60
gaaattgtgt tgacacagtc tccagccacc ctgtctttgt ctccagggga aagagccacc     120
ctctcctgca gggccagtca gagtgttagc agctacttag cctggtacca acagaaacct    180
```

```
ggccaggctc ccaggctcct catctatgtt gcatccaaca gggccactgg catcccagcc      240
aggttcagtg gcagtgggtc tgggacagac ttcactctca ccatcagcag cctagagcct      300
gaagattttg cagtttatta ctgtcagcag cgtagcaact ggccgctcac tttcggcgga      360
gggaccaagg tggagatcaa acga                                             384
```

<210> SEQ ID NO 37
<211> LENGTH: 128
<212> TYPE: PRT
<213> ORGANISM: Homo sapiens

<400> SEQUENCE: 37

```
Met Glu Ala Pro Ala Gln Leu Leu Phe Leu Leu Leu Leu Trp Leu Pro
  1               5                  10                  15

Asp Thr Thr Gly Glu Ile Val Leu Thr Gln Ser Pro Ala Thr Leu Ser
                 20                  25                  30

Leu Ser Pro Gly Glu Arg Ala Thr Leu Ser Cys Arg Ala Ser Gln Ser
             35                  40                  45

Val Ser Ser Tyr Leu Ala Trp Tyr Gln Gln Lys Pro Gly Gln Ala Pro
     50                  55                  60

Arg Leu Leu Ile Tyr Val Ala Ser Asn Arg Ala Thr Gly Ile Pro Ala
 65                  70                  75                  80

Arg Phe Ser Gly Ser Gly Ser Gly Thr Asp Phe Thr Leu Thr Ile Ser
                 85                  90                  95

Ser Leu Glu Pro Glu Asp Phe Ala Val Tyr Tyr Cys Gln Gln Arg Ser
            100                 105                 110

Asn Trp Pro Leu Thr Phe Gly Gly Gly Thr Lys Val Glu Ile Lys Arg
        115                 120                 125
```

<210> SEQ ID NO 38
<211> LENGTH: 426
<212> TYPE: DNA
<213> ORGANISM: Homo sapiens

<400> SEQUENCE: 38

```
atggagtttg ggctgagctg ggttttcctc gttgctcttt taagaggtgt ccagtgtcag       60
gtgcagttgg tggagtctgg gggaggcgtg gtccagcctg gaggtccct gagactctcc       120 tgtgcagcgt ctggattcac cttcagtcac tatggcatgc actgggtccg ccaggctcca      180
ggcaaggggc tggagtgggt ggcacttata tggtatgatg aagtaataa atactatgca       240 gactccgtga agggccgatt caccatctcc agagacaatt ccaagaacac gctgtatctg      300
caaatgaaca gcctgagagc cgaggacacg gctgtgtatt actgtgcgag gatcccctta      360
gcagctggta cgtcctactt tgactactgg ggccaggga ccctggtcac cgtctcctca       420
gctagc                                                                 426
```

<210> SEQ ID NO 39
<211> LENGTH: 142
<212> TYPE: PRT
<213> ORGANISM: Homo sapiens

<400> SEQUENCE: 39

```
Met Glu Phe Gly Leu Ser Trp Val Phe Leu Val Ala Leu Leu Arg Gly
  1               5                  10                  15

Val Gln Cys Gln Val Gln Leu Val Glu Ser Gly Gly Gly Val Val Gln
                 20                  25                  30

Pro Gly Arg Ser Leu Arg Leu Ser Cys Ala Ala Ser Gly Phe Thr Phe
```

```
                35                  40                  45
Ser His Tyr Gly Met His Trp Val Arg Gln Ala Pro Gly Lys Gly Leu
        50                  55                  60

Glu Trp Val Ala Leu Ile Trp Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
           100                 105                 110

Tyr Tyr Cys Ala Arg Asp Pro Leu Ala Ala Gly Thr Ser Tyr Phe Asp
           115                 120                 125

Tyr Trp Gly Gln Gly Thr Leu Val Thr Val Ser Ser Ala Ser
           130                 135                 140
```

<210> SEQ ID NO 40
<211> LENGTH: 378
<212> TYPE: DNA
<213> ORGANISM: Homo sapiens

<400> SEQUENCE: 40

```
atgtcgccat acaactcat tgggtttctg ctgctctggg ttccagcctc caggggtgaa    60
attgtgctga ctcagtctcc agactttcag tctgtgactc caaaggagaa agtcaccatc   120
acctgccggg ccagtcagag cattggtagt agcttacact ggtaccagca gaaaccagat   180
cagtctccaa agctcctcat caagtatgct tcccagtcct tctcaggggt cccctcgagg   240
ttcagtggca gtggatctgg gacagatttc accctcacca tcaatagcct ggaagctgaa   300
gatgctgcag cgtattactg tcatcagagt agtagtttac cattcacttt cggccctggg   360
accaaagtgg atatcaaa                                                 378
```

<210> SEQ ID NO 41
<211> LENGTH: 126
<212> TYPE: PRT
<213> ORGANISM: Homo sapiens

<400> SEQUENCE: 41

```
Met Ser Pro Ser Gln Leu Ile Gly Phe Leu Leu Leu Trp Val Pro Ala
 1               5                  10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
 65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
           100                 105                 110

Leu Pro Phe Thr Phe Gly Pro Gly Thr Lys Val Asp Ile Lys
           115                 120                 125
```

<210> SEQ ID NO 42
<211> LENGTH: 426
<212> TYPE: DNA
<213> ORGANISM: Homo sapiens

<400> SEQUENCE: 42

```
atggagtttg ggctgagctg gcttttcctt gtggctattt taaaaggtgt ccagtgtgag    60
gtgcagctgt tggagtctgg gggaggcttg gtacagcctg gggggtccct gagactctcc   120
tgtgcagcct ctggattcac cttcagcagc tacgccatga cctgggtccg ccaggctcca   180
gggaaggggc tggagtgggt ctcagatatt agtggtagtg gtggttatac atactacgca   240
gactccgtga agggccggtt caccatctcc agagacaatt ccaagaacac gctgtatctg   300
caaatgaaca gcctgagagc cgaggacacg gccgtatatt actgtgcgaa aacaggcgct   360
ggttcgggga gttattcccc tgactcctgg ggccagggaa ccctggtcac cgtctcctca   420
gctagc                                                              426
```

<210> SEQ ID NO 43
<211> LENGTH: 142
<212> TYPE: PRT
<213> ORGANISM: Homo sapiens

<400> SEQUENCE: 43

```
Met Glu Phe Gly Leu Ser Trp Leu Phe Leu Val Ala Ile Leu Lys Gly
  1               5                  10                  15
Val Gln Cys Glu Val Gln Leu Leu Glu Ser Gly Gly Gly Leu Val Gln
                 20                  25                  30
Pro Gly Gly Ser Leu Arg Leu Ser Cys Ala Ala Ser Gly Phe Thr Phe
             35                  40                  45
Ser Ser Tyr Ala Met Thr Trp Val Arg Gln Ala Pro Gly Lys Gly Leu
         50                  55                  60
Glu Trp Val Ser Asp Ile Ser Gly Ser Gly Gly Tyr Thr Tyr Tyr Ala
 65                  70                  75                  80
Asp Ser Val Lys Gly Arg Phe Thr Ile Ser Arg Asp Asn Ser Lys Asn
                 85                  90                  95
Thr Leu Tyr Leu Gln Met Asn Ser Leu Arg Ala Glu Asp Thr Ala Val
            100                 105                 110
Tyr Tyr Cys Ala Lys Thr Gly Ala Gly Ser Gly Ser Tyr Ser Pro Asp
        115                 120                 125
Ser Trp Gly Gln Gly Thr Leu Val Thr Val Ser Ser Ala Ser
    130                 135                 140
```

<210> SEQ ID NO 44
<211> LENGTH: 390
<212> TYPE: DNA
<213> ORGANISM: Homo sapiens

<400> SEQUENCE: 44

```
atggacatga gggtcctcgc tcagctcctg gggctcctgc tgctctgttt cccaggtgcc   60
agatgtgaca tccagatgac ccagtctcca cctcactgt ctgcatctgt aggagacaga   120
gtcaccatca cttgtcgggc gagtcagggt attagcagct ggttagcctg gtatcagcag   180
aaaccagaga agcccctaa gtccctgatc tatgctgcat ccagtttgca aagtggggtc   240
ccatcaaggt tcagcggcag tggatctggg acagatttca ctctcaccat cagcagcctg   300
cagcctgaag attttgcaac ttattactgc caacagtata atagttaccc gtacactttt   360
ggccagggga ccaagctgga gatcaaacga                                    390
```

<210> SEQ ID NO 45
<211> LENGTH: 130

<212> TYPE: PRT
<213> ORGANISM: Homo sapiens

<400> SEQUENCE: 45

```
Met Asp Met Arg Val Leu Ala Gln Leu Leu Gly Leu Leu Leu Leu Cys
  1               5                  10                  15

Phe Pro Gly Ala Arg Cys Asp Ile Gln Met Thr Gln Ser Pro Ser Ser
                 20                  25                  30

Leu Ser Ala Ser Val Gly Asp Arg Val Thr Ile Thr Cys Arg Ala Ser
             35                  40                  45

Gln Gly Ile Ser Ser Trp Leu Ala Trp Tyr Gln Gln Lys Pro Glu Lys
         50                  55                  60

Ala Pro Lys Ser Leu Ile Tyr Ala Ala Ser Ser Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
            100                 105                 110

Tyr Asn Ser Tyr Pro Tyr Thr Phe Gly Gln Gly Thr Lys Leu Glu Ile
        115                 120                 125

Lys Arg
    130
```

<210> SEQ ID NO 46
<211> LENGTH: 426
<212> TYPE: DNA
<213> ORGANISM: Homo sapiens

<400> SEQUENCE: 46

```
atggagtttg ggctgagctg gcttttctt gtggctattt taaaaggtgt ccagtgtgag      60
gtgcagctgt tggagtctgg gggaggcttg gtacagcctg gggggtccct gagactctcc     120
tgtgcagcct ctggattcac ctttagcagc tatgccatga gctgggtccg ccaggctcca     180
gggaaggggc tggagtgggt ctcagatatt agtggtagtg gtggttacac atactacgca     240
gactccgtga agggccggtt caccatctcc agagacaatt ccaagaacac gctgtatctg     300
caaatgaaca gcctgagagc cgaggacacg gccgtatatt actgtgcgaa aacaggcgat     360
ggttcgggga gttattcccc tgactcctgg ggccagggaa ccctggtcac cgtctcctca     420
gctagc                                                                426
```

<210> SEQ ID NO 47
<211> LENGTH: 142
<212> TYPE: PRT
<213> ORGANISM: Homo sapiens

<400> SEQUENCE: 47

```
Met Glu Phe Gly Leu Ser Trp Leu Phe Leu Val Ala Ile Leu Lys Gly
  1               5                  10                  15

Val Gln Cys Glu Val Gln Leu Leu Glu Ser Gly Gly Gly Leu Val Gln
                 20                  25                  30

Pro Gly Gly Ser Leu Arg Leu Ser Cys Ala Ala Ser Gly Phe Thr Phe
             35                  40                  45

Ser Ser Tyr Ala Met Ser Trp Val Arg Gln Ala Pro Gly Lys Gly Leu
         50                  55                  60

Glu Trp Val Ser Asp Ile Ser Gly Ser Gly Gly Tyr Thr Tyr Tyr Ala
 65                  70                  75                  80
```

```
Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Thr Gly Asp Gly Ser Gly Ser Tyr Ser Pro Asp
        115                 120                 125

Ser Trp Gly Gln Gly Thr Leu Val Thr Val Ser Ser Ala Ser
130                 135                 140
```

<210> SEQ ID NO 48
<211> LENGTH: 390
<212> TYPE: DNA
<213> ORGANISM: Homo sapiens

<400> SEQUENCE: 48

```
atggacatga gggtcctcgc tcagctcctg gggctcctgc tgctctgttt cccaggtgcc    60
agatgtgaca tccagatgac ccagtctcca tcctcactgt ctgcatctgt aggagacaga   120
gtcaccatca cttgtcgggc gagtcagggt attagcaggt ggttagcctg gtatcagcag   180
aaaccagaga aagcccctaa gtccctgatc tatgctgcat ccagtttgca aagtggggtc   240
ccatcaaggt tcagcggcag tggatctggg acagatttca ctctcaccat cagcagcctg   300
cagcctgaag attttgcaac ttattactgc caacagtata atagttaccc gtacactttt   360
ggccagggga ccaagctgga gatcaaacga                                    390
```

<210> SEQ ID NO 49
<211> LENGTH: 130
<212> TYPE: PRT
<213> ORGANISM: Homo sapiens

<400> SEQUENCE: 49

```
Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Arg Trp Leu Ala Trp Tyr Gln Gln Lys Pro Glu Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Tyr Pro Tyr Thr Phe Gly Gln Gly Thr Lys Leu Glu Ile
        115                 120                 125

Lys Arg
    130
```

<210> SEQ ID NO 50
<211> LENGTH: 426
<212> TYPE: DNA
<213> ORGANISM: Homo sapiens

<400> SEQUENCE: 50

```
atggagtttg ggctgagctg gcttttcctt gtggctattt taaaaggtgt ccagtgtgag    60
```

```
gtgcagctgt tggagtctgg gggaggcttg gtacagcctg gggggtccct gagactctcc    120
tgtgcagcct ctggattcac ctttagcagc tatgccatga gctgggtccg ccaggctcca    180 gggaagggc tggagtgggt ctcagatatt agtggtagtg gtggttacac atactacgca     240
gactccgtga agggccggtt caccatctcc agagacaatt ccaagaaaac gctgtatctg    300
caaatgaaca gcctgagagc cgaggacacg gccgtatatt actgtgcgaa aacaggcgat    360
ggttcgggga gttattcccc tgactactgg ggccagggaa ccctggtcac cgtctcctca    420
gctagc                                                               426
```

<210> SEQ ID NO 51
<211> LENGTH: 142
<212> TYPE: PRT
<213> ORGANISM: Homo sapiens

<400> SEQUENCE: 51

```
Met Glu Phe Gly Leu Ser Trp Leu Phe Leu Val Ala Ile Leu Lys Gly
  1               5                  10                  15

Val Gln Cys Glu Val Gln Leu Leu Glu Ser Gly Gly Gly Leu Val Gln
             20                  25                  30

Pro Gly Gly Ser Leu Arg Leu Ser Cys Ala Ala Ser Gly Phe Thr Phe
         35                  40                  45

Ser Ser Tyr Ala Met Ser Trp Val Arg Gln Ala Pro Gly Lys Gly Leu
     50                  55                  60

Glu Trp Val Ser Asp Ile Ser Gly Ser Gly Gly Tyr Thr Tyr Tyr Ala
 65                  70                  75                  80

Asp Ser Val Lys Gly Arg Phe Thr Ile Ser Arg Asp Asn Ser Lys Lys
                 85                  90                  95

Thr Leu Tyr Leu Gln Met Asn Ser Leu Arg Ala Glu Asp Thr Ala Val
            100                 105                 110

Tyr Tyr Cys Ala Lys Thr Gly Asp Gly Ser Gly Ser Tyr Ser Pro Asp
        115                 120                 125

Tyr Trp Gly Gln Gly Thr Leu Val Thr Val Ser Ser Ala Ser
    130                 135                 140
```

<210> SEQ ID NO 52
<211> LENGTH: 390
<212> TYPE: DNA
<213> ORGANISM: Homo sapiens

<400> SEQUENCE: 52

```
atggacatga gggtcctcgc tcagctcctg gggctcctgc tgctctgttt cccaggtgcc    60
agatgtgaca tccagatgac ccagtctcca tcctcactgt ctgcatctgt aggagacaga   120
gtcaccatca cttgtcgggc gagtcagggt attagcagct ggttagcctg gtatcagcag   180
aaaccagaga agcccctaa gtccctgatc tatgctgcat ccagtttgca aagtggggtc    240
ccatcaaggt tcagcggcag tggatctggg acagatttca ctctcaccat cagcagcctg   300
cagcctgaag attttgcaac ttattactgc caacagtata atagttaccc gtacactttt   360
ggccagggga ccaagctgga gatcaaacga                                    390
```

<210> SEQ ID NO 53
<211> LENGTH: 130
<212> TYPE: PRT
<213> ORGANISM: Homo sapiens

<400> SEQUENCE: 53

```
Met Asp Met Arg Val Leu Ala Gln Leu Leu Gly Leu Leu Leu Leu Cys
 1               5                  10                  15
Phe Pro Gly Ala Arg Cys Asp Ile Gln Met Thr Gln Ser Pro Ser Ser
                20                  25                  30
Leu Ser Ala Ser Val Gly Asp Arg Val Thr Ile Thr Cys Arg Ala Ser
            35                  40                  45
Gln Gly Ile Ser Ser Trp Leu Ala Trp Tyr Gln Gln Lys Pro Glu Lys
    50                  55                  60
Ala Pro Lys Ser Leu Ile Tyr Ala Ala Ser Ser Leu Gln Ser Gly Val
65                  70                  75                  80
Pro Ser Arg Phe Ser Gly Ser Gly Ser Gly Thr Asp Phe Thr Leu Thr
                85                  90                  95
Ile Ser Ser Leu Gln Pro Glu Asp Phe Ala Thr Tyr Tyr Cys Gln Gln
            100                 105                 110
Tyr Asn Ser Tyr Pro Tyr Thr Phe Gly Gln Gly Thr Lys Leu Glu Ile
        115                 120                 125
Lys Arg
    130
```

<210> SEQ ID NO 54
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 54
gcgactaagt cgaccatgga gtttgggctg agctg                          35

<210> SEQ ID NO 55
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 55
tgggcccttg gtgctagctg aggagacggt gaccg                          35

<210> SEQ ID NO 56
<211> LENGTH: 45
<212> TYPE: DNA
<213> ORGANISM: Artificial Sequence
<220> FEATURE:
<223> OTHER INFORMATION: Description of Artificial Sequence:primer

<400> SEQUENCE: 56
agagagagag gtcgaccacc atggagtttg gctgagctg ggttt                45

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 57
agagagagag gctagctgag gagacggtga ccagggtgc                      39

<210> SEQ ID NO 58
<211> LENGTH: 45
<212> TYPE: DNA

```
<213> ORGANISM: Artificial Sequence
<220> FEATURE:
<223> OTHER INFORMATION: Description of Artificial Sequence:primer

<400> SEQUENCE: 58
agagagagag gtcgaccacc atggagtttg ggctgagctg ggttt                    45

<210> SEQ ID NO 59
<211> LENGTH: 41
<212> TYPE: DNA
<213> ORGANISM: Artificial Sequence
<220> FEATURE:
<223> OTHER INFORMATION: Description of Artificial Sequence:primer

<400> SEQUENCE: 59
agagagagag gctagctgag gagacggtga ccagggttcc c                        41

<210> SEQ ID NO 60
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 60
atcacagatc tctcaccatg gacatgaggg tcccc                               35

<210> SEQ ID NO 61
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 61
acagatggtg cagccaccgt acgtttaatc tccag                               35

<210> SEQ ID NO 62
<211> LENGTH: 45
<212> TYPE: DNA
<213> ORGANISM: Artificial Sequence
<220> FEATURE:
<223> OTHER INFORMATION: Description of Artificial Sequence:primer

<400> SEQUENCE: 62
agagagagag agatctcacc atggaagccc cagctcagct tctct                    45

<210> SEQ ID NO 63
<211> LENGTH: 42
<212> TYPE: DNA
<213> ORGANISM: Artificial Sequence
<220> FEATURE:
<223> OTHER INFORMATION: Description of Artificial Sequence:primer

<400> SEQUENCE: 63
agagagagag cgtacgtttg atttccacct tggtcccttg gc                       42

<210> SEQ ID NO 64
<211> LENGTH: 44
<212> TYPE: DNA
<213> ORGANISM: Artificial Sequence
<220> FEATURE:
<223> OTHER INFORMATION: Description of Artificial Sequence:primer

<400> SEQUENCE: 64
agagagagag atctctcacc atgtcgccat cacaactcat tggg                     44
```

<210> SEQ ID NO 65
<211> LENGTH: 41
<212> TYPE: DNA
<213> ORGANISM: Artificial Sequence
<220> FEATURE:
<223> OTHER INFORMATION: Description of Artificial Sequence:primer

<400> SEQUENCE: 65
agagagagag cgtacgtttg atatccactt tggtcccagg g                    41

<210> SEQ ID NO 66
<211> LENGTH: 45
<212> TYPE: DNA
<213> ORGANISM: Artificial Sequence
<220> FEATURE:
<223> OTHER INFORMATION: Description of Artificial Sequence:primer

<400> SEQUENCE: 66
agagagagag agatctcacc atggaagccc cagctcagct tctct                45

<210> SEQ ID NO 67
<211> LENGTH: 41
<212> TYPE: DNA
<213> ORGANISM: Artificial Sequence
<220> FEATURE:
<223> OTHER INFORMATION: Description of Artificial Sequence:primer

<400> SEQUENCE: 67
agagagagag cgtacgtttg atctccacct tggtccctcc g                    41

<210> SEQ ID NO 68
<211> LENGTH: 45
<212> TYPE: DNA
<213> ORGANISM: Artificial Sequence
<220> FEATURE:
<223> OTHER INFORMATION: Description of Artificial Sequence:primer

<400> SEQUENCE: 68
agagagagag agatctcacc atggacatga gggtcctcgc tcagc                45

<210> SEQ ID NO 69
<211> LENGTH: 41
<212> TYPE: DNA
<213> ORGANISM: Artificial Sequence
<220> FEATURE:
<223> OTHER INFORMATION: Description of Artificial Sequence:primer

<400> SEQUENCE: 69
agagagagag cgtacgtttg atctccagct tggtcccctg g                    41

<210> SEQ ID NO 70
<211> LENGTH: 48
<212> TYPE: DNA
<213> ORGANISM: Artificial Sequence
<220> FEATURE:
<223> OTHER INFORMATION: Description of Artificial Sequence:primer

<400> SEQUENCE: 70
agagagagag gtcgaccacc atggatctca tgtgcaagaa aatgaagc             48

<210> SEQ ID NO 71
<211> LENGTH: 41
<212> TYPE: DNA
<213> ORGANISM: Artificial Sequence
<220> FEATURE:

<223> OTHER INFORMATION: Description of Artificial Sequence:primer

<400> SEQUENCE: 71
agagagagag gctagctgag gagacggtga ccgtggtccc t                41

<210> SEQ ID NO 72
<211> LENGTH: 45
<212> TYPE: DNA
<213> ORGANISM: Artificial Sequence
<220> FEATURE:
<223> OTHER INFORMATION: Description of Artificial Sequence:primer

<400> SEQUENCE: 72
agagagagag gtcgaccacc atggagtttg ggctgagctg gcttt            45

<210> SEQ ID NO 73
<211> LENGTH: 41
<212> TYPE: DNA
<213> ORGANISM: Artificial Sequence
<220> FEATURE:
<223> OTHER INFORMATION: Description of Artificial Sequence:primer

<400> SEQUENCE: 73
agagagagag gctagctgag gagacggtga ccagggttcc c                41

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 74
cggggtacgt gccaagcatc ctcgtg                                 26

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 75
atgctgggcg cccgggaagt atgtac                                 26

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 76
gaaagatgag ctggaggacc gcaata                                 26

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 77
ccaagggccc atcggtcttc cccctggcac                             30

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 78
gacaccctca tgatctcccg gacc                                          24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 79
tgttctccgg ctgcccattg ctct                                          24

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 80
ggtccgggag atcatgaggg tgtcctt                                       27

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 81
tggctgcacc atctgtcttc atcttc                                        26

<210> SEQ ID NO 82
<211> LENGTH: 1413
<212> TYPE: DNA
<213> ORGANISM: Homo sapiens

<400> SEQUENCE: 82
atggagtttg ggctgagctg ggttttcctc gttgctcttt taagaggtgt ccagtgtcag    60
gtgcagttgg tggagtctgg gggaggcgtg gtccagcctg gaggtccct gagactctcc    120 tgtgcagcgt ctggattcac cttcagtcac tatggcatgc actgggtccg ccaggctcca   180
ggcaaggggc tggagtgggt ggcacttata tggtatgatg aagtaataa atactatgca   240 gactccgtga agggccgatt caccatctcc agagacaatt ccaagaacac gctgtatctg   300
caaatgaaca gcctgagagc cgaggacacg gctgtgtatt actgtgcgag agatccctta   360
gcagctggta cgtcctactt tgactactgg ggccagggaa ccctggtcac cgtctcctca   420
gcctccacca agggcccatc ggtcttcccc ctggcaccct cctccaagag cacctctggg   480
ggcacagcgg ccctgggctg cctggtcaag gactacttcc ccgaaccggt gacggtgtcg   540
tggaactcag gcgccctgac cagcggcgtg cacaccttcc cggctgtcct acagtcctca   600
ggactctact ccctcagcag cgtggtgacc gtgccctcca gcagcttggg cacccagacc   660
tacatctgca acgtgaatca caagcccagc aacaccaagg tggacaagaa agttgagccc   720

-continued

```
aaatcttgtg acaaaactca cacatgccca ccgtgcccag cacctgaact cctgggggga      780
ccgtcagtct tcctcttccc cccaaaaccc aaggacaccc tcatgatctc ccggacccct      840
gaggtcacat gcgtggtggt ggacgtgagc cacgaagacc ctgaggtcaa gttcaactgg      900
tacgtggacg gcgtggaggt gcataatgcc aagacaaagc cgcgggagga gcagtacaac      960
agcacgtacc gtgtggtcag cgtcctcacc gtcctgcacc aggactggct gaatggcaag     1020
gagtacaagt gcaaggtctc caacaaagcc ctcccagccc ccatcgagaa aaccatctcc     1080
aaagccaaag ggcagccccg agaaccacag gtgtacaccc tgcccccatc ccgggatgag     1140
ctgaccaaga accaggtcag cctgacctgc ctggtcaaag gcttctatcc cagcgacatc     1200
gccgtggagt gggagagcaa tgggcagccg gagaacaact acaagaccac gcctcccgtg     1260
ctggactccg acggctcctt cttcctctac agcaagctca ccgtggacaa gagcaggtgg     1320
cagcagggga acgtcttctc atgctccgtg atgcatgagg ctctgcacaa ccactacacg     1380
cagaagagcc tctccctgtc tccgggtaaa tga                                  1413

<210> SEQ ID NO 83
<211> LENGTH: 470
<212> TYPE: PRT
<213> ORGANISM: Homo sapiens

<400> SEQUENCE: 83

Met Glu Phe Gly Leu Ser Trp Val Phe Leu Val Ala Leu Leu Arg Gly
  1               5                  10                  15

Val Gln Cys Gln Val Gln Leu Val Glu Ser Gly Gly Gly Val Val Gln
             20                  25                  30

Pro Gly Arg Ser Leu Arg Leu Ser Cys Ala Ala Ser Gly Phe Thr Phe
         35                  40                  45

Ser His Tyr Gly Met His Trp Val Arg Gln Ala Pro Gly Lys Gly Leu
     50                  55                  60

Glu Trp Val Ala Leu Ile Trp Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Pro Leu Ala Ala Gly Thr Ser Tyr Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255
```

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 84
<211> LENGTH: 702
<212> TYPE: DNA
<213> ORGANISM: Homo sapiens

<400> SEQUENCE: 84
atgtcgccat cacaactcat tgggtttctg ctgctctggg ttccagcctc caggggtgaa    60
attgtgctga ctcagtctcc agactttcag tctgtgactc caaggagaa agtcaccatc    120 acctgccggg ccagtcagag cattggtagt agcttacact ggtaccagca gaaaccagat   180
cagtctccaa agctcctcat caagtatgct tcccagtcct ctcagggggt ccctcgagg    240 ttcagtggca gtggatctgg gacagatttc accctcacca tcaatagcct ggaagctgaa    300
gatgctgcag cgtattactg tcatcagagt agtagtttac cattcacttt cggccctggg    360
accaaagtgg atatcaaacg aactgtggct gcaccatctg tcttcatctt cccgccatct    420
gatgagcagt tgaaatctgg aactgcctct gttgtgtgcc tgctgaataa cttctatccc    480
agagaggcca agtacagtg gaaggtggat aacgccctcc aatcgggtaa ctcccaggag    540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgtt ag    702

<210> SEQ ID NO 85
<211> LENGTH: 233
<212> TYPE: PRT

<213> ORGANISM: Homo sapiens

<400> SEQUENCE: 85

```
Met Ser Pro Ser Gln Leu Ile Gly Phe Leu Leu Trp Val Pro Ala
 1               5                  10                  15
Ser Arg Gly Glu Ile Val Leu Thr Gln Ser Pro Asp Phe Gln Ser Val
                20                  25                  30
Thr Pro Lys Glu Lys Val Thr Ile Thr Cys Arg Ala Ser Gln Ser Ile
            35                  40                  45
Gly Ser Ser Leu His Trp Tyr Gln Gln Lys Pro Asp Gln Ser Pro Lys
        50                  55                  60
Leu Leu Ile Lys Tyr Ala Ser Gln Ser Phe Ser Gly Val Pro Ser Arg
 65                 70                  75                  80
Phe Ser Gly Ser Gly Ser Gly Thr Asp Phe Thr Leu Thr Ile Asn Ser
                85                  90                  95
Leu Glu Ala Glu Asp Ala Ala Ala Tyr Tyr Cys His Gln Ser Ser Ser
            100                 105                 110
Leu Pro Phe Thr Phe Gly Pro Gly Thr Lys Val Asp Ile Lys Arg Thr
        115                 120                 125
Val Ala Ala Pro Ser Val Phe Ile Phe Pro Pro Ser Asp Glu Gln Leu
    130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
    210                 215                 220
Thr Lys Ser Phe Asn Arg Gly Glu Cys
225                 230
```

<210> SEQ ID NO 86
<211> LENGTH: 1434
<212> TYPE: DNA
<213> ORGANISM: Homo sapiens

<400> SEQUENCE: 86

```
atggatctca tgtgcaagaa aatgaagcac ctgtggttct tcctcctgct ggtggcggct    60
cccagatggg tcctgtccca gctgcaggtg caggagtcgg gcccaggact ggtgaagcct   120
tcggagaccc tgtccctcat ctgcactgtc tctggtggct ccatcaggac cagtggttac   180
tactggggct ggttccgcca gcccccaggg aagggactgg agtggattgg actagtcat   240
aatagtggga gcacctacta caacccgtcc ctcaagagtc gagtcaccat atccgtagac   300
acgtccaaga accagttctc cctgaagctg aactctgtga ccgccgcaga cacggctgtg   360
tattactgtg cgagacaagg ttacgatttt aaagtcaata tagacgtctg gggacaaggg   420
accacggtca ccgtctcctc agcctccacc aagggcccat cggtcttccc cctggcaccc   480
tcctccaaga gcacctctgg gggcacagcg gccctgggct gcctggtcaa ggactacttc   540
cccgaaccgg tgacggtgtc gtggaactca ggcgccctga ccagcggcgt gcacaccttc   600
ccggctgtcc tacagtcctc aggactctac tccctcagca gcgtggtgac cgtgccctcc   660
```

-continued

```
agcagcttgg gcacccagac ctacatctgc aacgtgaatc acaagcccag caacaccaag      720
gtggacaaga aagttgagcc caaatcttgt gacaaaactc acacatgccc accgtgccca      780
gcacctgaac tcctgggggg accgtcagtc ttcctcttcc ccccaaaacc caaggacacc      840
ctcatgatct cccggacccc tgaggtcaca tgcgtggtgg tggacgtgag ccacgaagac      900
cctgaggtca agttcaactg gtacgtggac ggcgtggagg tgcataatgc caagacaaag      960
ccgcgggagg agcagtacaa cagcacgtac cgtgtggtca gcgtcctcac cgtcctgcac     1020
caggactggc tgaatggcaa ggagtacaag tgcaaggtct ccaacaaagc cctcccagcc     1080
cccatcgaga aaaccatctc caaagccaaa gggcagcccc gagaaccaca ggtgtacacc     1140
ctgcccccat cccgggatga gctgaccaag aaccaggtca gcctgacctg cctggtcaaa     1200
ggcttctatc ccagcgacat cgccgtggag tgggagagca atgggcagcc ggagaacaac     1260
tacaagacca cgcctcccgt gctggactcc gacggctcct tcttcctcta cagcaagctc     1320
accgtggaca agagcaggtg gcagcagggg aacgtcttct catgctccgt gatgcatgag     1380
gctctgcaca accactacac gcagaagagc ctctccctgt ctccgggtaa atga           1434
```

<210> SEQ ID NO 87
<211> LENGTH: 477
<212> TYPE: PRT
<213> ORGANISM: Homo sapiens

<400> SEQUENCE: 87

```
Met Asp Leu Met Cys Lys Lys Met Lys His Leu Trp Phe Phe Leu Leu
  1               5                  10                  15

Leu Val Ala Ala Pro Arg Trp Val Leu Ser Gln Leu Gln Val Gln Glu
                 20                  25                  30

Ser Gly Pro Gly Leu Val Lys Pro Ser Glu Thr Leu Ser Leu Ile Cys
             35                  40                  45

Thr Val Ser Gly Gly Ser Ile Arg Thr Ser Gly Tyr Tyr Trp Gly Trp
         50                  55                  60

Phe Arg Gln Pro Pro Gly Lys Gly Leu Glu Trp Ile Gly Thr Ser His
 65                  70                  75                  80

Asn Ser Gly Ser Thr Tyr Tyr Asn Pro Ser Leu Lys Ser Arg Val Thr
                 85                  90                  95

Ile Ser Val Asp Thr Ser Lys Asn Gln Phe Ser Leu Lys Leu Asn Ser
                100                 105                 110

Val Thr Ala Ala Asp Thr Ala Val Tyr Tyr Cys Ala Arg Gln Gly Tyr
            115                 120                 125

Asp Phe Lys Val Asn Ile Asp Val Trp Gly Gln Gly Thr Thr Val Thr
        130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240
```

Val Asp Lys Lys Val Glu Pro Lys Ser Cys Asp Lys Thr His Thr Cys
            245                 250                 255

Pro Pro Cys Pro Ala Pro Glu Leu Leu Gly Gly Pro Ser Val Phe Leu
        260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
        290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
        370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475

<210> SEQ ID NO 88
<211> LENGTH: 705
<212> TYPE: DNA
<213> ORGANISM: Homo sapiens

<400> SEQUENCE: 88
atggaagccc cagctcagct tctcttcctc ctgctactct ggctcccaga taccaccgga        60
gaaattgtgt tgacacagtc tccagccacc ctgtctttgt ctccagggga aagagccacc       120
ctctcctgca gggccagtca gagtgttagc agctacttag cctggtacca acagaaacct       180
ggccaggctc ccaggctcct catctatgat gcatccaaca gggccactgg catcccagcc       240
aggttcagtg gcagtgggtc tgggacagac ttcactctca ccatcagcag cctagagcct       300
gaagattttg cagtttatta ctgtcagcag cgtagcaact ggccgctcac tttcggcgga       360
gggaccaagg tggagatcaa acgaactgtg gctgcaccat ctgtcttcat cttcccgcca       420
tctgatgagc agttgaaatc tggaactgcc tctgttgtgt gcctgctgaa taacttctat       480
cccagagagg ccaaagtaca gtggaaggtg gataacgccc tccaatcggg taactcccag       540
gagagtgtca cagagcagga cagcaaggac agcacctaca gcctcagcag caccctgacg       600
ctgagcaaag cagactacga gaaacacaaa gtctacgcct gcgaagtcac ccatcagggc       660
ctgagctcgc ccgtcacaaa gagcttcaac aggggagagt gttag                      705

<210> SEQ ID NO 89

```
<211> LENGTH: 234
<212> TYPE: PRT
<213> ORGANISM: Homo sapiens

<400> SEQUENCE: 89

Met Glu Ala Pro Ala Gln Leu Leu Phe Leu Leu Leu Leu Trp Leu Pro
 1               5                  10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
 65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```